United States Patent
Hayashizaki et al.

(10) Patent No.: US 9,586,987 B2
(45) Date of Patent: Mar. 7, 2017

(54) PRIMER SET FOR ISOTHERMAL AMPLICATION OF A TARGET NUCLEIC ACID SEQUENCE

(75) Inventors: Yoshihide Hayashizaki, Wako (JP); Yasumasa Kimura, Wako (JP); Kengo Usui, Wako (JP); Yuki Tanaka, Wako (JP); Yuki Kawai, Yokohama (JP)

(73) Assignee: Kabushiki Kaisha DNAFORM, Kanagawa (JP)

( * ) Notice: Subject to any disclaimer, the term of this patent is extended or adjusted under 35 U.S.C. 154(b) by 438 days.

(21) Appl. No.: 14/343,511

(22) PCT Filed: Sep. 7, 2012

(86) PCT No.: PCT/JP2012/072997
§ 371 (c)(1),
(2), (4) Date: Jun. 2, 2014

(87) PCT Pub. No.: WO2013/035875
PCT Pub. Date: Mar. 14, 2013

(65) Prior Publication Data
US 2014/0295447 A1    Oct. 2, 2014

(30) Foreign Application Priority Data
Sep. 8, 2011    (JP) .................................. 2011-196597

(51) Int. Cl.
C12P 19/34    (2006.01)
C07H 21/04    (2006.01)
C12Q 1/68    (2006.01)

(52) U.S. Cl.
CPC ........... *C07H 21/04* (2013.01); *C12Q 1/6844* (2013.01); *C12Q 1/6853* (2013.01)

(58) Field of Classification Search
USPC .............................................. 435/6.12, 91.2
See application file for complete search history.

(56) References Cited

U.S. PATENT DOCUMENTS 4,554,088 A    11/1985    Whitehead et al.
4,605,735 A    8/1986    Miyoshi et al.
(Continued)

FOREIGN PATENT DOCUMENTS

EP    0 320 308    6/1989
EP    1 312 682    5/2003
(Continued)

OTHER PUBLICATIONS

Kimura et al., BBRC 383, 455-459 (2009).*
(Continued)

*Primary Examiner* — Kenneth Horlick
(74) *Attorney, Agent, or Firm* — Hamre, Schumann, Mueller & Larson, P.C.

(57) ABSTRACT

The present invention provides a primer set including primers that can be designed easily, with which an amplification distance can be shortened. Provided is a primer set for use in a method for isothermally amplifying a target nucleic acid sequence 4. The primer set includes a first primer 1F and a second primer 1R. The first primer 1F includes, on the 3' side thereof, a sequence (A') that can hybridize to a sequence (A) on the 3' side of the target nucleic acid sequence. The second primer 1R includes, on the 3' side thereof, a sequence (B') that can hybridize to a sequence (B) on the 3' side of either a strand extended from the first primer or a complementary strand of the target nucleic acid sequence 4. The first primer 1F and the second primer 1R include, on the 5' sides thereof, sequences (C) that are substantially identical to each other.

16 Claims, 31 Drawing Sheets

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 5,455,166 | A | 10/1995 | Walker |
| 5,554,517 | A | 9/1996 | Davey et al. |
| 5,824,517 | A | 10/1998 | Cleuziat et al. |
| 6,046,807 | A | 4/2000 | Chandler |
| 6,057,107 | A | 5/2000 | Fulton |
| 6,090,552 | A | 7/2000 | Nazarenko et al. |
| 6,207,372 | B1 * | 3/2001 | Shuber ............... C12Q 1/686 435/6.12 |
| 6,410,278 | B1 | 6/2002 | Notomi et al. |
| 6,617,106 | B1 | 9/2003 | Benner |
| 7,521,178 | B1 | 4/2009 | Asada et al. |
| 2004/0038253 | A1 | 2/2004 | Nagamine |
| 2007/0117119 | A1 | 5/2007 | Akita et al. |
| 2007/0190531 | A1 | 8/2007 | Mitani et al. |

FOREIGN PATENT DOCUMENTS

| | | |
|---|---|---|
| JP | 59-093099 | 5/1984 |
| JP | 59-148798 | 8/1984 |
| JP | 59/204200 | 11/1984 |
| JP | 4-501959 | 4/1992 |
| JP | 7-006986 | 1/1995 |
| JP | 7-114718 | 12/1995 |
| JP | 2650159 B2 | 9/1997 |
| JP | 2710159 B2 | 2/1998 |
| JP | 2000-245460 | 9/2000 |
| JP | 3313358 B2 | 8/2002 |
| JP | 3897805 B2 | 3/2007 |
| TW | 200525026 | 8/2005 |
| WO | 87/06270 | 10/1987 |
| WO | 90/06045 | 6/1990 |
| WO | 95/25180 | 9/1995 |
| WO | 96/01327 | 1/1996 |
| WO | 99/09211 | 2/1999 |
| WO | 99/54455 | 10/1999 |
| WO | 00/28082 | 5/2000 |
| WO | 02/16639 | 2/2002 |
| WO | 02/24902 | 3/2002 |
| WO | 2005/063977 | 7/2005 |
| WO | 2008/104794 | 9/2008 |

OTHER PUBLICATIONS

Larrick, "Message Amplification Phenotyping (MAPPing)—principles, practice and potential", Trends Biotechnol., 1992, vol. 10, No. 5, pp. 146-152.

Sambrook, et al., "Molecular Cloning", $2^{nd}$ edition, Cold Spring Harbor Laboratory Press, 1989—33 pages.

Horlacher, et al., "Recognition by viral and cellular DNA polymerases of nucleosides bearing bases with nonstandard hydrogen bonding patterns", Proc. Natl. Acad. Sci. USA, 1995, vol. 92, pp. 6329-6333.

Sismour, et al., "First PCR amplification of DNA containing a non-standard base pair A", Biochemistry, 2003, vol. 42, No. 28, p. 8598.

Lutz, et al., "Recognition of a Non-standard Base Pair by Thermostable DNA Polymerases", Bioorganic & Medicinal Chemistry Letters, 1998, vol. 8, No. 10, pp. 1149-1152.

Kimura, et al., "Optimization of turn-back primers in isothermal amplification", Nucleic Acids Research, 2011, vol. 39, No. 9, p. e59.

Shuber, et al., "A Simplified Prodedure for Developing Multiplex PCRS", Genome Research, Cold Spring Harbor Laboratory Press, vol. 5, No. 5, Dec. 1995, pp. 488-493.

Supplementary Partial European Search Report, issued in corresponding European Patent Application No. 12829819.7, Apr. 23, 2015, 6 pages.

* cited by examiner (+) with template DNA
(−) without template DNA

DNA fragment 1: full length 92 bp

DNA fragment 2: full length 186 bp

PRIMER SET FOR ISOTHERMAL AMPLIFICATION OF A TARGET NUCLEIC ACID SEQUENCE

TECHNICAL FIELD

The present invention relates to a primer set, a method for amplifying a target nucleic acid sequence using the same, and a method for detecting a mutated nucleic acid using the same.

BACKGROUND ART

In the field of genetic engineering, as a method allowing direct analysis of a genetic feature, analysis based on the complementarity of nucleic acid sequences has been known. In such analysis, when the amount of a target gene in a sample is small, the detection thereof generally cannot be achieved easily. Thus, it is necessary to amplify the target gene itself in advance.

Amplification of the target gene (nucleic acid amplification) chiefly is carried out by an enzymatic method utilizing a DNA polymerase. Major examples of such an enzymatic method include: a PCR method (Polymerase Chain Reaction method; U.S. Pat. No. 4,683,195 (Patent Document 1), U.S. Pat. No. 4,683,202 (Patent Document 2), and U.S. Pat. No. 4,800,159 (Patent Document 3)); and a RT-PCR method (reverse transcription PCR method; Trends in Biotechnology 10, pp. 146-152, 1992 (Non-Patent Document 1)), which is a PCR method combined with a reverse transcriptase reaction. These methods allow the target gene to be amplified from DNA or RNA by repeating a reaction including the following three stages: dissociation of a double-stranded nucleic acid serving as a template into single-stranded nucleic acids (denaturation); annealing of a primer to the single-stranded nucleic acid; and synthesis of a complementary strand from the primer (extension). In these methods, the temperature of the reaction solution needs to be adjusted to temperatures suitable for the above-described three stages, and these three steps of temperature adjustment need to be repeated.

Furthermore, European Patent Publication No. 0320308 (Patent Document 4) discloses a ligase chain reaction method (LCR method), in which a known gene sequence is amplified by performing a two-step thermal cycling reaction (reaction repeating heating and cooling) using a heat-resistant DNA ligase. However, in the methods described above, it is necessary to use an expensive thermal cycler that can achieve strict temperature control over time over a wide temperature range. Besides, these reactions are carried out under two to three kinds of temperature conditions. Thus, time for adjustment to each reaction temperature is required, and the time required increases in keeping with the number of cycles.

In order to solve the above-described problems, there have been developed nucleic acid amplification methods that can be carried out under isothermal conditions. Examples of such methods include: an SDA (strand displacement amplification) method described in JP 7(1995)-114718 B (Patent Document 5); a 3SR (self-sustained sequence replication) method; an NASBA (nucleic acid sequence based amplification) method described in Japanese Patent No. 2650159 (Patent Document 6); a TMA (transcription-mediated amplification) method; a Q beta replicase method described in Japanese Patent No. 2710159 (Patent Document 7); various kinds of improved SDA methods described in U.S. Pat. No. 5,824,517 (Patent Document 8), WO 99/09211 (Patent Document 9), and WO 95/25180 (Patent Document 10); a LAMP (Loop-Mediated Isothermal Amplification) method described in WO 00/28082 (Patent Document 11); an ICAN (Isothermal and Chimeric primer-initiated Amplification of Nucleic acids) method described in WO 02/16639 (Patent Document 12); and a SmartAmp2 method described in Japanese Patent No. 3897805 (Patent Document 13). In these isothermal nucleic acid amplification methods, reactions at all the stages proceed simultaneously in a reaction mixture kept at a given temperature.

Among the above-described isothermal amplification methods, the LAMP method and the SmartAmp2 method are superior in practical utility. The LAMP method is an isothermal amplification method in which two turn-back primers (TPs) and two outer primers (OPs) are essential. Thus, in the LAMP method, four kinds of primers are required, and genome recognition sites are six in total. FIG. 11 illustrates an example of the LAMP method. In FIG. 11, the two OPs are omitted, and only the two TPs are shown. As shown in FIG. 11, each of the TPs includes, on the 3' side thereof, a sequence that hybridizes to a target nucleic acid sequence, and includes, on the 5' side thereof, a sequence complementary to the primer-extended strand. For example, in FIG. 11, one of the TPs (on the left in FIG. 11) includes, on the 3' side thereof, a sequence (A') complementary to a sequence (A) of the target nucleic acid sequence, and includes, on the 5' side thereof, a sequence (M) complementary to a sequence (M') of the primer-extended strand. The other TP (on the right in FIG. 11) has the same structure. When the TP with the above structure hybridizes to the template sequence and an extended strand thereof is formed, the 5' side of the TP turns back to hybridize to the extended strand. As a result, a stem-loop structure is formed on the 5' side of the primer-extended strand. Because two TPs are used in the LAMP method, the LAMP method has a problem in that it is difficult to shorten the sequence of a region to be amplified in the target nucleic acid sequence. Moreover, because four kinds of primers are required and there are six genome recognition sites in total in the LAMP method as described above, the LAMP method also has a problem in that primer design is difficult. On the other hand, the SmartAmp2 method uses a TP and a folding primer (FP), so that the above-described problems in the LAMP method do not occur in the SmartAmp2 method. FIG. 12 illustrates an example of the SmartAmp2 method. As shown in FIG. 12, in the SmartAmp2 method, one of the primers is a TP and the other primer is a FP. As shown in FIG. 12, the FP includes, on the 3' side thereof, a sequence (B') complementary to a sequence (B) of a target nucleic acid sequence, and includes, on the 5' side thereof, a folding sequence including sequences F-F' that are complementary to each other on a single strand. Because the SmartAmp2 method uses the TP and the FP, there are three genome recognition sites. Besides, the FP does not turn back. Accordingly, the SmartAmp2 method is advantageous not only in that it achieves high amplification speed and high specificity but also in that it allows easy primer design and shortening of a region to be amplified.

CITATION LIST

Patent Document(s)

Patent Document 1: U.S. Pat. No. 4,683,195
Patent Document 2: U.S. Pat. No. 4,683,202
Patent Document 3: U.S. Pat. No. 4,800,159

Patent Document 4: European Patent Publication No. 0320308
Patent Document 5: JP 7(1995)-114718 B
Patent Document 6: Japanese Patent No. 2650159
Patent Document 7: Japanese Patent No. 2710159
Patent Document 8: U.S. Pat. No. 5,824,517
Patent Document 9: WO 99/09211
Patent Document 10: WO 95/25180
Patent Document 11: WO 00/28082
Patent Document 12: WO 02/16639
Patent Document 13: Japanese Patent No. 3897805

Non-Patent Document(s)

Non-Patent Document 1: Trends in Biotechnology 10, pp. 146-152, 1992

BRIEF SUMMARY OF THE INVENTION

Problem to be Solved by the Invention

As described above, the SmartAmp2 method is a highly practical method with various advantages. However, because the SmartAmp2 method uses a TP, there is a limit to the extent to which the number of genome recognition sites can be decreased and the amplification distance can be shortened.

With the foregoing in mind, it is an object of the present invention to provide a primer set for use in an isothermal amplification method, with which the number of genome recognition sites is small and the amplification distance can be shortened, as well as an isothermal amplification method and a detection method of a mutation(s) in a nucleic acid sequence, carried out using the primer set.

Means for Solving Problem

In order to achieve the above-described object, the present invention provides a primer set for use in a method for isothermally amplifying a target nucleic acid sequence, including: a first primer; and a second primer, wherein the first primer includes, on the 3' side thereof, a sequence (A') that can hybridize to a sequence (A) on the 3' side of the target nucleic acid sequence, the second primer includes, on the 3' side thereof, a sequence (B') that can hybridize to a sequence (B) on the 3' side of either a strand extended from the first primer or a strand complementary to the target nucleic acid sequence, and the first primer and the second primer comprise, on the 5' sides thereof, sequences (C) that are substantially identical to each other.

The present invention also provides a method for isothermally amplifying a target nucleic acid sequence using a primer set, wherein the primer set is the primer set according to the present invention.

The present invention also provides a method for detecting a mutation in a nucleic acid sequence in a nucleic acid sample by an isothermal amplification method using a primer set, wherein the primer set is the primer set according to the present invention, the primer set is designed so that the primer set targets a nucleic acid sequence having or not having the mutation and that a nucleotide residue corresponding to the mutation is included in the sequence (A) complementary to the sequence in the first primer or in the sequence (B) complementary to the sequence in the second primer, and an isothermal amplification reaction using the primer set is carried out in the presence of the nucleic acid sample.

Effects of the Invention

The primer set of the present invention has only two genome recognition sites, and besides, does not use any TP. Thus, according to the primer set of the present invention, primer design can be done easily, and the sequence of a region to be amplified can be shortened. Accordingly, by using the primer set of the present invention, it becomes possible to amplify a short sequence such as microRNA, whereas such a short sequence cannot be amplified by conventional methods. As described above, the present invention provides a primer set and an isothermal amplification method developed by the inventors of the present invention, which are totally different from the SmartAmp2.

MODE FOR CARRYING OUT THE INVENTION

Figure 1:
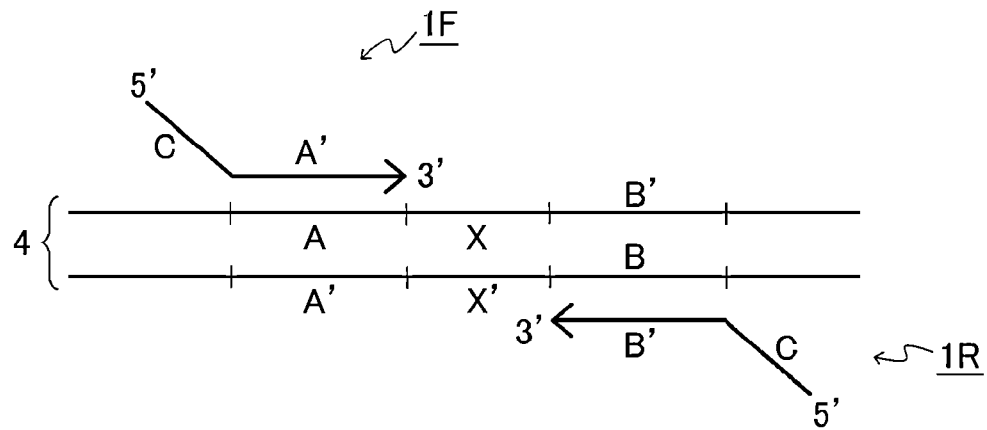
FIG. 1 shows an example of the primer set according to the present invention.

As described above, the first primer and the second primer include, on the 5' sides thereof, sequences (C) that are substantially identical to each other. The state where the two sequences (C) are "substantially identical" means that the two sequences (C) can each hybridize to a complementary sequence in the other primer. Specifically, for example, the two sequences (C) may be perfectly identical to each other (full match), or may include one or more different bases (mismatch). In the case of the mismatch, for example, one of the two sequences (C) may be a sequence obtained by at least one of substitution, insertion, and deletion of a base(s) in the other sequence (C). In the two sequences (C), the number of bases to be substituted, inserted, and/or deleted preferably is not more than two-tenths, more preferably one-tenth of the total number of bases in the two sequences (C). It is particularly preferable that the two sequences (C) are perfectly identical to each other (that is, the number of bases to be substituted, inserted, and/or deleted is 0).

The primer set of the present invention may be configured so that at least one of the first primer and the second primer further includes, on the 5' side of the sequence (C), a folding sequence (D-D') including, on the same strand, two sequences that hybridize to each other.

Also, the primer set of the present invention may be configured so that the first primer further includes, on the 5' side of the sequence (C), a folding sequence (D-D') including, on the same strand, two sequences that hybridize to each other, the second primer further includes, on the 5' side of the sequence (C), a folding sequence (E-E') including, on the same strand, two sequences that hybridize to each other, and the sequence (D-D') and the sequence (E-E') are different from each other.

Also, the primer set of the present invention may be configured so that it further includes a third primer, and the third primer hybridizes to the target nucleic acid sequence, a sequence complementary to the target nucleic acid sequence, or a strand extended from the first primer or the second primer, and the hybridization of the third primer does not compete with the first primer and the second primer.

Another aspect of the present invention may be a first nucleic acid synthesis method for isothermally synthesizing a double-stranded nucleic acid composed of a single-stranded nucleic acid in which the order of at least two different sequences is repeated to a total of two or more times and a nucleic acid complementary to the single-stranded nucleic acid. The first nucleic acid synthesis method includes the following steps (A1) to (A6):

(A1) providing a single-stranded template nucleic acid having a stem-loop structure in which a 3' side stem sequence including the 3' end and a 5' side stem sequence including the 5' end are linked to each other via a loop sequence, with a folding sequence including, on the same strand, two sequences that hybridize to each other being linked to the 3' end of the 3' side stem sequence;

(A2) hybridizing a primer to the loop of the single-stranded template nucleic acid and extending the primer toward the 5' end of the 5' side stem sequence;

(A3) successively continuing the extension of the primer that has reached the 5' end of the 5' side stem sequence from the 5' end of the 5' side stem sequence to the 3' end of the folding sequence;

(A4) successively continuing the extension of the primer that has reached the 3' end of the folding sequence in the step (A3) toward the 5' end of the 5' side stem sequence again, and, by the continuing primer extension, rendering the primer-extended strand hybridizing to the single-stranded template nucleic acid formed in the step (A2) single-stranded through a strand displacement reaction;

(A5) terminating the extension of the primer in the step (A4) at the 5' end of the 5' side stem sequence; and
(A6) extending the 3' end of the folding sequence in the single-stranded template nucleic acid using the primer-extended strand that has been rendered single-stranded in the step (A4) as a template.

In the first nucleic acid synthesis method of the present invention, the step (A3) and the step (A4) may be repeated to a total of two or more times.

In the first nucleic acid synthesis method of the present invention, the single-stranded template nucleic acid provided in the step (A1) may be a single-stranded template nucleic acid formed by an isothermal amplification reaction using the primer set of the present invention in which only the first primer includes the folding sequence (D-D') on the 5' side of the sequence (C), and the primer hybridized to the loop in the step (A2) may be the first primer including the folding sequence (D-D').

The first nucleic acid synthesis method of the present invention may be configured so that the single-stranded template nucleic acid provided in the step (A1) further includes a folding sequence including, on the same strand, two sequences that hybridize to each other and being linked to the 5' end of the 5' side stem-loop sequence, and the first nucleic acid synthesis method includes, instead of the step (A3), the following step (A3-2): (A3-2) successively continuing the extension of the primer that has reached the 5' end of the 5' side stem sequence from the 5' end of the 5' side stem sequence directly to the 3' end of the folding sequence, without mediation of the folding sequence linked to the 5' end of the 5' side stem sequence.

In the first nucleic acid synthesis method of the present invention, the step (A3-2) and the step (A4) may be repeated to a total of two or more times.

In the case where the first nucleic acid synthesis method of the present invention includes the step (A3-2) instead of the step (A3), the single-stranded template nucleic acid provided in the step (A1) may be a single-stranded template nucleic acid formed by an isothermal amplification method using the primer set of the present invention that includes the first primer including the folding sequence (D-D') and the second primer including the folding sequence (E-E'), and the primer hybridized to the loop in the step (A2) may be the first primer or the second primer of the primer set according to the present invention.

Still another aspect of the present invention may be a first nucleic acid amplification method including the step of: isothermally synthesizing a double-stranded nucleic acid composed of a single-stranded nucleic acid in which the order of at least two different sequences is repeated to a total of two or more times and a nucleic acid complementary to the single-stranded nucleic acid, wherein the step of synthesizing the nucleic acid is carried out by the first nucleic acid synthesis method of the present invention.

Yet another aspect of the present invention may be a second nucleic acid synthesis method for isothermally synthesizing a double-stranded nucleic acid composed of a single-stranded nucleic acid in which the order of at least two different sequences is repeated to a total of two or more times and a nucleic acid complementary to the single-stranded nucleic acid, including at least one of a first reaction step; and a second reaction step. The first reaction step includes the following steps (B1) to (B3):
(B1) providing two double strands in a state where their sequences are in opposite orientations, the double strands each being composed of a single-stranded nucleic acid that includes, in a region including the 3' end, a folding sequence including, on the same strand, two sequences that hybridize to each other and a single-stranded nucleic acid complementary to the single-stranded nucleic acid;
(B2) extending, through a strand displacement reaction, the 3' end of the folding sequence in the single-stranded nucleic acid in one of the two double strands provided in the step (B1) using the complementary single-stranded nucleic acid in the other double strand as a template, thereby forming a partial double strand in which part of the extended strand of the single-stranded nucleic acid in the above-described one of the double strands hybridizes to the complementary single-stranded nucleic acid in the other double strand; and
(B3) extending, in the partial double strand in the step (B2), the 3' end of the complementary single-stranded nucleic acid using the single-stranded nucleic acid as a template, thereby forming a complete double strand.

The second reaction step includes the following steps (C1) to (C3);
(C1) providing one double strand composed of a single-stranded nucleic acid that includes, in a region including the 3' end, a folding sequence including, on the same strand, two sequences that hybridize to each other and a single-stranded nucleic acid complementary to the single-stranded nucleic acid;
(C2) extending, through a strand displacement reaction, the 3' end of the folding sequence in the single-stranded nucleic acid in the double strand provided in the step (C1) using the complementary single-stranded nucleic acid as a template from the 3' end to the 5' end of the complementary single-stranded nucleic acid, thereby forming a partial double strand in which part of the extended strand of the single-stranded nucleic acid hybridizes to the complementary single-stranded nucleic acid; and
(C3) extending, in the partial double strand in the step (C2), the 3' end of the complementary single-stranded nucleic acid using the single-stranded nucleic acid as a template, thereby forming a complete double strand.

Each double strand in the steps (B1) and (C1) may be a double strand formed by an isothermal amplification reaction using the primer set in which at least one of the first primer and the second primer further includes, on the 5' side of the sequence (C), a folding sequence (D-D') including, on the same strand, two sequences that hybridize to each other. Alternatively, each double strand in the steps (B1) and (C1) may be a double strand formed by an isothermal amplification reaction using the primer set in which the first primer further includes, on the 5' side of the sequence (C), a folding sequence (D-D') including, on the same strand, two sequences that hybridize to each other, the second primer further includes, on the 5' side of the sequence (C), a folding sequence (E-E') including, on the same strand, two sequences that hybridize to each other, and the sequence (D-D') and the sequence (E-E') are different from each other.

Yet another aspect of the present invention may be a second nucleic acid amplification method for amplifying a nucleic acid, including the step of isothermally synthesizing a double-stranded nucleic acid composed of a single-stranded nucleic acid in which the order of at least two different sequences is repeated to a total of two or more times and a nucleic acid complementary to the single-stranded nucleic acid, wherein the step of synthesizing the nucleic acid is carried out by the second nucleic acid synthesis method of the present invention.

Next, the present invention will be described in detail with reference to illustrative examples.

In the present invention, the term "target nucleic acid" or "target nucleic acid sequence" not only means a nucleic acid to be amplified or a sequence thereof itself, but also means a sequence complementary thereto and a nucleic acid having the complementary sequence.

In the present invention, the expression "hybridizes to (and grammatical variations thereof)" means that, under stringent conditions, part of the primer of the present invention hybridizes to a target nucleic acid and does not hybridize to any nucleic acid molecule other than the target nucleic acid. The stringent conditions can be determined depending on, e.g., the melting temperature Tm (° C.) of a double strand composed of the primer of the present invention and a complementary strand thereto, the salt concentration in a hybridization solution, etc., regarding which J. Sambrook, E. F. Frisch, T. Maniatis; Molecular Cloning 2nd edition, Cold Spring Harbor Laboratory (1989) etc. can be referenced, for example. For example, when hybridization is caused at a temperature slightly lower than the melting temperature of the primer to be used, the primer can be hybridized specifically to a target nucleic acid. Such a primer can be designed using commercially available primer construction software such as, for example, Primer3 (Whitehead Institute for Biomedical Research). According to preferable embodiments of the present invention, the primer that hybridizes to a certain target nucleic acid includes the whole or part of the sequence of a nucleic acid molecule that is complementary to the target nucleic acid.

FIG. 1 shows an example of the primer set according to the present invention. As shown in FIG. 1, the primer set of this example is a primer set for use in a method for isothermally amplifying a target nucleic acid sequence 4. The primer set includes a first primer 1F and a second primer 1R. The first primer 1F includes, on the 3' side thereof, a sequence (A') that can hybridize to a sequence (A) on the 3' side of the target nucleic acid sequence. The second primer 1R includes, on the 3' side thereof, a sequence (B') that can hybridize to a sequence (B) on the 3' side of either a strand extended from the first primer or a complementary strand of the target nucleic acid sequence 4. Furthermore, the first primer 1F and the second primer 1R include, on the 5' sides thereof, sequences (C) that are identical to each other.

Figure 4:
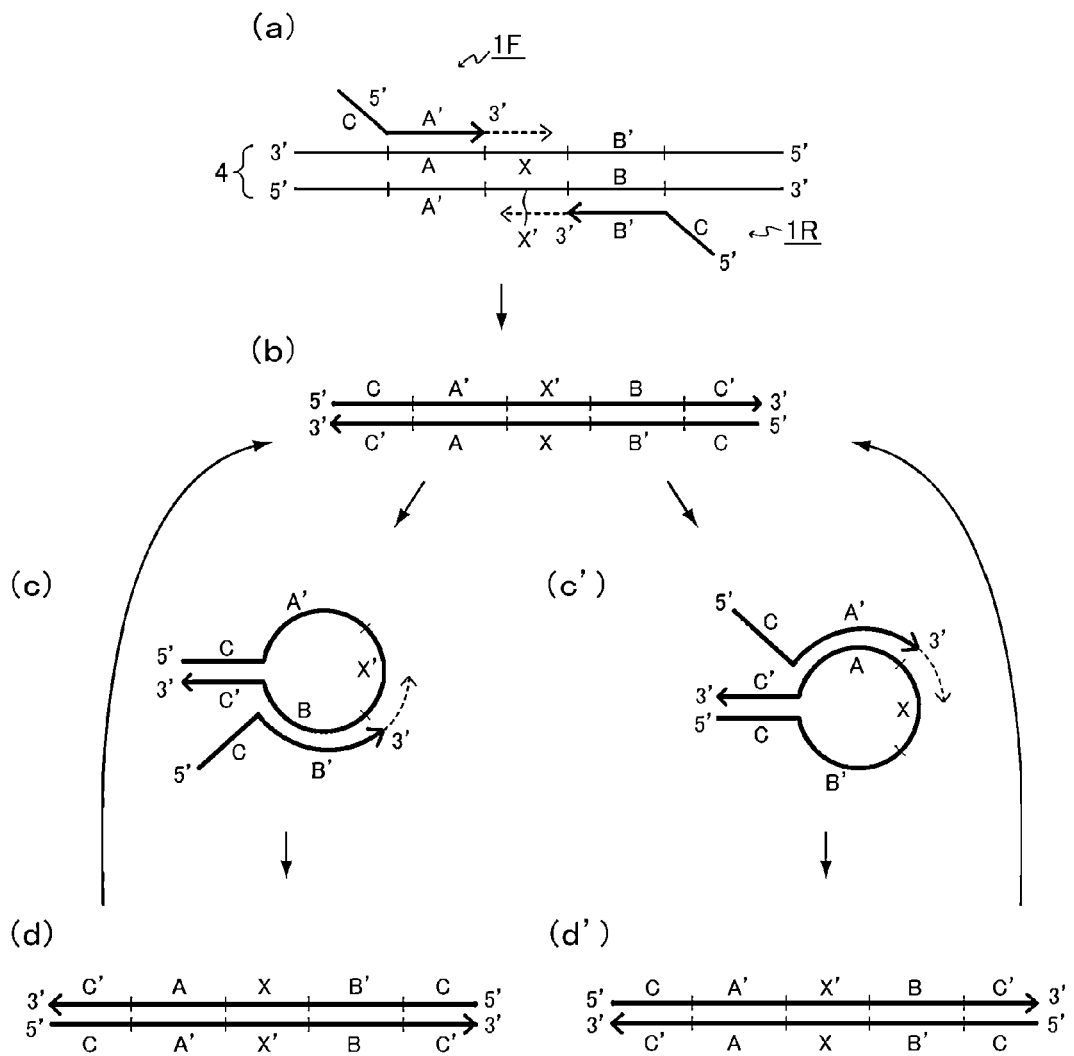
FIG. 4 is a schematic view showing an example of an amplification reaction using the primer set according to the present invention.

FIG. 4 is a schematic view showing an example of an amplification reaction using the primer set of this example. In FIG. 4, components and parts identical to those in FIG. 1 are given the same reference numerals.

As shown in (a) in FIG. 4, the first primer 1F and the second primer 1R hybridize to the target nucleic acid sequence 4, and extension reaction of the primers occurs. Then, as shown in (b) in FIG. 4, the second primer hybridizes to the extended strand of the first primer and is extended, or alternatively, the first primer hybridizes to the extended strand of the second primer and is extended, whereby a double-stranded intermediate is formed. As shown in (c) and (c') in FIG. 4, when the double-stranded intermediate is rendered single-stranded by dynamic equilibrium reaction, the intermediate forms a stem-loop structure by intermolecular hybridization. Then, the first primer or the second primer hybridizes to the loop of the single-stranded intermediate having the stem-loop structure and forms an extended strand, whereby the double-stranded intermediate as shown in (d) or (d') in FIG. 4 is formed. Because the double-stranded intermediates shown in (d) and (d') in FIG. 4 are the same as the double-stranded intermediate shown in (b) in FIG. 4, they become a single-stranded intermediate having a stem-loop structure again by dynamic equilibrium reaction. By this series of cycles, the target nucleic acid sequence is amplified.

In the first primer and the second primer of the primer set according to the present invention, the number of bases in each of the sequences (A') and (B') that hybridize to the target nucleic acid sequence is not particularly limited, and is, for example, 3 to 100, preferably 10 to 60, and more preferably 15 to 50. Also, the number of bases in the identical sequence (C) in each of the first primer and the second primer of the primer set of the present invention is not particularly limited, and is, for example, 3 to 100, preferably 10 to 60, and more preferably 15 to 50.

Figure 2:
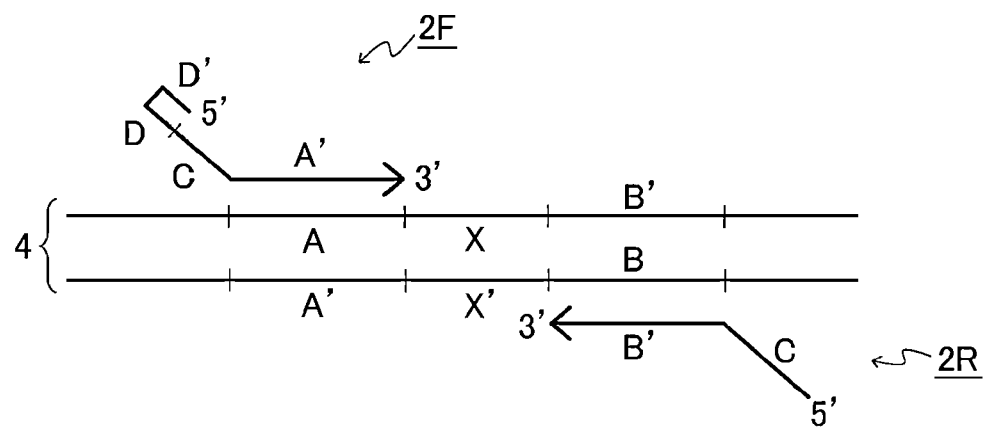
FIG. 2 shows another example of the primer set according to the present invention.

FIG. 2 shows an example of the primer set of the present invention in which a first primer 2F further includes, on the 5' side of the sequence (C), a folding sequence (D-D') including, on the same strand, two sequences that hybridize to each other.

In the present invention, the full length of the folding sequence (D-D') is not particularly limited, and is, for example, 3 to 100 bases, preferably 4 to 60 bases, and more preferably 5 to 50 bases. The number of bases in either one of the sequences complementary to each other in the folding sequence (D-D') is not particularly limited, and is, for example, 1 to 50 bases, preferably 1 to 30 bases, and more preferably 1 to 20 bases. Between the sequences complementary to each other in the folding sequence (D-D'), an intervening sequence may be present. The number of bases in the intervening sequence is, for example, 1 to 50, preferably 1 to 20, and more preferably 1 to 10. Furthermore, in the present invention, part of the folding sequences may form part of the identical sequences (C) of the first primer and the second primer. The above-described conditions for the folding sequence (D-D') also are applicable to the folding sequence (E-E') different from the folding sequence (D-D').

Figure 3:
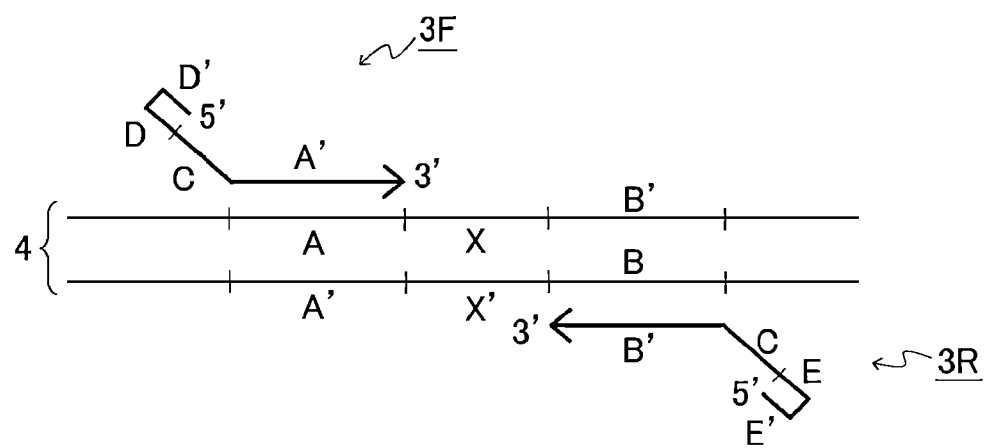
FIG. 3 shows still another example of the primer set according to the present invention.

FIG. 3 shows an embodiment of the primer set of the present invention in which a first primer 3F further includes, on the 5' side of the sequence (C), a folding sequence (D-D') including, on the same strand, two sequences that hybridize to each other, a second primer 3R further includes, on the 5' side of the sequence (C), a folding sequence (E-E') including, on the same strand, two sequences that hybridize to each other, and the sequence (D-D') and the sequence (E-E') are different from each other.

Next, the nucleic acid synthesis method according to the present invention will be described in detail with reference to an illustrative example.

As described in examples to be described below, in the nucleic acid synthesis method according to the present invention, a double-stranded nucleic acid composed of a single-stranded nucleic acid in which the order of at least two different sequences is repeated to a total of two or more times and a nucleic acid complementary to the single-stranded nucleic acid is synthesized isothermally. Examples of the reaction mechanism of this nucleic acid synthesis method according to the present invention include: a first synthesis reaction to be described below with reference to FIGS. 5A to 7B; and a second synthesis reaction to be described below with reference to FIGS. 8A to 9C. The first synthesis reaction includes the steps (A1) to (A6). Alternatively, as described above, the first synthesis reaction may include the step (A3-2) instead of the step (A3). The second synthesis reaction includes at least one of a first reaction step including the steps (B1) to (B3); and a second reaction step including the steps (C1) to (C3). It is to be noted that an amplification reaction using the primer set according to the present invention also may include a synthesis reaction(s) other than the first synthesis reaction and the second synthesis reaction. Although it is preferable that an amplification reaction using the primer set of the present invention includes at least one of the first synthesis reaction and second synthesis reaction, the amplification reaction may not include either the first synthesis reaction or the second synthesis reaction.

First, the first synthesis reaction is an extended strand exchange reaction based on nick-passing over-type extension. An example of the first synthesis reaction will be described below with reference to FIGS. 5A to 7B.

Figure 5A:
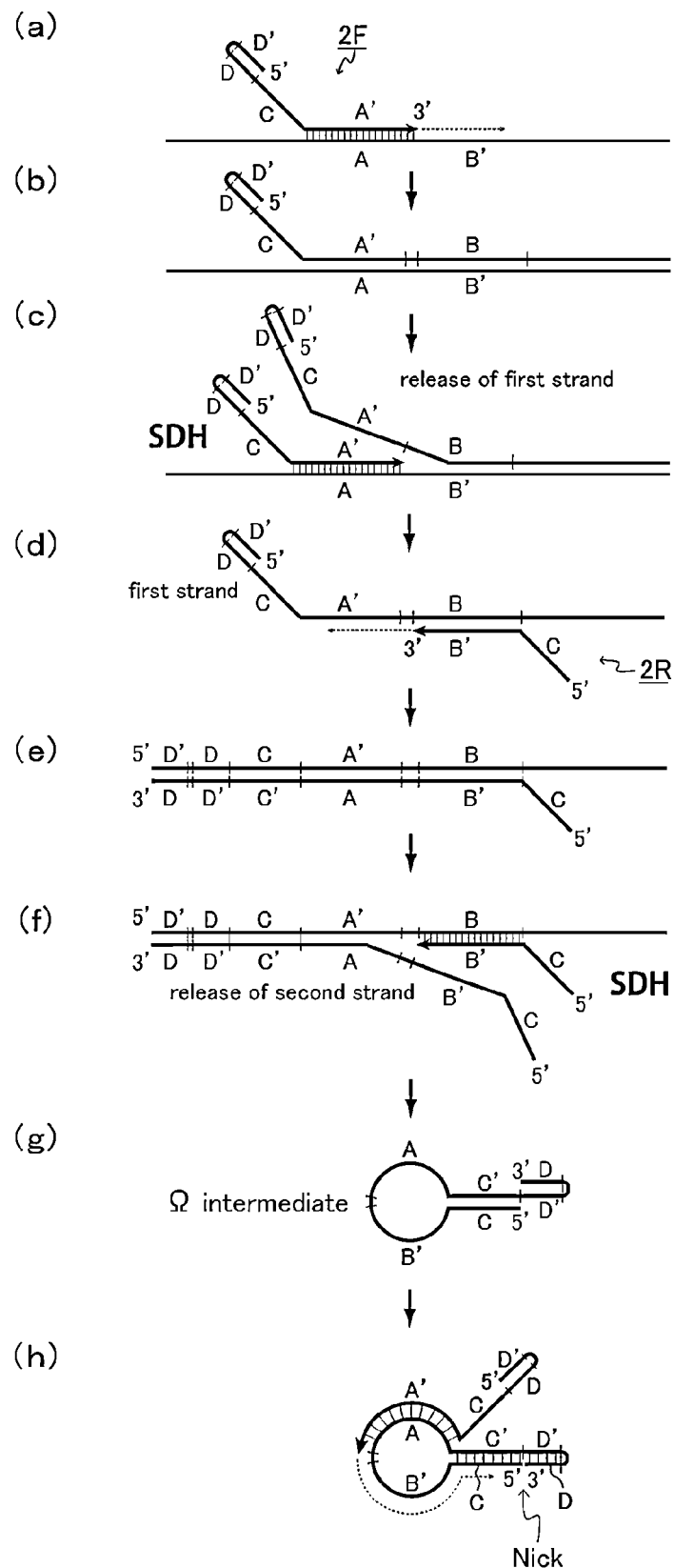
FIG. 5A is a schematic view showing an example of a reaction mechanism in the nucleic acid synthesis method according to the present invention.
Figure 5B:
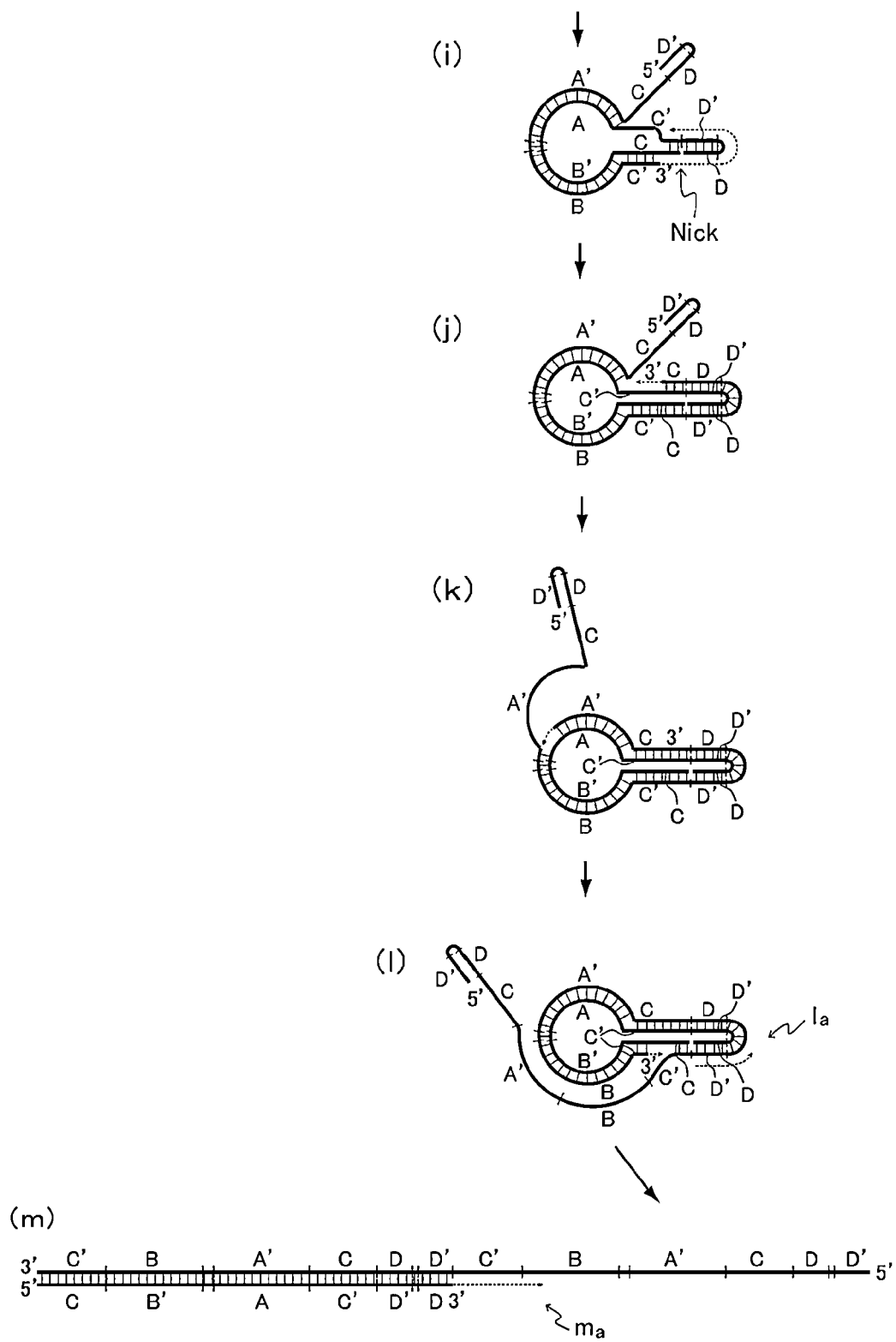
FIG. 5B is a schematic view showing an example of a reaction mechanism in reaction steps subsequent to those shown in FIG. 5A.

FIGS. 5A and 5B illustrate an example of the first synthesis reaction. This is a reaction caused using the same primer set as shown in FIG. 2, namely, a primer set in which only one of the primers includes a folding sequence. More specifically, the primer set includes a first primer 2F including a folding sequence (D-D') on the 5' side of a sequence (C) and a second primer 2R without a folding sequence. In FIGS. 5A and 5B, components and parts identical to those in FIG. 2 are given the same reference numerals.

First, as shown in (a) to (g) in FIG. 5A, an Ω intermediate is provided (the step (A1)). As shown in (g) in FIG. 5A, this Ω intermediate is a single-stranded template nucleic acid having a stem-loop structure in which a 3' side stem sequence (C') including the 3' end and the 5' side stem sequence (C) including the 5' end are linked to each other via a loop sequence (A-B'), with the folding sequence (D-D') including, on the same strand, two sequences (D') and (D) that hybridize to each other being linked to the 3' end of the 3' side stem sequence (C').

The step (A1) ((a) to (g) in FIG. 5A) will be described specifically. First, as shown in (a) in FIG. 5A, the first primer 2F hybridizes to a sequence (A) of a target nucleic acid sequence. Further, as shown in (b) in FIG. 5A, the first primer 2F is extended, whereby extension of a first strand occurs. Next, as shown in (c) in FIG. 5A, the sequence (A') of the extended strand of the first primer 2F is released from the sequence (A) of the target nucleic acid sequence owing to fluctuations in binding. Then, a primer having the same sequence as the first primer 2F hybridizes to the sequence (A) of the target nucleic acid sequence by strand displacement hybridization (SDH) and is further extended, thereby releasing the extended strand (first strand) of the first primer 2F.

Next, as shown in (d) and (e) in FIG. 5A, the second primer 2R hybridizes to the released first strand and is extended. Thus, an extended strand (second strand) of the second primer 2R is formed. As shown in (e) in FIG. 5A, the second strand includes a sequence (D-D'-C'-A) complementary to a sequence (A'-C-D-D') of the first primer. Furthermore, as shown in (f) in FIG. 5A, the sequence (B') of the extended strand of the second primer 2R is released from the sequence (B) of the target nucleic acid sequence owing to fluctuations in binding. Then, a primer having the same sequence as the second primer 2R hybridizes to the sequence (B) of the first strand by strand displacement hybridization (SDH) and is further extended, thereby releasing the second strand. Then, as shown in (g) in FIG. 5A, self-hybridization of the sequences (C) and (C') of the released second strand occurs, whereby a single-stranded template nucleic acid having an Ω-like structure is formed. This corresponds to the above-described Ω intermediate. The release of the primer-extended strands in (c) and (f) in FIG. 5A also may be achieved with the use of an outer primer (OP).

Next, as shown in (h) in FIG. 5A to (i) in FIG. 5B, a primer having the same sequence as the first primer 2F is hybridized to the sequence (A) in the loop of the Ω intermediate (single-stranded template nucleic acid), and the primer is extended toward the 5' end of the 5' side stem sequence (C) of the Ω intermediate (the step (A2)). When the primer is extended to the 5' side stem sequence (C), an extension reaction with the 5' side stem sequence (C) as a template occurs accompanying a strand displacement reaction, as shown in (i) in FIG. 5B. In the case where the extension terminates at a nick formed between the 5' end of the 5' side stem sequence (C) (tail sequence) and the 3' end of the folding (hook) sequence (D-D'), a haploid amplicon (the single-stranded template nucleic acid) is formed. The following description is directed to the case where the extension does not terminate at the nick, and an extended strand exchange reaction based on nick-passing over-type extension occurs.

First, as indicated with the dotted arrow in (i) in FIG. 5B, the extension of the primer that has reached the 5' end of the 5' side stem sequence (C) is continued successively from the 5' end of the 5' side stem sequence (C) to the 3' end of the folding sequence (D-D') (the step (A3)). Then, as shown in (j) to (l) in FIG. 5B, the extension of the primer that has reached the 3' end of the folding sequence (D-D') in (i) in FIG. 5B (the step (A3)) is continued successively toward the 5' end of the 5' side stem sequence (C) again, and, by the continuing primer extension, the primer-extended strand hybridizing to the single-stranded template nucleic acid (Ω intermediate) formed in the process from (h) in FIG. 5A to (i) in FIG. 5B (the step (A2)) is rendered single-stranded through a strand displacement reaction (the step (A4)). Then, the extension of the primer in the step (A4) is terminated at the 5' end of the 5' side stem sequence (C) shown in (l) in FIG. 5B (the step (A5)). As a result, the extended strand of the primer is rendered a (tandem) diploid 1a composed of the two amplicon sequences (the single-stranded template nucleic acid sequences) linked to each other in the forward direction. Furthermore, as shown in (m) in FIG. 5B, with the primer-extended strand that has been rendered single-stranded (the tandem diploid 1a) in the step (A4) as a template, the 3' end of the folding sequence (D-D') of the single-stranded template nucleic acid (the Ω intermediate) is extended (the step (A6)). By this extension reaction, a strand complementary to the primer-extended strand (the tandem diploid 1a) is formed. Thus, a complete double strand ma composed of the primer-extended strand and the complementary strand thereto is formed.

FIGS. 5A and 5B are directed to an example where the tandem diploid is formed by performing the steps (A3) and (A4) only once. On the other hand, it is also possible to form a tandem strand of triploid or higher polyploid by carrying out the same procedure except that the steps (A3) and (A4) are repeated to a total of two or more times. More specifically, the tandem strand of triploid or higher polyploid may be formed in the following manner: after the step (A4), the step (A3) is performed again, and after repeating the step (A3) and the step (A4) to a total of two or more times, the step (A5) and the step (A6) are then performed.

Figure 6A:
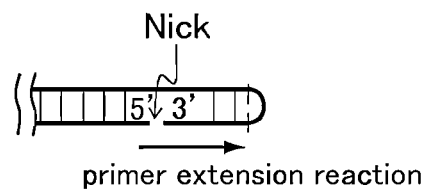
FIG. 6 shows schematic views illustrating an example of a reaction mechanism of an extended strand exchange reaction based on nick-passing over-type extension.
Figure 6B:
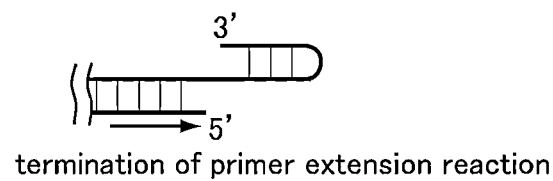

FIGS. 6A and 6B illustrate the case where a nick-passing over reaction occurs and the case where a nick-passing over reaction does not occur, respectively. First, as shown in FIG. 6A, when the 5' end of a 5' side stem sequence and the 3' end of a folding sequence are in close proximity in an Ω intermediate to form a nick therebetween, a primer extension reaction occurs passing over the nick. In contrast, as shown in FIG. 6B, when the 5' end of the 5' side stem sequence and the 3' end of the folding sequence are apart from each other in the Ω intermediate so that no nick is formed, a primer extension reaction terminates at the 5' end of the 5' side stem sequence.

Figure 7A:
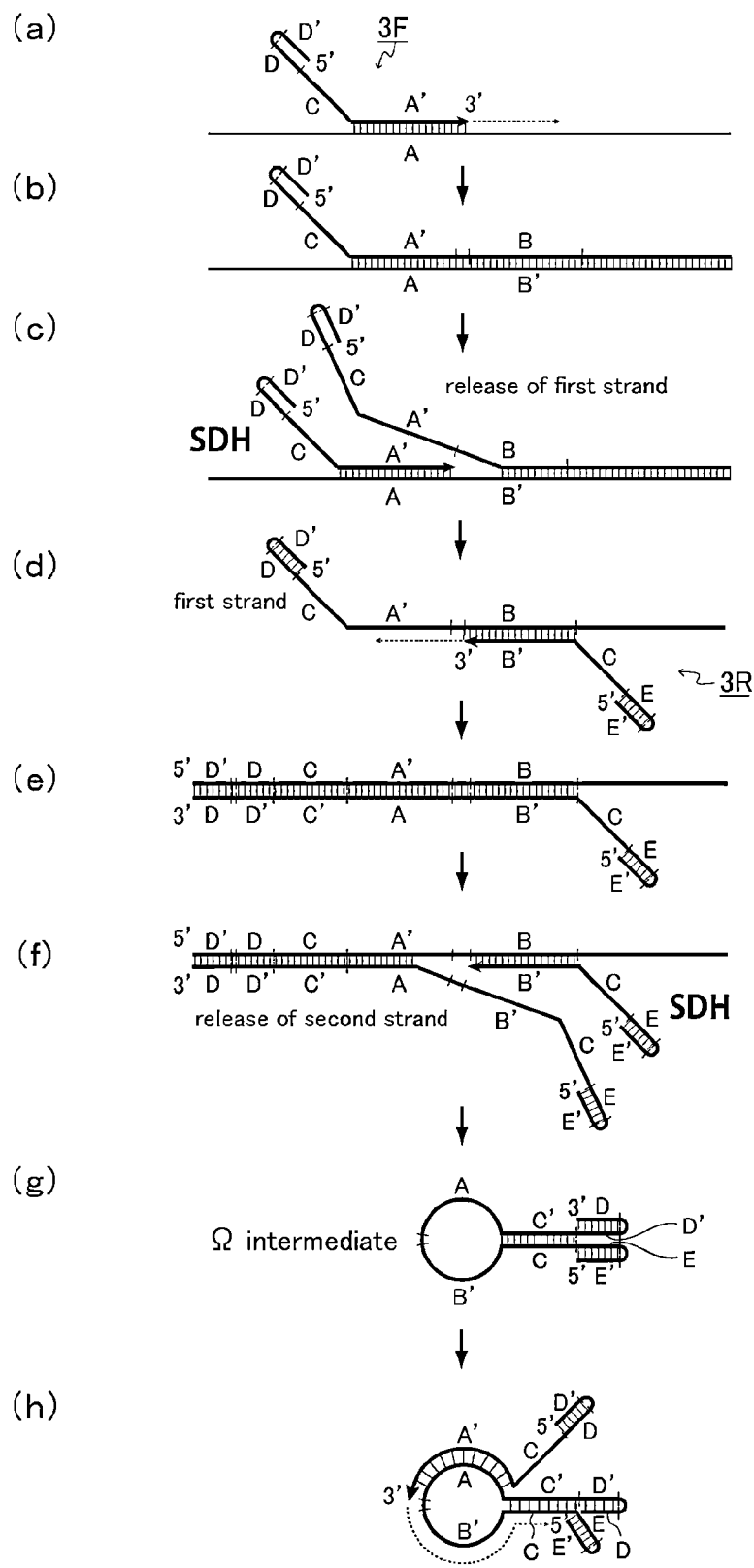
FIG. 7A is a schematic view showing another example of the reaction mechanism in the nucleic acid synthesis method according to the present invention.
Figure 7B:
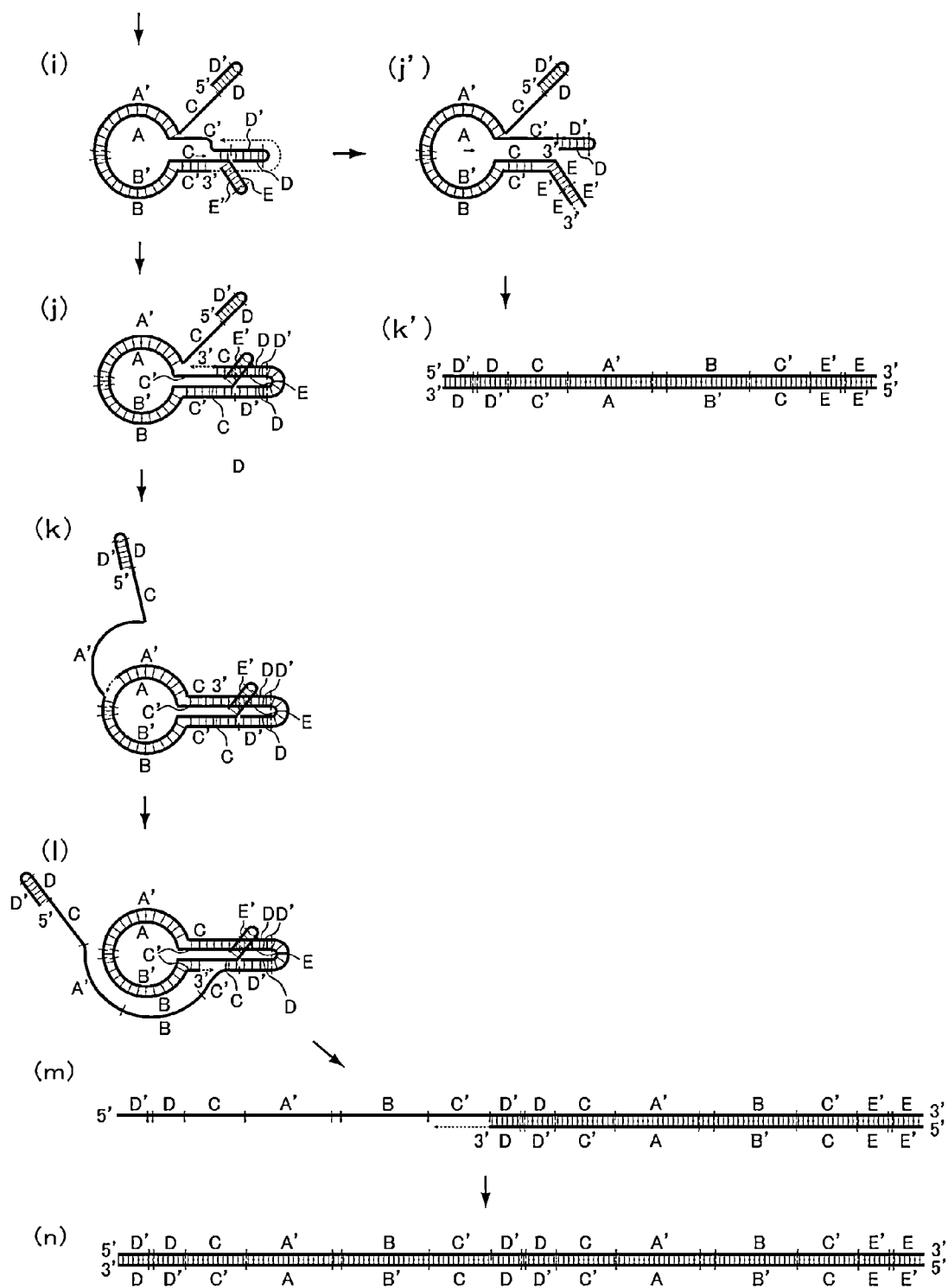
FIG. 7B is a schematic view showing an example of a reaction mechanism in reaction steps subsequent to those shown in FIG. 7A.

Next, FIGS. 7A and 7B show another example of the first synthesis reaction. This is a reaction caused using the same primer set as shown in FIG. 3, namely, a primer set in which both the primers include folding sequences, respectively. More specifically, the primer set includes a first primer 3F including a folding sequence (D-D') on the 5' side of a sequence (C) and a second primer 3R including a folding sequence (E-E') on the 5' side of a sequence (C). In FIGS. 7A and 7B, components and parts identical to those in FIG. 3 are given the same reference numerals.

First, as shown in (a) to (g) in FIG. 7A, an Ω intermediate is provided (the step (A1)). As shown in (g) in FIG. 7A, this Ω intermediate is a single-stranded template nucleic acid having a stem-loop structure in which a 3' side stem sequence (C') including the 3' end and the 5' side stem sequence (C) including the 5' end are linked to each other via a loop sequence (A-B'), with the folding sequence (D-D') including, on the same strand, two sequences (D') and (D) that hybridize to each other being linked to the 3' end of the 3' side stem sequence (C'). The Ω intermediate shown in (g) in FIG. 7A is different from the Ω intermediate shown in (g) in FIG. 5A in that the folding sequence (E-E') including, on the same strand, two sequences (E) and (E') that hybridize to each other is further linked to the 5' end of the 5' side stem sequence (C). The Ω intermediate shown in (g) in FIG. 7A is the same as the Ω intermediate shown in (g) in FIG. 5A, except that it includes the folding sequence (E-E').

In the step (A1) ((a) to (g) in FIG. 7A), (a) to (c) in FIG. 7A (hybridization of the first primer to a template nucleic acid, extension of the first primer, and the release of the extended strand of the first primer (the first strand)) are the same as (a) to (c) in FIG. 5A. The first primer 3F in FIG. 7A has the same sequence as the first primer 2F in FIG. 5A.

Next, as shown in (d) to (g) in FIG. 7A, a single-stranded template nucleic acid (Ω intermediate) shown in (g) in FIG. 7A is formed in the same manner as in (d) to (g) in FIG. 5A, except that the second primer 3R including the folding sequence (E-E') is used instead of the second primer 2R without a folding sequence.

Next, as shown in (h) in FIG. 7A to (i) in FIG. 7B, a primer having the same sequence as the first primer 3F is hybridized to the sequence (A) in the loop of the Ω intermediate (single-stranded template nucleic acid), and the primer is extended toward the 5' end of the 5' side stem sequence (C) of the Ω intermediate (the step (A2)). When the primer is extended to the 5' side stem sequence (C), an extension reaction with the 5' side stem sequence (C) as a template occurs accompanying a strand displacement reaction, as shown in (i) in FIG. 7B. Thereafter, as shown in (j') in FIG. 7B, when the primer is extended without interruption to the 5' end of the folding sequence (E'-E) of the Ω intermediate, a perfectly complementary amplicon double-stranded DNA is generated ((k') in FIG. 7B).

On the other hand, when a tandem amplicon sequence is to be formed, as indicated with the dotted arrow in (i) in FIG. 7B, the extension of the primer that has reached the 5' end of the 5' side stem sequence (C) is continued successively from the 5' end of the 5' side stem sequence (C) directly to the 3' end of the folding sequence (D-D'), without mediation of the folding sequence (E-E') linked to the 5' end of the 5' side stem sequence (C) (the step (A3-2), Nick-passing over step). In the nick-passing over step, for example, the primer may be extended from some midpoint in the 5' side stem sequence to the 3' end of the folding sequence. Alternatively, the primer may be extended from some midpoint in the folding sequence linked to the 5' end of the 5' side stem sequence or from the 5' end of the folding sequence to the 3' end of the folding sequence linked to the 3' side stem sequence. Then, as shown in (j) to (l) in FIG. 7B, the extension of the primer that has reached the 3' end of the folding sequence (D-D') in (i) in FIG. 7B (the step (A3-2)) is continued successively toward the 5' end of the 5' side stem sequence (C) again, and, by the continuing primer extension, the primer-extended strand hybridizing to the single-stranded template nucleic acid (Ω intermediate) formed in the process from (h) in FIG. 7A to (i) in FIG. 7B (the step (A2)) is rendered single-stranded through a strand displacement reaction (the step (A4)). Then, the extension of the primer in the step (A4) is terminated at the 5' end of the 5' side stem sequence (C) shown in (l) in FIG. 7B (the step (A5)). It is to be noted here that, although the reaction for rendering the primer-extended strand single-stranded through the strand displacement reaction terminates at the 5' end of the 5' side stem sequence (C), the extension reaction itself proceeds until the primer is extended beyond the 5' end of the 5' side stem sequence (C) to reach the 5' end of the folding sequence (E-E') of the Ω intermediate. As a result, the primer-extended strand becomes a (tandem) diploid composed of the two amplicon sequences linked to each other in the forward direction (the upper strand in (m) or (n) in FIG. 7B). Furthermore, as shown in (m) and (n) in FIG. 7B, using the primer-extended strand that has been rendered single-stranded in the step (A4) as a template, the 3' end of the folding sequence (D-D') of the single-stranded template nucleic acid (the Ω intermediate) is extended (the step (A6)). By this extension reaction, a strand complementary to the primer-extended strand (the lower strand in (n) in FIG. 7B) is formed. Thus, a complete double strand composed of the primer-extended strand and the complementary strand thereto is formed. The successive extension reactions of the primer from the 5' end of the 5' side stem to the 3' end of the folding sequence (D-D') occur according to the same mechanism as the above-described nick-passing over reaction.

FIGS. 7A and 7B are directed to an example where the tandem diploid is formed by performing the steps (A3-2) and (A4) only once. On the other hand, it is also possible to form a tandem strand of triploid or higher polyploid by carrying out the same procedure except that the steps (A3-2) and (A4) are repeated to a total of two or more times. More specifically, the tandem strand of triploid or higher polyploid may be formed in the following manner: after the step (A4), the step (A3-2) is performed again, and after repeating the step (A3-2) and the step (A4) to a total of two or more times, the step (A5) and the step (A6) are then performed.

Next, the second synthesis reaction will be described with reference to FIGS. 8A to 9C.

Figure 8A:
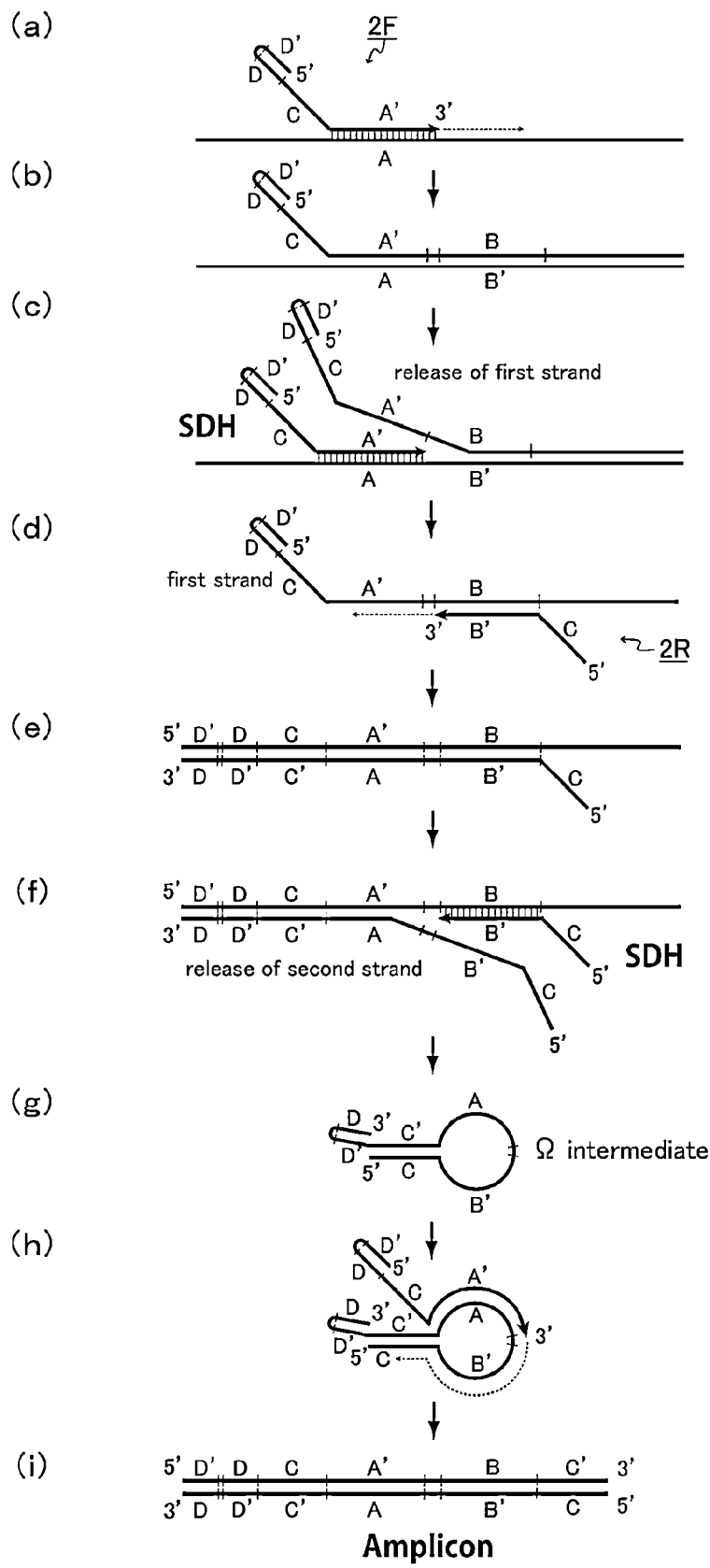
FIG. 8A is a schematic view showing still another example of the reaction mechanism in the nucleic acid synthesis method according to the present invention.
Figure 8B:
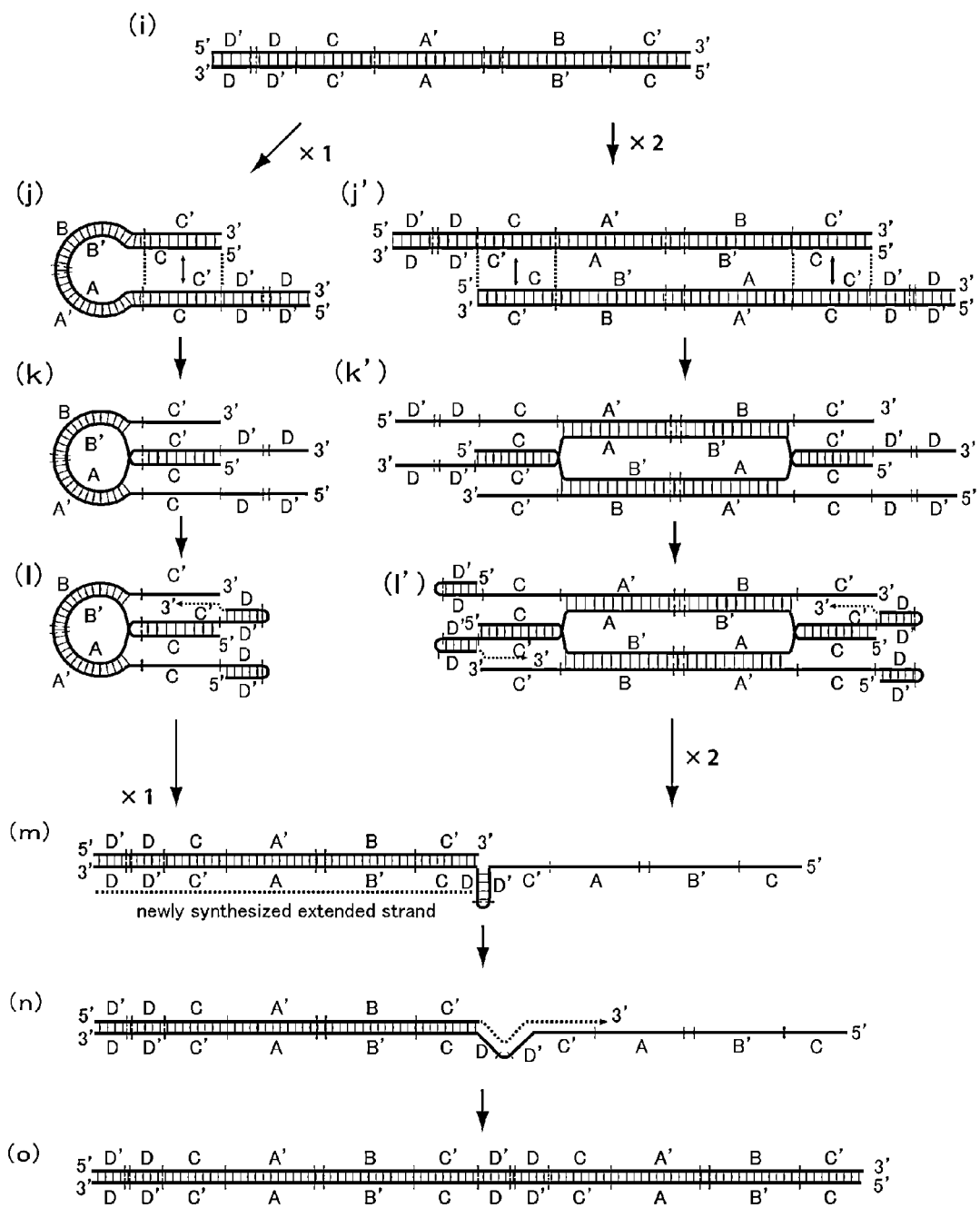
FIG. 8B is a schematic view showing an example of a reaction mechanism in reaction steps subsequent to those shown in FIG. 8A.

FIGS. 8A and 8B illustrate an example of the second synthesis reaction. This is a reaction caused using the same primer set as shown in FIG. 2, namely, a primer set in which only one of the primers includes a folding sequence. More specifically, the primer set includes a first primer 2F including a folding sequence (D-D') on the 5' side of a sequence (C) and a second primer 2R without a folding sequence. In FIGS. 8A and 8B, components and parts identical to those in FIG. 2 are given the same reference numerals.

First, a complementary double strand (haploid amplicon) is formed in (a) to (i) in FIG. 8A. One such complementary double strand is provided as shown in (j) in FIG. 8B (the step (C1)), or two such complementary double strands are provided in the state where their sequences are in opposite orientations as shown in (j') in FIG. 8B (the step (B1)). The process shown from (a) to (g) in FIG. 8A (formation of an Ω intermediate) is identical to the process shown from (a) to (g) in FIG. 5A (the first synthesis reaction). Next, as shown in (h) in FIG. 8A, a primer having the same sequence as the first primer 2F is hybridized to the sequence (A) in the loop of the Ω intermediate (single-stranded template nucleic acid), and the primer is extended toward the 5' end of the 5' side stem sequence (C) of the Ω intermediate. This extension reaction terminates at the 5' end of the 5' side stem sequence (C). As a result, as shown in (i) in FIG. 8A, a complementary double strand (haploid amplicon) composed of the Ω intermediate and the primer-extended strand is formed. As shown in (i) in FIG. 8A, this amplicon is a double strand composed of a single-stranded nucleic acid (the lower strand in (i) in FIG. 8A) including, in a region including the 3' end, a folding sequence (D-D') including, on the same strand, two sequences (D) and (D') that hybridize to each other and a single-stranded nucleic acid (the upper strand in (i) in FIG. 8A) complementary to the single-stranded nucleic acid. In the case where the second primer 2R provides a starting point of the reaction, an amplicon is formed through the same reaction process.

From the amplicon shown in (i) in FIG. 8A (the same as that shown in (i) in FIG. 8B), a (tandem) amplification product composed of the Ω intermediates linked to each other in the forward direction or a (tandem) amplification product composed of complementary strands to the Ω intermediates linked to each other in the forward direction is formed through two kinds of reaction pathways, as shown in FIG. 8B. One of the reaction pathways is such that, as shown in (j) to (l) in FIG. 8B, strand displacement hybridization occurs within the molecule of the double-stranded amplicon ((i) in FIG. 8B). The other reaction pathway is such that, as shown in (j') to (l') in FIG. 8B, strand displacement hybridization occurs between two molecules of the double-stranded amplicon. First, one amplicon is provided as shown in (j) in FIG. 8B (the step (C1)), or two amplicons are provided in the state where their sequences are in opposite orientations as shown in (j') in FIG. 8B (the step (B1)). Subsequently, either within the molecule of the double-stranded amplicon as shown in (j) to (k) in FIG. 8B or between two molecules of the amplicon as shown in (j') to (k') in FIG. 8B, a 5' end sequence (C) hybridizes to a sequence (C') of another strand (tail substitution). During this tail substitution, as shown in (l) and (l') in FIG. 8B, folding of the folding sequence (D-D') at each end occurs. As a result, recombinant extension occurs from the 3' end of the sequence D of the folding sequence (D-D') at the 3' end with the strand on the opposite side as a template. By this extension reaction, a newly synthesized extended strand is generated ((m) in FIG. 8B). The reaction illustrated from (l) to (m) in FIG. 8B corresponds to the step of extending, through a strand displacement reaction, the 3' end of the folding sequence (D-D') in the single-stranded nucleic acid in the double strand ((j) in FIG. 8B) provided in the step (C1) using the complementary single-stranded nucleic acid as a template from the 3' end to the 5' end of the complementary single-stranded nucleic acid, thereby forming a partial double strand ((m) in FIG. 8B) in which part of the extended strand of the single-stranded nucleic acid hybridizes to the complementary single-stranded nucleic acid (the step (C2)). The reaction illustrated from (l') to (m) in FIG. 8B corresponds to the step of extending, through a strand displacement reaction, the 3' end of the folding sequence (D-D') in the single-stranded nucleic acid in one of the two double strands ((j') in FIG. 8B) provided in the step (B1) using the complementary single-stranded nucleic acid in the other double strand as a template, thereby forming a partial double strand ((m) in FIG. 8B) in which part of the extended strand of the single-stranded nucleic acid in the above-described one of the double strands hybridizes to the complementary single-stranded nucleic acid in the other double strand (the step (B2)). It is to be noted here that these extension reactions are not Switchback extension occurring from the folding sequence (D-D') at the 3' end using, as a template, a sequence of the strand in which the folding sequence is included itself.

Furthermore, as shown in (n) in FIG. 8B, an extension reaction occurs from the 3' end of a strand complementary to the newly synthesized extended strand with the strand on the opposite side as a template. As a result, a (tandem) double strand in which the above-described amplicons are linked to each other in the forward direction is formed ((o) in FIG. 8B). The reaction illustrated from (n) to (o) in FIG. 8B corresponds to the step of extending, in the partial double strand ((m) in FIG. 8B) in the step (B2) or (C2), the 3' end of the complementary single-stranded nucleic acid (the upper strand in (m) in FIG. 8B) using the single-stranded nucleic acid as a template (this extension reaction is shown in (n) in FIG. 8B), thereby forming a complete double strand ((o) in FIG. 8B) (the step (B3) or (C3)).

Figure 9A:
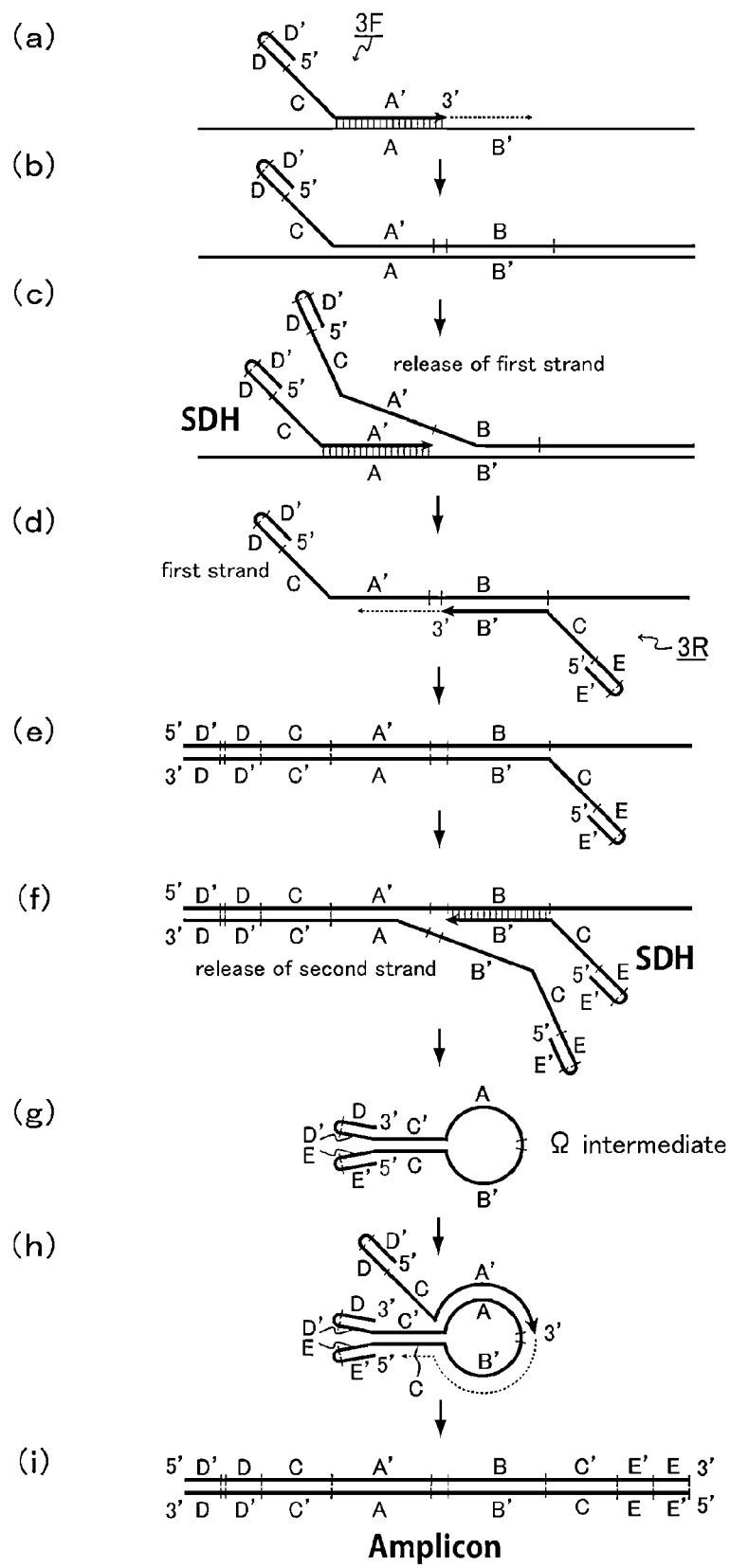
FIG. 9A is a schematic view showing yet another example of the reaction mechanism in the nucleic acid synthesis method according to the present invention.
Figure 9B:
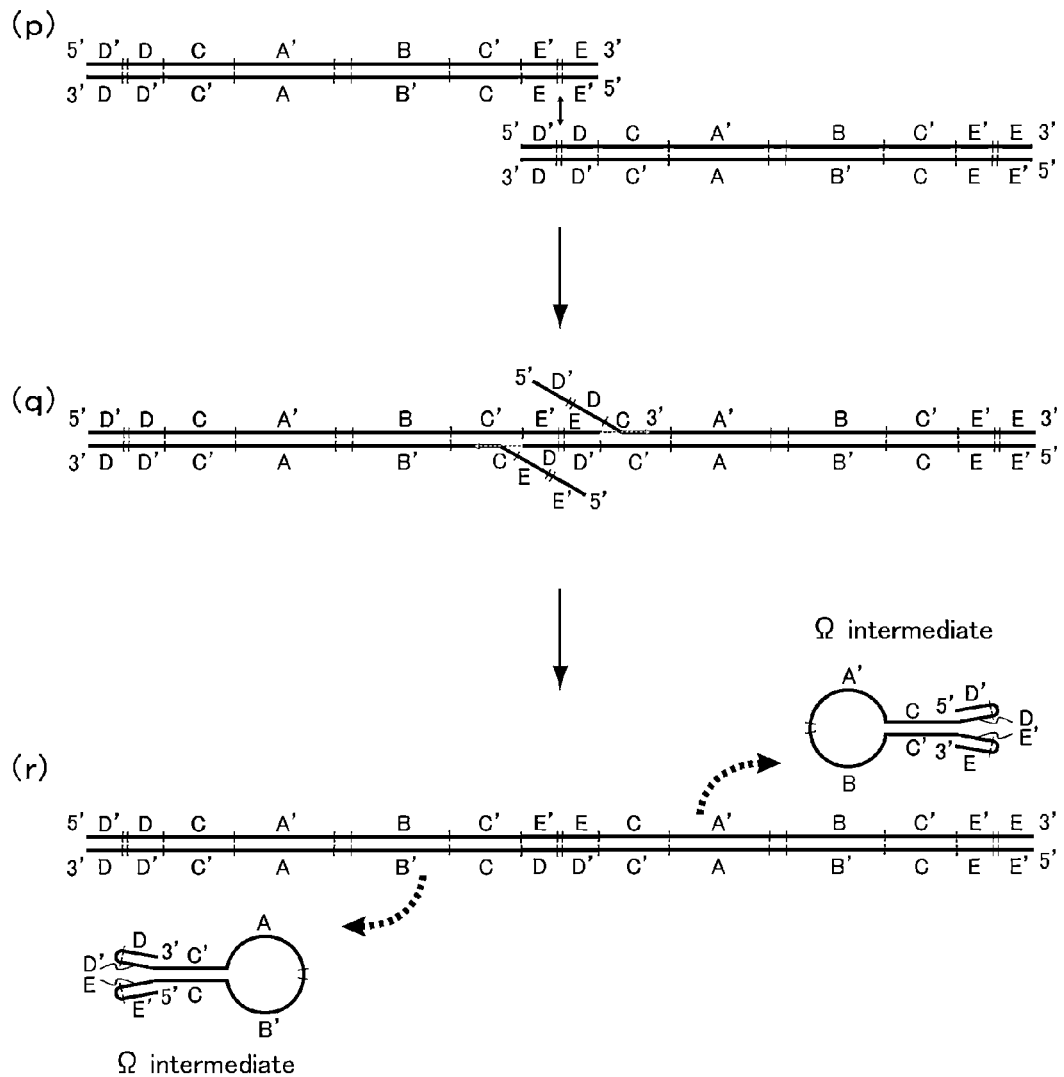
FIG. 9B is a schematic view showing an example of a reaction mechanism in reaction steps subsequent to those shown in FIG. 9A.
Figure 9C:
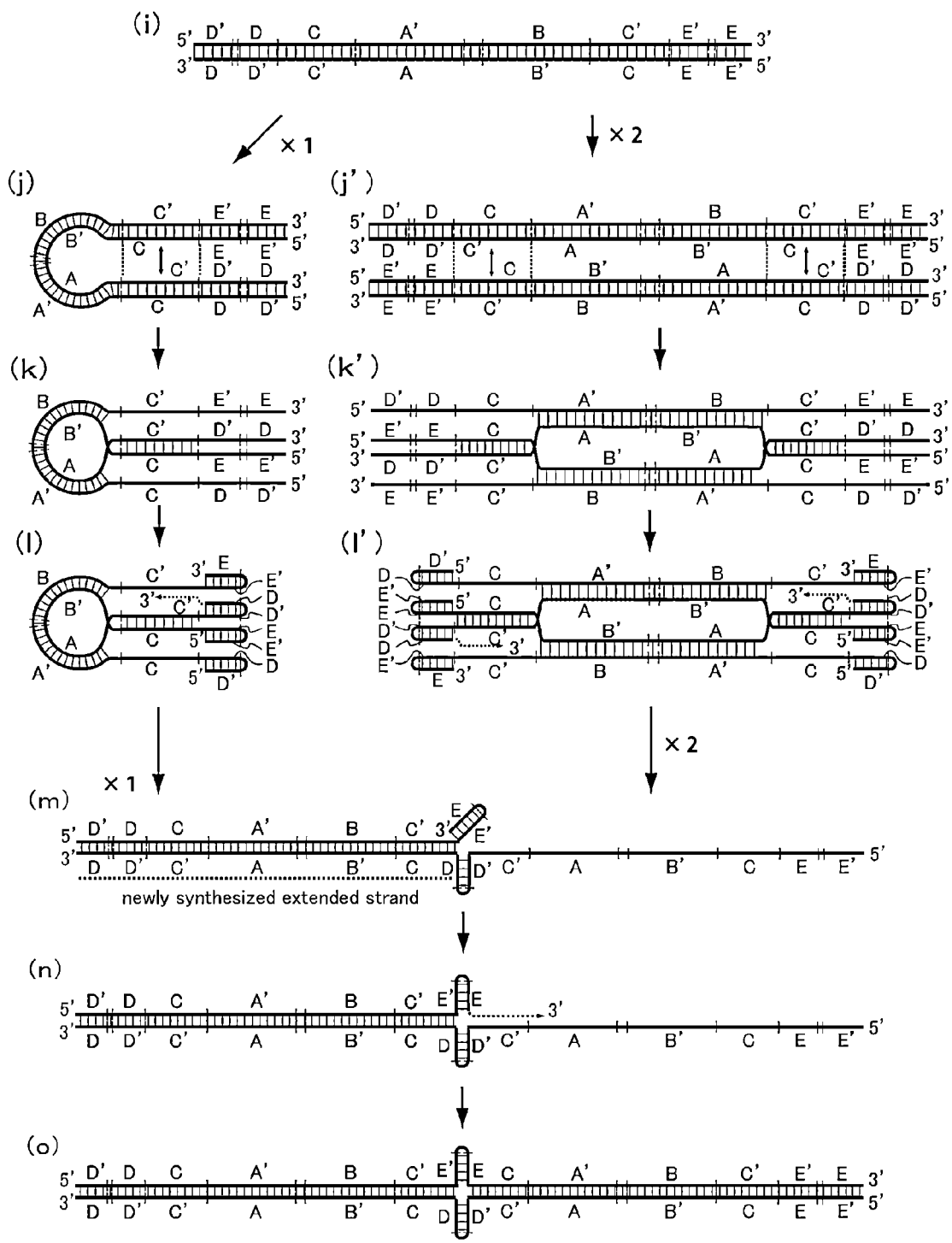
FIG. 9C is a schematic view showing another example of the reaction mechanism in the reaction steps subsequent to those shown in FIG. 9A.

Next, FIGS. 9A to 9C show another example of the second synthesis reaction. This is a reaction caused using the same primer set as shown in FIG. 3, namely, a primer set in which both the primers include folding sequences, respectively. More specifically, the primer set includes a first primer 3F including a folding sequence (D-D') on the 5' side of a sequence (C) and a second primer 3R including a folding sequence (E-E') on the 5' side of a sequence (C). In FIGS. 9A and 9B, components and parts identical to those in FIG. 3 are given the same reference numerals.

First, a complementary double strand (haploid amplicon) is formed in (a) to (i) in FIG. 9A. One such complementary double strand is provided as shown in (j) in FIG. 9C (the step (C1)), or two such complementary double strands are provided in the state where their sequences are in opposite orientations as shown in (j') in FIG. 9C (the step (B1)). The process shown from (a) to (g) in FIG. 9A (formation of an Ω intermediate) is identical to the process shown from (a) to (g) in FIG. 7A (the first synthesis reaction). Next, as shown in (h) in FIG. 9A, a primer having the same sequence as the first primer 3F is hybridized to the sequence (A) in the loop of the Ω intermediate (single-stranded template nucleic acid), and the primer is extended toward the 5' end of the 5' side stem sequence (C) of the Ω intermediate. This extension reaction terminates at the 5' end of the folding sequence (E-E') linked to the 5' side stem sequence (C). As a result, as shown in (i) in FIG. 9A, a complementary double strand (haploid amplicon) composed of the Ω intermediate and the primer-extended strand is formed. As shown in (i) in FIG. 9A, this amplicon is a double strand composed of a single-stranded nucleic acid (the lower strand in (i) in FIG. 9A) including, in a region including the 3' end, a folding sequence (D-D') including, on the same strand, two sequences (D) and (D') that hybridize to each other, and a single-stranded nucleic acid (the upper strand in (i) in FIG. 9A) complementary to the single-stranded nucleic acid. In the case where a second primer 3R provides a starting point of the reaction, an amplicon is formed through the same reaction process.

Subsequent to (i) in FIG. 9A, two kinds of reaction pathways shown in FIGS. 9B and 9C are possible. One of the reaction pathways is a reaction pathway in which folding sequences having similar palindromic sequences are used, as shown in FIG. 9B. More specifically, this is a reaction pathway in the case where the folding sequences (D-D') and (E-E') of the double-stranded amplicon shown in (i) in FIG.

9A are similar palindromic sequences. First, as shown in the additional illustration (p) in FIG. 9B, between two molecules of the double-stranded amplicon, the heterologous folding sequences (D-D') and (E-E') having the similar palindromic sequences hybridize to each other. Only in the case where the folding sequences each having the 3' end hybridize to each other as described above, the reaction does proceed to a subsequent stage ((q) in FIG. 9B). Next, as shown in (q) to (r) in FIG. 9B, a strand displacement extension reaction occurs with the 3' ends of the folding sequences hybridizing to each other as starting points. As a result, as shown in (r) in FIG. 9B, (tandem) double-stranded nucleic acids each including the above-described amplicons linked to each other in the forward direction are generated by the strand displacement extension reaction. At this time, the single-stranded DNAs released by the strand displacement extension reaction become Ω intermediates.

The other reaction pathway is such that, as shown in FIG. 9C, recombinant hybridization occurs between the sequence (C) and a complementary sequence (C') thereto (tail sequences) of the double-stranded amplicon. This reaction pathway further is divided into two kinds of reaction pathways, as shown in FIG. 9C. Specifically, one of the reaction pathways is such that, as shown in (j) to (l) in FIG. 9C, strand displacement hybridization occurs within the molecule of the double-stranded amplicon shown in (i) in FIG. 9C (the same as that shown in (i) in FIG. 9A). The other reaction pathway is such that, as shown in (j') to (l') in FIG. 9C, strand displacement hybridization occurs between two molecules of the double-stranded amplicon. First, one amplicon is provided as shown in (j) in FIG. 9C (the step (C1)), or two amplicons are provided in the state where their sequences are in opposite orientations as shown in (j') in FIG. 9C (the step (B1)). Subsequently, either within the molecule of the double-stranded amplicon as shown in (j) to (k) in FIG. 9C or between two molecules of the amplicon as shown in (j') to (k') in FIG. 9C, a sequence (C) hybridizes to a sequence (C') of another strand (tail substitution). During this tail substitution, as shown in (l) and (l') in FIG. 9C, folding of the folding sequence (D-D') or (E-E') at each end occurs. As a result, recombinant extension occurs from the 3' end of the sequence D of the folding sequence (D-D') or the sequence E of the folding sequence (E-E') at the 3' end with the strand on the opposite side as a template. By this extension reaction, a newly synthesized extended strand is generated ((m) in FIG. 9C). The reaction illustrated from (l) to (m) in FIG. 9C corresponds to the step of extending, through a strand displacement reaction, the 3' end of the folding sequence (D-D') in the single-stranded nucleic acid in the double strand ((j) in FIG. 9C) provided in the step (C1) using the complementary single-stranded nucleic acid as a template from the 3' end to the 5' end of the complementary single-stranded nucleic acid, thereby forming a partial double strand ((m) in FIG. 9C) in which part of the extended strand of the single-stranded nucleic acid hybridizes to the complementary single-stranded nucleic acid (the step (C2)). The reaction illustrated from (l') to (m) in FIG. 9C corresponds to the step of extending, through a strand displacement reaction, the 3' end of the folding sequence (D-D') in the single-stranded nucleic acid in one of the two double strands ((j') in FIG. 9C) provided in the step (B1) using the complementary single-stranded nucleic acid in the other double strand as a template, thereby forming a partial double strand ((m) in FIG. 9C) in which part of the extended strand of the single-stranded nucleic acid in the above-described one of the double strands hybridizes to the complementary single-stranded nucleic acid in the other double strand (the step (B2)). It is to be noted here that these extension reactions are not Switchback extension occurring from the folding sequence (D-D') or (E-E') at the 3' end using, as a template, a sequence of the strand in which the folding sequence is included itself.

Furthermore, as shown in (n) in FIG. 9C, a recombinant extension occurs from the 3' side folded part of the released folding sequence (E-E') with the strand on the opposite side as a template. As a result, an amplification product in which heterologous folding sequences form a hammerhead structure at a portion where the above-described amplicons are linked to each other is formed ((o) in FIG. 9C). The reaction illustrated from (n) to (o) in FIG. 9C corresponds to the step of extending, in the partial double strand ((m) in FIG. 9C) in the step (B2) or (C2), the 3' end of the complementary single-stranded nucleic acid (the upper strand in (m) in FIG. 9C) using the single-stranded nucleic acid as a template (this extension reaction is shown in (n) in FIG. 9C), thereby forming a complete double strand ((o) in FIG. 9C) (the step (B3) or (C3)).

The first and second synthesis reactions in the nucleic acid synthesis method according to the present invention have been described specifically above. It is to be noted, however, that an isothermal amplification method using the primer set according to the present invention may or may not include these synthesis reactions of the present invention.

Figure 10:
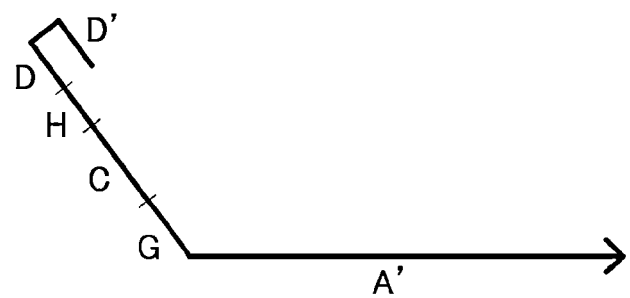
FIG. 10 shows an example of the first primer included in the primer set of the present invention.
Figure 11:
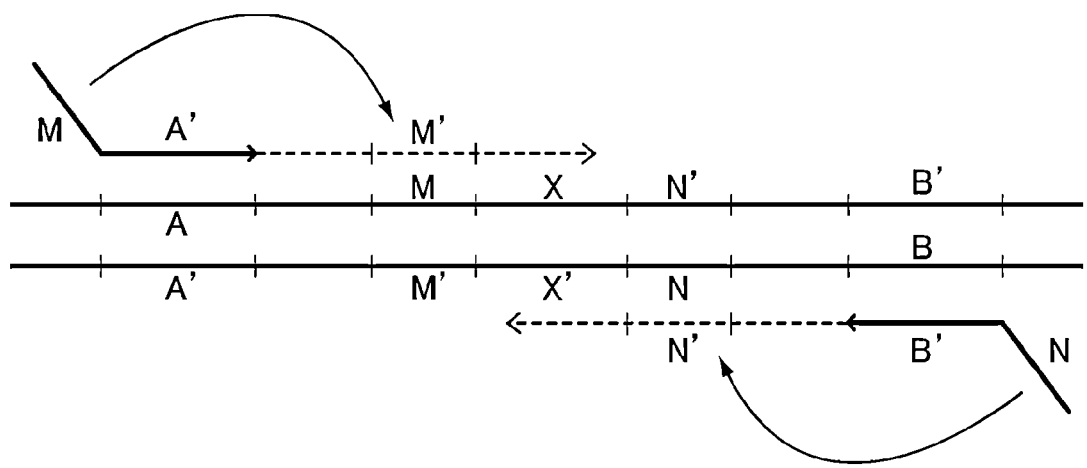
FIG. 11 shows an example of the LAMP method.
Figure 12:
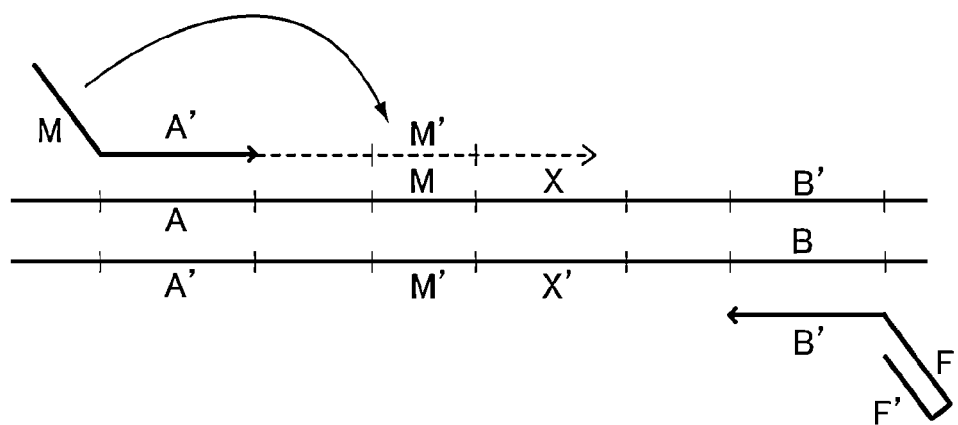
FIG. 12 shows an example of the SmartAmp2 method.
Figure 13:
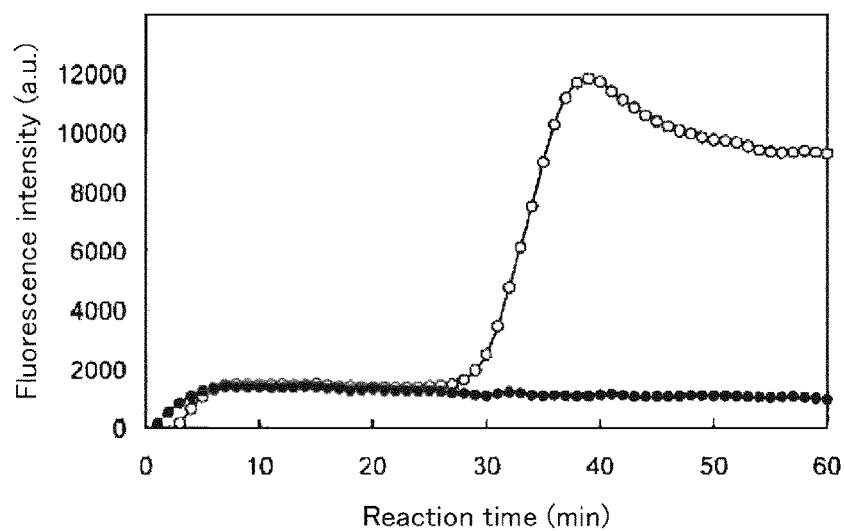
FIG. 13 is a graph showing fluorescence amplification curves obtained when the primer set of Example 1 (Forward Primer 1 and Reverse Primer 1) was used.
Figure 14:
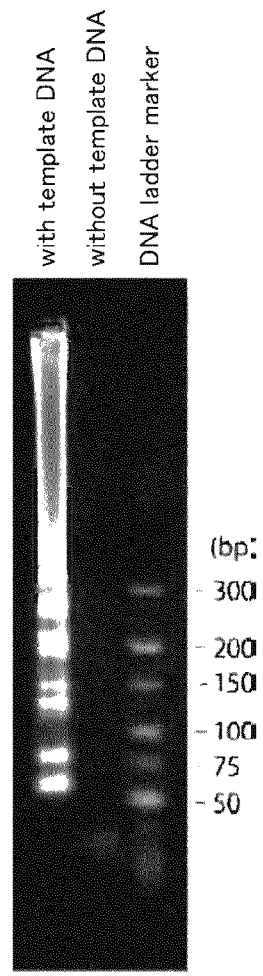
FIG. 14 is a photograph showing the result of agarose gel electrophoresis with respect to the reaction solution exhibiting an increase in fluorescence signal in FIG. 13.
Figure 15:
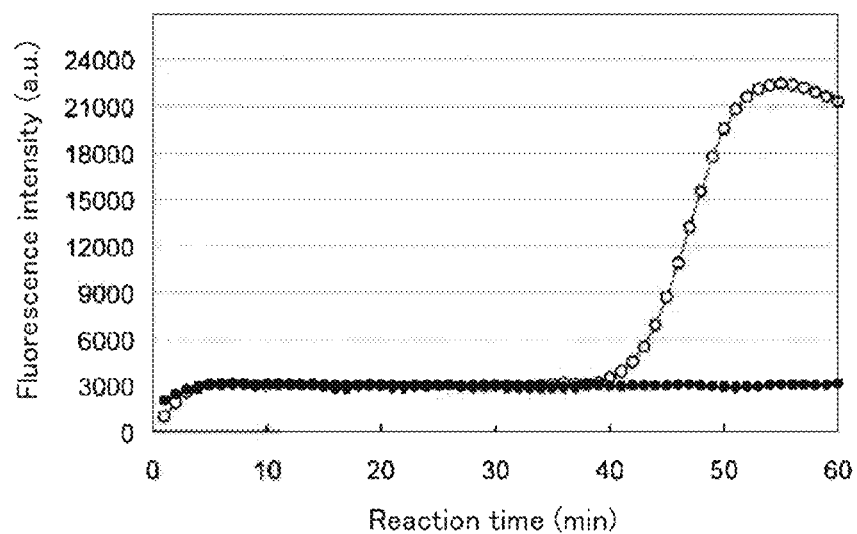
FIG. 15 is a graph showing fluorescence amplification curves obtained when the primer set of Example 1 (Forward Primer 2 and Reverse Primer 2) was used.
Figure 16:
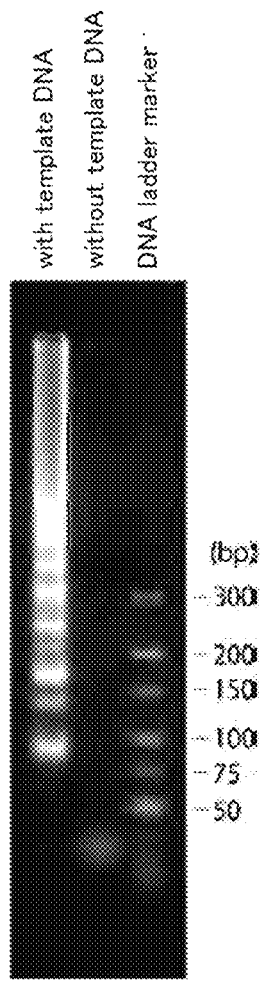
FIG. 16 is a photograph showing the result of agarose gel electrophoresis with respect to the reaction solution exhibiting an increase in fluorescence signal in FIG. 15.

In the primer set of the present invention, the first primer may have an intervening sequence (G) between the sequence (A') and the sequence (C), as shown in FIG. 10. The length of the intervening sequence (G) is, for example, 1 to 30 bases, preferably 1 to 20 bases, and more preferably 1 to 10 bases. Furthermore, in the primer set of the present invention, the first primer may have an intervening sequence (H) between the sequence (C) and the folding sequence (D-D'), as shown in FIG. 10. The length of the intervening sequence (H) is, for example, 1 to 30 bases, preferably, 1 to 20 bases, and more preferably 1 to 10 bases.

The primer set of the present invention may include a third primer, in addition to the first primer and the second primer. The third primer is such that it hybridizes to a target nucleic acid sequence or a sequence complementary thereto and does not compete with other primers in hybridization to the target nucleic acid sequence or the complementary sequence thereto.

In the present invention, the expression "does not compete with (and grammatical variations thereof)" means that hybridization of a primer of interest to a target nucleic acid does not interfere with the supply of a starting point of complementary strand synthesis by any other primer.

In the case where a target nucleic acid is amplified by the first primer and the second primer, for example, when an amplification product obtained by the amplification of the target nucleic acid is rendered partially single-stranded, the third primer can anneal to a target sequence present in the single strand moiety. As a result, a starting point of complementary strand synthesis is newly provided in the target nucleic acid sequence in the amplification product, and an extension reaction occurs therefrom. This allows a nucleic acid amplification reaction to be carried out more rapidly.

The third primer to be used is not necessarily limited to one kind. Two or more kinds of third primers may be used at the same time in order to improve the rapidity and specificity of a nucleic acid amplification reaction. Although the third primer typically has a different sequence from the first primer and the second primer, the third primer may hybridize to a region whose sequence is partially overlapping with the sequences of regions to which the first primer and the second primer hybridize, as long as it does not compete with these primers. The length of the third primer preferably is 2 to 100 bases, more preferably 5 to 50 bases, and still more preferably 7 to 30 bases.

The third primer primarily aims to play a supplementary role in accelerating a nucleic acid amplification reaction caused by the first primer and the second primer. Therefore, it is preferable that the third primer has a lower Tm than the 3' end of each of the first primer and the second primer. Also, the amount of the third primer to be added to an amplification reaction solution preferably is less than the added amount of each of the first primer and the second primer.

Examples of the third primer include, but not limited to, a primer described in WO 2002/24902, namely, a primer that acts on a template having a structure capable of forming a loop and provides a starting point for complementary strand synthesis in the loop portion. That is, the third primer may provide a starting point for complementary strand synthesis at any site within the sequence of a target nucleic acid.

The primers included in the primer set of the present invention are composed of deoxynucleotides and/or ribonucleotides. In the present invention, the term "ribonucleotide" (may be referred to simply as "N") refers to a ribonucleotide triphosphate, and examples thereof include ATP, UTP, CTP, and GTP. The ribonucleotide also encompasses derivatives thereof, such as, for example, ribonucleotide in which an oxygen atom at the α-position in a phosphate group is substituted with a sulfur atom (α-thio-ribonucleotide).

Examples of the primer include: oligonucleotide primers composed of an unmodified deoxynucleotide(s) and/or a modified deoxynucleotide(s); oligonucleotide primers composed of an unmodified ribonucleotide(s) and/or a modified ribonucleotide(s); and chimera oligonucleotide primers including an unmodified deoxynucleotide(s) and/or a modified deoxynucleotide(s) together with an unmodified ribonucleotide(s) and/or a modified ribonucleotide(s).

The primers included in the primer set of the present invention can be synthesized by any method applicable to oligonucleotide synthesis, such as, for example, a phosphotriester method, an H-phosphonate method, or a thiophosphonate method. The primers can be obtained easily by synthesizing them according to a phosphoamidite method using a DNA Synthesizer 394 manufactured by ABI (Applied Biosystem Inc.), for example.

A template nucleic acid or nucleic acid sample containing a target nucleic acid sequence, for use in a nucleic acid amplification reaction may be either DNA or RNA, and may be either a double strand or a single strand. The DNA encompasses cDNA, genomic DNA, and synthetic DNA. The RNA encompasses total RNA, mRNA, rRNA, siRNA, hnRNA, microRNA, and synthesized RNA. These nucleic acids can be prepared from, for example, a biological sample such as blood, a tissue, a cell, or further, an animal or plant, or a microorganism-derived sample or a virus-derived sample separated from a biological sample, a food, soil, wastewater, or the like.

The template nucleic acid or the nucleic acid sample can be isolated by any method. Examples of the method include: a dissolving treatment using a surfactant; sonication; stirring using glass beads; and a method using a French press or the like. In the case where an endogenous nuclease is present, it is preferable to purify the isolated nucleic acid. Purification of the nucleic acid can be carried out by phenol extraction, chromatography, ion exchange, gel electrophoresis, density-dependent centrifugation, or the like, for example.

More specifically, as the template nucleic acid or the nucleic acid sample, it is possible to use: a double-stranded nucleic acid such as a genomic DNA or a PCR fragment isolated by any of the above-described methods; or a single-stranded nucleic acid such as cDNA prepared from total RNA or mRNA through a reverse transcription reaction. The above-described double-stranded nucleic acid can be utilized most favorably when it is rendered single-stranded by denaturing.

An enzyme to be used in the above-described reverse transcription reaction is not particularly limited, as long as it has cDNA synthesis activity with RNA as a template. Examples of the enzyme include reverse transcriptases of various origins, such as avian myeloblastosis virus reverse transcriptase (AMV RTase), Rous-associated virus 2 reverse transcriptase (RAV-2 RTase), and Moloney murine leukemia virus reverse transcriptase (MMLV RTase). Also, it is possible to use a DNA polymerase having reverse transcription activity. An enzyme that exhibits reverse transcription activity at high temperature is most suitable for the object of the present invention. As such an enzyme, it is possible to use, for example, a DNA polymerase derived from a bacterium of the genus *Thermus* (such as TthDNA polymerase) or a DNA polymerase derived from a bacterium of the genus *Bacillus*. Examples of particularly preferable enzymes include thermophilic bacillus bacterium-derived DNA polymerases, such as B. st-derived DNA polymerases (Bst DNA polymerases) and B. ca-derived DNA polymerases (Bca DNA polymerase) including BcaBEST DNA polymerase and Bca(exo-) DNA polymerase, for example. For example, Bca DNA polymerase does not require a manganese ion for its reaction, so that it can synthesize cDNA under high temperature conditions while suppressing the formation of the secondary structure of the template RNA.

In a nucleic acid amplification reaction, a template nucleic acid in the form of a double-stranded nucleic acid can be used as it is. However, if the double-stranded nucleic acid is rendered single-stranded by denaturing when necessary, the primers can anneal to the template nucleic acid more efficiently. Raising the temperature to about 95° C. is a preferable method for denaturing a nucleic acid. Alternatively, the nucleic acid also can be denatured by raising the pH. In this case, however, it is necessary to lower the pH to hybridize the primers to the target nucleic acid.

The polymerase to be used in a nucleic acid amplification reaction is not limited, as long as it has strand displacement activity (strand displacement ability). Polymerases that exhibit their activities at ordinary temperatures, mesophilic polymerases, and heat-resistance polymerases all can be used suitably. This polymerase may be a naturally occurring polymerase or an artificially-mutated polymerase. Examples of such polymerases include DNA polymerases. Also, it is preferable that this DNA polymerase substantially does not have 5'→3' exonuclease activity. Such a DNA polymerase may be, for example, a mutant obtained by deleting the 5'→3' exonuclease activity from a thermophilic bacillus bacterium-derived DNA polymerase such as *Bacillus stearothermophilus* (referred to as "B.st" herein) or *Bacillus caldotenax* (referred to as "B. ca" herein), or a Klenow fragment of *E. coli*-derived DNA polymerase I. Examples of the DNA polymerase to be used in a nucleic acid amplification further include Vent DNA polymerase, Vent (Exo-) DNA polymerase, DeepVent DNA polymerase, DeepVent (Exo-) DNA polymerase, Φ29 phage DNA polymerase, MS-2 phage DNA polymerase, Z-Taq DNA polymerase, Pfu DNA polymerase, Pfu turbo DNA polymerase, KOD DNA polymerase, 9° Nm DNA polymerase, and Therminater DNA polymerase.

Furthermore, in the nucleic acid amplification reaction, when a DNA polymerase also having reverse transcription activity, such as, e.g., BcaBEST DNA polymerase or Bca (exo-) DNA polymerase, is used, a reverse transcription reaction from total RNA or mRNA and a DNA polymerase reaction using cDNA as a template can be carried out with the use of only one kind of polymerase. Also, the DNA polymerase may be used in combination with any of the above-listed reverse transcriptases such as MMLV reverse transcriptase.

Examples of other reagents to be used in a nucleic acid amplification reaction include: catalysts such as magnesium chloride, magnesium acetate, and magnesium sulfate; substrates such as dNTP Mix; buffer solutions such as a Tris-HCl buffer, a tricine buffer, a sodium phosphate buffer, and potassium phosphate buffer. Also, additives such as dimethyl sulfoxide (dimethyl sulfoxide) and betaine (N,N, N-trimethylglycine); acidic substances described in WO 99/54455; cation complexes; etc. also may be used.

In a nucleic acid amplification reaction, a melting temperature regulator may be added to a reaction solution in order to improve the nucleic acid amplification efficiency. Generally, the melting temperature (Tm) of a nucleic acid is determined by a specific nucleotide sequence in a double strand-forming part of a nucleic acid. By adding the melting temperature regulator to the reaction solution, it is possible to change this melting temperature. Thus, under conditions where the temperature is kept constant, it becomes possible to adjust the strength of the double strand formation in a nucleic acid. A common melting temperature regulator has an effect of lowering the melting temperature. By adding such a melting temperature regulator, it is possible to lower the melting temperature of a double strand-forming part between two strands of a nucleic acid. In other words, it becomes possible to decrease the strength of the double strand formation. Therefore, by adding such a melting temperature regulator to a reaction solution in the nucleic acid amplification reaction, even in a GC-rich nucleic acid region where a rigid double strand is formed or in a region where a complex secondary structure is formed, a double strand-forming part can be rendered single-stranded efficiently. As a result, after an extension reaction of a primer, a subsequent primer can hybridize to a target region more easily, whereby the nucleic acid amplification efficiency can be improved. The melting temperature regulator used in the present invention and the concentration thereof in a reaction solution can be selected as appropriate by those skilled in the art, considering other reaction conditions that may affect the hybridization conditions, such as the salt concentration and the reaction temperature. Therefore, although the melting temperature regulator is not particularly limited, it is preferable to use dimethyl sulfoxide (DMSO), betaine, formamide, or glycerol, or any combination thereof, and it is more preferable to use dimethyl sulfoxide (DMSO).

Furthermore, in a nucleic acid amplification reaction, an enzyme stabilizer also may be added to a reaction solution. This stabilizes the enzymes contained in the reaction solution, whereby the nucleic acid amplification efficiency can be improved. The enzyme stabilizer to be used in the present invention is not particularly limited, and may be any of those well known in the art, such as glycerol, bovine serum albumin, and saccharides.

Furthermore, in a nucleic acid amplification reaction, a reagent for enhancing the heat resistance of enzymes such as DNA polymerase and reverse transcriptase also may be added to a reaction solution as an enzyme stabilizer. This stabilizes the enzymes contained in the reaction solution, whereby the nucleic acid synthesis efficiency and amplification efficiency can be improved. Such a reagent may be any of those known in the art, and is not particularly limited. The reagent preferably is a saccharide, more preferably a monosaccharide or an oligosaccharide, and still more preferably trehalose, sorbitol, or mannitol, or a mixture of two or more of them.

A nucleic acid amplification reaction using the primer set of the present invention can be carried out isothermally. The terms "isothermally" or "isothermal" as used herein refers to maintaining an enzyme(s) and primers under substantially constant temperature conditions where they can substantially exhibit their functions. Furthermore, maintaining the "substantially constant temperature conditions" does not necessarily mean maintaining a given temperature precisely, and a temperature change within a range where the substantial functions of the enzyme(s) and the primers are not impaired is acceptable.

The nucleic acid amplification reaction under constant temperature conditions can be carried out by maintaining the temperature conditions where the enzyme(s) to be used can maintain its activity. In this nucleic acid amplification reaction, in order to cause a primer to anneal to a target nucleic acid, for example, the reaction temperature preferably is set to a temperature around the melting temperature (Tm) of the primer, or to a temperature equal to or lower than the melting temperature (Tm) of the primer. Furthermore, the level of the stringency preferably is set with consideration given to the melting temperature (Tm) of the primer. Therefore, this temperature preferably is from about 20° C. to about 75° C., more preferably from about 35° C. to about 65° C.

In the above-described nucleic acid amplification reaction, an amplification reaction is repeated until the enzyme(s) is deactivated or any one of the reagents including the primers is exhausted.

In the above-described nucleic acid amplification reaction, a nucleic acid including unnatural nucleotides can be used as a template nucleic acid (target nucleic acid sequence). The term "unnatural nucleotide" as used herein means a nucleotide that includes any base other than the bases included in natural nucleotides (adenine, guanine, cytosine, and thymine or uracil) and can be incorporated into a nucleic acid sequence. Examples of the unnatural nucleotide include xanthosines, diaminopyrimidines, isoG, and isoC (Proc. Natl. Acad. Sci. USA 92, 6329-6333, 1995). For amplification of a target nucleic acid including unnatural nucleotides, a non-heat resistant nucleic acid amplification enzyme generally is used. On the other hand, because the nucleic acid amplification reaction can be carried out isothermally at around 50° C., for example, the nucleic acid amplification enzyme (e.g., DNA polymerase or the like) is less liable to be deactivated as compared with the case of conventional PCR methods. Therefore, the nucleic acid amplification reaction using the primer set of the present invention is effective also in amplification of a target nucleic acid including unnatural nucleotides using a non-heat resistant nucleic acid amplification enzyme. An enzyme to be used in the amplification of a nucleic acid including unnatural nucleotides is not particularly limited, as long as it can amplify such a target nucleic acid. Particularly from the viewpoint of incorporation efficiency, the following enzymes are suitable: Y188L/E478Q mutated HIV I reverse transcriptase, AMV reverse transcriptase, Klenow fragments of DNA polymerases, 9° N DNA polymerase, Hot Tub DNA polymerase, and the like (Michael Sismour et al., Biochemistry 42, No. 28, 8598, 2003; U.S. Pat. No. 6,617,106; Michael J. Lutz et al., Bioorganic & Medical Chemistry letters 8, 1149-1152, 1998; etc.). Also, a substance that improves the heat resistance of a nucleic acid amplification enzyme (e.g., trehalose) may be added to a reaction solution. This allows the amplification of the target nucleic acid including unnatural nucleotides to be carried out more efficiently.

The presence of an amplification product obtained by the nucleic acid amplification method according to the present invention can be detected by various kinds of methods. One example of the method is detecting an amplification product of a particular size according to a commonly used gel electrophoresis. In this method, the amplification product can be detected using a fluorescent substance such as ethidium bromide or SYBR Green, for example. Another example of the method is detecting an amplification product through hybridization of a labeled probe labeled with biotin or the like. The biotin can be detected through binding with a fluorescently labeled avidin, avidin bound to an enzyme such as peroxidase, or the like. Still another example of the method is detection utilizing an immunochromatograph. In this method, the detection is achieved using a chromatographic medium that utilizes a label detectable with the naked eye (an immunochromatography method). The above-described amplified fragment is hybridized to a labeled probe, and a trapping probe that can hybridize to a different sequence in this amplified fragment is immobilized on a chromatographic medium. Then, the amplified fragment hybridizing to the labeled probe can be trapped on the immobilized portion, so that it can be detected on the chromatographic medium. As a result, simple detection with the naked eye becomes possible. Moreover, the nucleic acid amplification method according to the present invention can achieve very high amplification efficiency in a nucleic acid amplification reaction. Thus, utilizing the fact that pyrophosphoric acid is generated as a by-product of the amplification, it is also possible to detect the amplification product indirectly. Examples of such a method include a method in which, utilizing the fact that pyrophosphoric acid binds to magnesium in a reaction solution to cause white deposition of magnesium pyrophosphate, the white deposition in the reaction solution is observed through visual observation. Examples of the method further include a method utilizing the fact that pyrophosphoric acid strongly binds to metal ions such as magnesium ions to form insoluble salts, so that the concentration of the magnesium ions in the reaction solution decreases markedly. In this method, a metal indicator whose color tone changes in accordance with the magnesium ion concentration (e.g., Eriochrome Black T, Hydroxy Naphthol Blue, or the like) is added to the reaction solution beforehand, so that whether or not the amplification has occurred can be detected by observing the change in color of the reaction solution through visual observation. Also, by using Calcein or the like, an increase in fluorescence accompanying the amplification reaction can be observed through visual observation. Thus, real time detection of the amplification product becomes possible.

According to a preferable embodiment of the present invention, the presence of an amplification product obtained by the nucleic acid amplification method of the present invention also can be detected by observing the agglutination of solid-phase carriers caused by the generation of the amplification product. When such detection is to be carried out, at least one of the primers included in the primer set of the present invention is configured so as to include a solid-phase carrier or a site that can bind with the solid-phase carrier. The solid-phase carrier or the site that can bind with the solid-phase carrier may be introduced into any part of the primer, e.g., the 3' end part, the 5' end part, or a central region, and preferably is introduced to the 5' end part. Alternatively, a substrate to be used in the nucleic acid amplification reaction may be configured so as to include a solid-phase carrier or a site that can bind with the solid-phase carrier.

As the solid-phase carrier to be used in the present invention, it is possible to use a carrier insoluble in a reaction solution used in a nucleic acid amplification reaction, or a phase transition carrier whose state changes from liquid phase to solid phase (gel phase) or from solid phase (gel phase) to liquid phase before and after the amplification. Examples of a preferable solid-phase carrier include: water-insoluble organic polymeric carriers; water-insoluble inorganic polymeric carriers; synthetic polymeric carriers; phase transition carriers; metal colloids; and magnetic particles. Examples of the preferable solid-phase carrier further include: solvent-insoluble organic polymeric carriers; solvent-insoluble inorganic polymeric carriers; solvent-soluble polymeric carriers; and gel polymeric carriers. Examples of the water-insoluble organic polymers include: silicon-containing substances such as porous silica, porous glass, diatomaceous earth, and cerite; crosslinked products of polysaccharides, such as nitrocellulose, hydroxyapatite, agarose, dextran, cellulose, and carboxymethyl cellulose; crosslinked products of proteins, such as methylated albumin, gelatin, collagen, and casein; gel-like particles; and dye sols. Examples of the water-insoluble inorganic polymers include aluminium oxide, titanium oxide, and ceramic particles. Examples of the synthetic polymers include polystyrenes, poly(meth)acrylates, polyvinyl alcohols, polyacrylonitriles, and copolymers thereof, as well as styrene-styrenesulfonic acid copolymers and vinyl acetate-acrylic ester copolymers. Examples of the metal colloids include gold colloids. Examples of the magnetic particles include: beads of magnetic iron oxide; monodispersed superparamagnetic particles having finely pulverized magnetic iron oxide particles on their surfaces (JP 4(1992)-501959 A); superparamagnetic iron oxide-containing magnetically responsive particles covered with a polymerized silane membrane (JP 7(1995)-6986 B); and fine powdery magnetizable particles encapsulated in an organic polymer. A magnetized solid-phase carrier can separate a solid and a liquid utilizing a magnetic force. The solid-phase carrier may be in the form of particles, a membrane, fiber, and a filter, for example. It is particularly preferable that the solid-phase carrier is in the form of particles, and the surfaces of the particles may be either porous or non-porous. Examples of a particularly preferable solid-phase carrier include: latex obtained by uniformly dispersing a synthetic polymer carrier in water or the like; metal colloid particles such as gold colloid; and magnetic particles such as magnetic beads.

Immobilization of the primer or the substrate on the solid-phase carrier can be carried out by a method known to those skilled in the art, and such a method may utilize either physical binding or chemical binding. Immobilization of the primer or the substrate on the solid-phase carrier can be carried out using a substance that generally can label an oligonucleotide such as a primer or a probe in combination with a solid-phase carrier to which a substance that can bind to the oligonucleotide has been bound, for example. As the combination of the substances used for this purpose, those well known in the art may be employed. Examples of the combination include: the combination of biotin with either avidin or streptavidin; the combination of an antigen with an antibody that can bind to the antigen; the combination of a ligand with a receptor that can bind to the ligand; and the combination of two nucleic acids that can hybridize to each other. Specifically, for example, by binding a primer or a substrate labeled with biotin to a solid-phase carrier whose surface is coated with avidin or streptavidin, the primer or the substrate can be immobilized on the solid-phase carrier. Examples of the antigen include haptens such as FITC, DIG, and DNP, and examples of the antibodies that can bind to these antigens include anti-FITC antibodies, anti-DIG antibodies, and anti-DNP antibodies. These antibodies may be either monoclonal or polyclonal. In particular, the binding between biotin and streptavidin is highly specific, and also the binding efficiency is favorable. Thus, the combination of biotin and streptavidin is particularly preferable. A labeling substance such as biotin, a hapten, or a ligand can be introduced into the 5' end part of a primer by a known method (see JP 59(1984)-93099 A, JP 59(1984)-148798 A, and JP 59(1984)-204200 A) either alone, or, when necessary, in combination of two or more of kinds of them.

The site (or group) that can bind with the solid-phase carrier to be used in the present invention can be selected depending on the above-described method for immobilizing the primer or the substrate on the solid-phase carrier. Thus, the site may achieve either physical binding or chemical binding with the solid-phase carrier, and preferably achieve specific binding. Examples of the site that can bind with the solid-phase carrier include biotin, avidin, streptavidin, antigens, antibodies, ligands, receptors, nucleic acids, and proteins listed above. Among them, biotin or streptavidin is preferable, and biotin is more preferable. By using a primer or substrate including such a site, after a nucleic acid amplification reaction, the solid-phase carrier can be bound to the obtained amplification product. The solid-phase carrier used in this case may include, when necessary, a binding partner of the site included in the primer or the substrate. Such a binding partner is present in the form capable of biding to the site included in the primer or the substrate. The binding partner preferably is present on a surface of the solid-phase carrier, and more preferably is applied onto a surface of the solid-phase carrier.

According to one embodiment of the present invention, the primer sets of the present invention are provided for a plurality of target nucleic acids, respectively. These primers sets are immobilized on a solid-phase carrier(s) in such a manner that they can be discriminated from each other, and nucleic acid amplification reactions are carried out using these immobilized primer sets. As a result, the plurality of target nucleic acids can be amplified at the same time, and the respective amplification products obtained can be detected in a discriminable manner. Detection of the amplification products can be carried out using an intercalator or the like. For example, by immobilizing the plurality of primers at predetermined positions on a planar solid-phase carrier, it is possible to determine, after the nucleic acid amplification reaction and the detection of amplification products, which of the target nucleic acid is amplified based on the position where the amplification product is detected. The solid-phase carrier that can be used for this purpose is not limited to a planar solid-phase carrier as described above, and it is also possible to use a solid-phase carrier known in the art, such as bead surfaces discriminable from each other (U.S. Pat. No. 6,046,807 and U.S. Pat. No. 6,057,107), a quasi-planar carrier prepared by solid-phasing the respective primer sets on fibrous carriers, tying the fibrous carriers in a bundle, and then slicing the bundle into a thin section (JP 2000-245460 A), or the like.

An amplified fragment obtained by the nucleic acid amplification method according to the present invention is composed of ordinary bases. Thus, after the amplification, it is possible to subclone the amplified fragment into a suitable vector using a restriction enzyme site inside the amplified fragment. Furthermore, the amplified fragment can be subjected to a restriction enzyme treatment such as RFLP, so that the amplified fragment can be used widely in the field of genetic testing. Moreover, it is possible to generate the amplified fragment including an RNA polymerase promoter sequence, which allows RNA to be synthesized directly from the amplified fragment. The thus-synthesized RNA can be used as a RNA probe, siRNA, or the like.

Furthermore, in the nucleic acid amplification method according to the present invention, a base labeled with biotin or a fluorescent substance can be used as a substrate, instead of a commonly used dNTP. Thus, it is also possible to prepare a DNA probe labeled with biotin or a fluorescent substance. Moreover, it is also possible to determine the presence or absence of the amplification product by means of a certain structure such as biotin or a labeling substance.

Each primer included in the primer set according to the present invention may include a restriction enzyme recognition site. With this configuration, it becomes possible to improve the nucleic acid amplification efficiency. More specifically, a nick is generated in an amplification product by a restriction enzyme corresponding to the restriction enzyme recognition site in the primer. Thus, it becomes possible to cause a complementary strand synthesis reaction of strand displacement type with this nick as a starting point of synthesis. This method is basically based on the principle of the SDA method described herein as the background art.

Also, each primer included in the primer set of the present invention may include a RNA polymerase promoter sequence. With this configuration, it becomes possible to improve the nucleic acid amplification efficiency. This method is basically based on the principle of the NASBA method described herein as the background art.

Furthermore, the primer set of the present invention may include an "outer primer", which is utilized in the LAMP method or the SDA method. With this configuration, it becomes possible to improve the nucleic acid amplification efficiency. As the outer primer, it is possible to use a primer that can provide a starting point of complementary strand synthesis at a site outside of a target nucleic acid sequence in a template nucleic acid.

According to the nucleic acid amplification method of the present invention, a single-stranded nucleic acid to be immobilized on a DNA chip, a single-stranded DNA probe for base sequence determination, a megaprimer for used in a long chain PCR method, and the like can be prepared simply and rapidly. Furthermore, according to the nucleic acid amplification method of the present invention, it is also possible to selectively amplify only a sense sequence or only an antisense sequence of a target nucleic acid, depending on the purpose of amplification.

A single-stranded nucleic acid prepared by the nucleic acid amplification method of the present invention can be used as a DNA fragment to be immobilized on a DNA chip. That is, the nucleic acid amplification method according to the present invention can be used as a method for preparing a DNA strand to be immobilized in the production of a DNA chip. It is also possible to prepare a DNA chip by immobilizing the 5' end of a primer on the DNA chip beforehand and then performing nucleic acid amplification on the chip.

Furthermore, by adding a fluorescently labeled probe that can hybridize to an amplification product to a reaction solution prior to the nucleic acid amplification, it becomes possible to detect the amplification product in real time while carrying out the nucleic acid amplification on the DNA chip.

By utilizing a nucleic acid amplification reaction using the primer set of the present invention, it is possible to detect (determine) the presence or absence of a mutation in a nucleic acid sequence contained in a nucleic acid sample. To this end, the primer set can be designed so that the mutation site is included in the sequence (A) or the sequence (B). With this configuration, it becomes possible to detect (determine) the presence or absence of the mutation by checking the presence or absence of an amplification product.

In the mutation detection method according to the present invention, when a primer set designed so as to target a nucleic acid sequence having a target mutation is used, the presence of an amplification product after a nucleic acid amplification reaction indicates the presence of the mutation, and the absence or decrease of the amplification product indicates the absence of the mutation. On the other hand, when a primer set designed so as to target a nucleic acid sequence not having a target mutation is used, the presence of an amplification product after a nucleic acid amplification reaction indicates the absence of the mutation, and the absence or decrease of the amplification product indicates the presence of the mutation. The "decrease of the amplification product" as used herein means that the amount of the obtained amplification product is smaller than the amount of the amplification product obtained when the target nucleic acid sequence is present in a nucleic acid sample.

In the present invention, the term "mutation" means that a nucleic acid sequence includes a base(s) (a base pair(s) in the case of a double-stranded nucleic acid) different from that in a reference nucleic acid sequence. In the present invention, the term "mutation" encompasses deletion, insertion, addition, and/or substitution of a base(s). Also, in the present invention, the term "reference nucleic acid" refers to a nucleic acid having, regarding a certain base sequence, a wild-type (also referred to as "normal type") sequence regarded as a standard base sequence, e.g., a standard genotype. In contrast, the term "test nucleic acid" means a nucleic acid for which the presence of a base(s) different from that in the reference nucleic acid (mutation) is examined by the mutation detection method according to the present invention. In other words, the term "test nucleic acid" means a nucleic acid that is present in a nucleic acid sample and has the same sequence as the reference nucleic acid except for a base(s) corresponding to the mutation. Furthermore, in the present invention, a "base(s) corresponding to the mutation" or a "nucleotide residue(s) corresponding to the mutation" means a base(s) or a nucleotide residue(s) present at the mutation site in a nucleic acid, and hence, it means a base(s) or a nucleotide residue(s) included at the mutation site in both the reference nucleic acid and the mutant nucleic acid. For example, in the detection of a mutation in a gene of a patient suspected of having a genetic disease, the gene of the patient suspected of having the mutation is a test nucleic acid, and a corresponding gene of a healthy subject is a reference nucleic acid.

The above-described test nucleic acid and reference nucleic acid may be either a naturally occurring nucleic acid or an artificially synthesized nucleic acid. The term "nucleic acid" as used herein means a polynucleotide including any unmodified nucleotide and/or modified nucleotide. Each of the test nucleic acid and the reference nucleic acid typically is DNA such as cDNA, genomic DNA, or synthetic DNA, or RNA such as mRNA, total RNA, hnRNA, siRNA, or synthesized RNA. The term "polynucleotide" as used herein encompasses, for the sake of convenience, polynucleotides and oligonucleotides, as well as artificially-synthesized nucleic acids such as peptide nucleic acids, morpholino nucleic acids, methylphosphonate nucleic acids, and S-oligo nucleic acids. The test nucleic acid and the reference nucleic acid can be selected freely by a person conducting an examination. Moreover, during the detection, these nucleic acids may be present together.

A nucleic acid sample containing a test nucleic acid can be obtained from a subject, which is, for example, a human or a non-human animal. In this case, the nucleic acid can be extracted from a desired specimen of the subject, such as a tissue, organ, or cell, by a method known in the art. If necessary, after the extraction, conditions such as the size, the degree of purification, etc. of the obtained nucleic acid fragment can be adjusted as appropriate. Thereafter, the test nucleic acid in the nucleic acid sample may be amplified by carrying out an amplification reaction according to a commonly used polymerase chain reaction (PCR) method or the like.

The test nucleic acid and the reference nucleic acid each may be a single strand or a double strand. The term "double-stranded nucleic acid" as used herein can mean any of a double-stranded DNA, a double-stranded RNA, and a DNA/RNA. A double-stranded nucleic acid may be used as a nucleic acid sample either as it is or after being amplified using a vector such as a phage or a plasmid.

EXAMPLES

Next, examples of the present invention will be described. It is to be noted, however, that the present invention is by no means restricted or limited by the following examples.

Example 1

In the present example, a target nucleic acid sequence was amplified isothermally using the following two kinds of primer sets: a primer set configured so that either one of a first primer and a second primer includes a folding sequence (D-D'); and a primer set configured so that a first primer includes a folding sequence (D-D') and a second primer includes a folding sequence (E-E').

A reaction solution was prepared by adding a forward primer having the following sequence (Forward Primer 1: SEQ ID NO: 1 or Forward Primer 2: SEQ ID NO: 2) and a reverse primer having the following sequence (Reverse Primer 1: SEQ ID NO: 3, or Reverse Primer 2:SEQ ID NO: 4) so that the concentration of each primer was 2 µM to a solution with a volume of 25 µL containing the following components with the following final concentrations: 1.4 mM dNTP, 5% DMSO, 20 mM Tris-HCl (pH 8.0), 30 mM potassium acetate, 10 mM sodium sulfate, 8 mM magnesium sulfate, 0.1% Tween 20, 1/100000 dilution of SYBR Green I (Takara Shuzo Co., Ltd.), and 12 units of Aac DNA polymerase. In each of the following primers, an underlined part indicates a folding sequence, and a boxed part indicates a sequence common to the forward and reverse primers.

Forward Primer 1

(SEQ ID NO: 1)

5'-AGGACGCTGAGATGCGTCCTAGCGATGCGTAGACAACTGGAAAG-3'

Forward Primer 2

(SEQ ID NO: 2)

5'-AATATATATATATATTCGGAGGAGGTGGAGGAGACAACTGGAAAG-3'

Reverse Primer 1

(SEQ ID NO: 3)

5'-AGCGATGCGTATGGGCCTATTGGA-3'

Reverse Primer 2

5'-ACCTTCTGTTCACCCTCAGAAGGTCGGAGGAGGTGGAGGATGGGCCTATTGGA-3'

As a template DNA, $2\times10^4$ copies of a plasmid DNA having a partial sequence (SEQ ID NO: 5) of cDNA of the N2 segment of the RNA genome of influenza A (H3N2) was added to the reaction solution, and the resultant mixture was allowed to react in a real-time PCR system MX3000p (Agilent) at a constant temperature of 60° C. for 60 minutes. Then, the nucleic acid amplification activity was examined by obtaining a fluorescence amplification curve via a FAM filter. Also, in order to examine the nucleic acid amplification product, 5 A of the solution after the reaction was applied to agarose gel electrophoresis using 3% (w/v) NuSieve agarose, and a band pattern was observed utilizing ethidium bromide staining.

Influenza A (H3N2) N2 segment, partial cDNA (SEQ ID NO: 5)

401 bp
5'-CCAGGAGTCAGAATGCGTTTGTATCAATGGAACTTGTACAGTAGTAA

TGACTGATGGGAGTGCTTCAGGAAAAGCTGATACTAAAATACTATTCATT

GAGGAGGGGAAAATCGTTCATACTAGCACATTGTCAGGAAGTGCTCAGCA

TGTCGAGGAGTGCTCCTGCTATCCTCGATATCCTGGTGTCAGATGTGTCT

GCAGAGACAACTGGAAAGGCTCCAATAGGCCCATCGTAGATATAAACATA

AAGGATCATAGCATTGTTTCCAGTTATGTGTGTTCAGGACTTGTTGGAGA

CACACCCAGAAAAAACGACAGCTCCAGCAGTAGCCATTGTTTGGATCCT

AACAATGAAGAAGGTGGTCATGGAGTGAAAGGCTGGGCCTTTGATGATG

GAAATG-3'

(Result 1: Result of the Isothermal Reaction Using the Primer Set Configured so that Only the Forward Primer Includes the Folding Sequence)

FIG. 13 shows fluorescence amplification curves obtained when Forward Primer 1 (SEQ ID NO: 1) and Reverse Primer 1 (SEQ ID NO: 3) were used in the presence of the template DNA (open circle) and in the absence of the template DNA (filled circle) (meanings of the open circle and the filled circle are the same throughout the following examples). As can be seen from FIG. 13, a marked increase in fluorescence signal was observed in the reaction solution containing the template DNA. FIG. 14 is a photograph showing the result of the agarose gel electrophoresis with respect to the reaction solution exhibiting the increase in fluorescence signal in FIG. 13. As can be seen from FIG. 14, a periodic band pattern was observed in a region extending from a short strand to a long strand, which revealed the occurrence of isothermal nucleic acid amplification.

(Result 2: Result of the Isothermal Reaction Using the Primer Set Configured so that Both the Forward and Reverse Primers have Folding Sequences Different from Each Other)

FIG. 15 shows fluorescence amplification curves obtained when Forward Primer 2 (SEQ ID NO: 2) and Reverse Primer 2 (SEQ ID NO: 4) were used. As can be seen from FIG. 15, similarly to Result 1, a marked increase in fluorescence signal was observed in the reaction solution containing the template DNA. FIG. 16 is a photograph showing the result of the agarose gel electrophoresis with respect to the reaction solution exhibiting the increase in fluorescence signal in FIG. 15. As can be seen from FIG. 16, a periodic band pattern was observed in a region extending from a short strand to a long strand. However, the band patterns in FIG. 16 show different periodicity than the band patterns in FIG. 14. Thus, this revealed the occurrence of isothermal nucleic acid amplification with a different amplification pattern than that in Result 1.

Example 2

In the present example, a target nucleic acid sequence was amplified isothermally using a primer set configured so that a first primer and a second primer each includes an intervening sequence (H) inserted between a folding sequence (D-D') or (E-E') and a common sequence (C). The intervening sequence (H) in the first primer was different from the intervening sequence (H) in the second primer.

The reaction solution in the present example had the same composition as the reaction solution in Example 1, except for the primers. Specifically, the reaction solution was prepared by adding a forward primer having the following sequence (Forward Primer 3: SEQ ID NO: 6) and a reverse primer having the following sequence (Reverse Primer 3: SEQ ID NO: 7) so that the concentration of each primer was 2 μM to a solution with a volume of 25 μL containing the following components with the following final concentrations: 1.4 mM dNTP, 5% DMSO, 20 mM Tris-HCl (pH 8.0), 30 mM potassium acetate, 10 mM sodium sulfate, 8 mM magnesium sulfate, 0.1% Tween 20, 1/100000 dilution of SYBR Green I (Takara Shuzo Co., Ltd.), and 12 units of Aac DNA polymerase. In each of the following primers, an underlined (single-underlined) part indicates a folding sequence, a boxed part indicates a sequence common to the forward and reverse primers, and a double-underlined part indicates an intervening sequence.

```
Forward Primer 3
                                                    (SEQ ID NO: 6)
5'-GCATTCACCCCCCGATTAGATATTCTATAGACAACTGGAAAG-3'

Reverse Primer 3
                                                    (SEQ ID NO: 7)
5'-AGGACGCTGAGATGCGTCCTTTTTTTGATTAGATATTCTATATGGGCCTATTGGA-3'
```

As in Example 1, as a template DNA, $2 \times 10^4$ copies of a plasmid DNA having a partial sequence (SEQ ID NO: 5) of cDNA of the N2 segment of the RNA genome of influenza A (H3N2) was added to the reaction solution, and the resultant mixture was allowed to react in a real-time PCR system MX3000p (Agilent) at a constant temperature of 60° C. for 90 minutes. Then, the nucleic acid amplification activity was examined by obtaining a fluorescence amplification curve via a FAM filter. Also, in order to examine the nucleic acid amplification product, 5 µL of the solution after the reaction was applied to agarose gel electrophoresis using 3% (w/v) NuSieve agarose, and a band pattern was observed utilizing ethidium bromide staining.

(Result 3: Result of Isothermal Reaction Using Primers Having Intervening Sequences (H))

Figure 17:
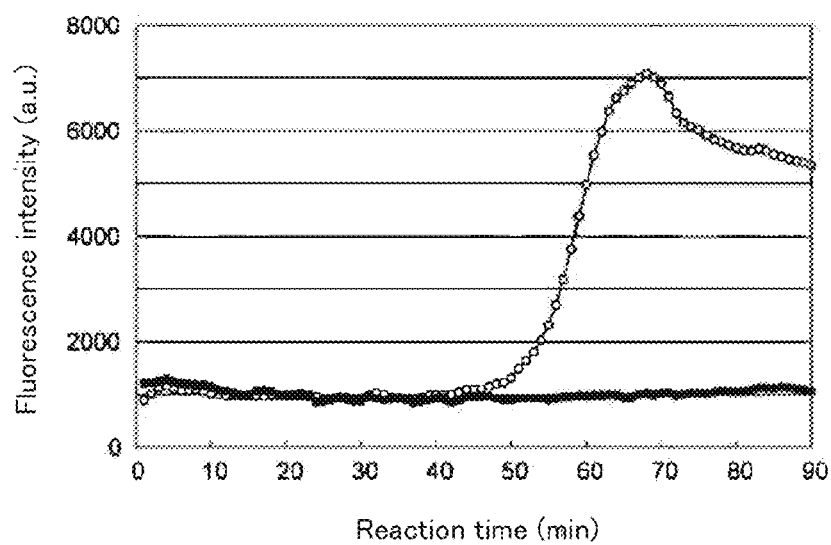
FIG. 17 is a graph showing fluorescence amplification curves obtained when the primer set of Example 2 (Forward Primer 3 and Reverse Primer 3) was used.
Figure 18:
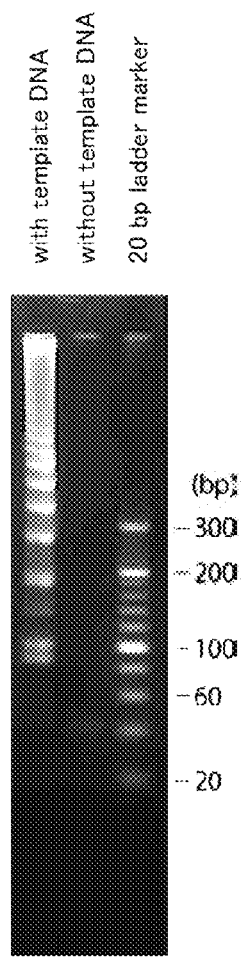
FIG. 18 is a photograph showing the result of agarose gel electrophoresis with respect to the reaction solution exhibiting an increase in fluorescence signal in FIG. 17.

FIG. 17 shows fluorescence amplification curves obtained when Forward Primer 3 (SEQ ID NO: 6) and Reverse Primer 3 (SEQ ID NO: 7) were used. As can be seen from FIG. 17, a marked increase in fluorescence signal was observed in the reaction solution containing the template DNA. FIG. 18 is a photograph showing the result of the agarose gel electrophoresis with respect to the reaction solution exhibiting the increase in fluorescence signal in FIG. 17. As can be seen from FIG. 18, a periodic band pattern composed of pairs of two bands was observed in a region extending from a short strand to a long strand, which revealed the occurrence of isothermal nucleic acid amplification in the reaction solution.

Example 3

Effect of a Third Primer

The present example examined whether a third primer designed so as to be complementary to a region between anneal regions of a first primer and a second primer anneal in a target nucleic acid exhibits an effect of improving an isothermal amplification reaction in the present invention.

First, in the present example, first and second primers each including an intervening sequence (H) inserted between a folding sequence (D-D') or (E-E') and a common sequence (C) were used. The reaction solution in the present example had the same composition as the reaction solution in Example 1, except for the primers. Specifically, the reaction solution excluding the primer was a solution with a volume of 25 µL containing the following components with the following final concentrations: 1.4 mM dNTP, 5% DMSO, 20 mM Tris-HCl (pH 8.0), 30 mM potassium acetate, 10 mM sodium sulfate, 8 mM magnesium sulfate, 0.1% Tween 20, 1/100000 dilution of SYBR Green I (Takara Shuzo Co., Ltd.), and 12 units of Aac DNA polymerase. To this solution, a forward primer having the following sequence (Forward Primer 4: SEQ ID NO: 8) as the first primer and a reverse primer having the following sequence (Reverse Primer 4: SEQ ID NO: 9) as the second primer were added so that the concentration of each primer was 2 µM. Further, the following boost primer (Boost Primer 1 or 2: SEQ ID NO: 10 or 11) as the third primer was added to the solution so that the concentration thereof was 0.66 µM. Thus, the reaction solution was prepared. In each of the following primer sequences, an underlined (single-underlined) part indicates a folding sequence, a boxed part indicates a sequence common to the forward and reverse primers, and a double-underlined part indicates an intervening sequence.

```
Forward Primer 4
                                                    (SEQ ID NO: 8)
5'-AGGACGCTGAGATGCGTCCTTTTTAGCGATGCGTTGAATATAAACTTGTGGTAGT-3'

Reverse Primer 4
                                                    (SEQ ID NO: 9)
5'-GCGACTCGCCCCAGCGATGCGTCTGAATTAGCTGTATCGTCAAG-3'

Boost Primer 1
                                                    (SEQ ID NO: 10)
5'-CAAGAGTGCC-3'

Boost Primer 2
                                                    (SEQ ID NO: 11)
5'-CCACCAGCTCC-3'
```

In the present example, a target sequence was a partial sequence (SEQ ID NO: 12) including the k-ras gene. Thus, a human genomic DNA (Human Genomic DNA, Male; Cat # G1471, available from Promega) was used as a template DNA. 10 ng of the human genomic DNA was added to the reaction solution, and the resultant mixture was allowed to react in a real-time PCR system MX3000p (Agilent) at a constant temperature of 60° C. for 100 minutes. The nucleic acid amplification activity was examined by obtaining a fluorescence amplification curve via a FAM filter. Furthermore, in order to examine the nucleic acid amplification product, 5 A of the solution after the reaction was applied to agarose gel electrophoresis using a 3% (w/v) NuSieve agarose, and a band pattern was observed utilizing ethidium bromide staining.

Human Genome, Partial DNA (SEQ ID NO: 12)

```
401 bp
5'-TTTCATGATTGAATTTTGTAAGGTATTTTGAAATAATTTTTCATATA
AAGGTGAGTTTGTATTAAAAGGTACTGGTGGAGTATTTGATAGTGTATTA
ACCTTATGTGTGACATGTTCTAATATAGTCACATTTTCATTATTTTTATT
ATAAGGCCTGCTGAAAATGACTGAATATAAACTTGTGGTAGTTGGAGCTG
GTGGCGTAGGCAAGAGTGCCTTGACGATACAGCTAATTCAGAATCATTTT
GTGGACGAATATGATCCAACAATAGAGGTAAATCTTGTTTTAATATGCAT
ATTACTGGTGCAGGACCATTCTTTGATACAGATAAAGGTTTCTCTGACCA
TTTTCATGAGTACTTATTACAAGATAATTATGCTGAAAGTTAAGTTATCT
GAAA-3'
```

(Result 4: Result of the Isothermal Reaction when the Third Primer was Used)

Figure 19:
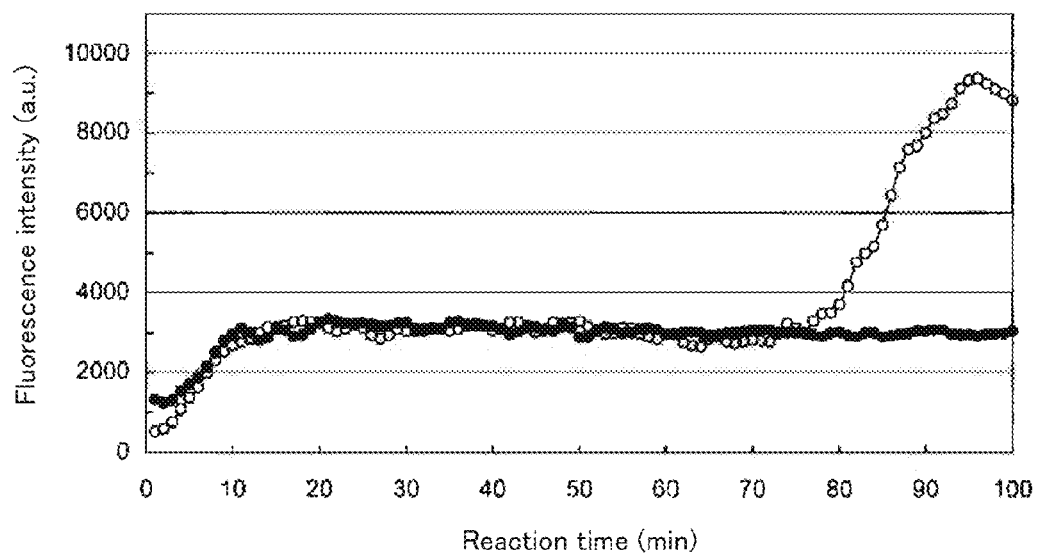
FIG. 19 is a graph showing fluorescence amplification curves obtained when the primer set of Example 3 (Forward Primer 4 and Reverse Primer 4) was used.
Figure 20:
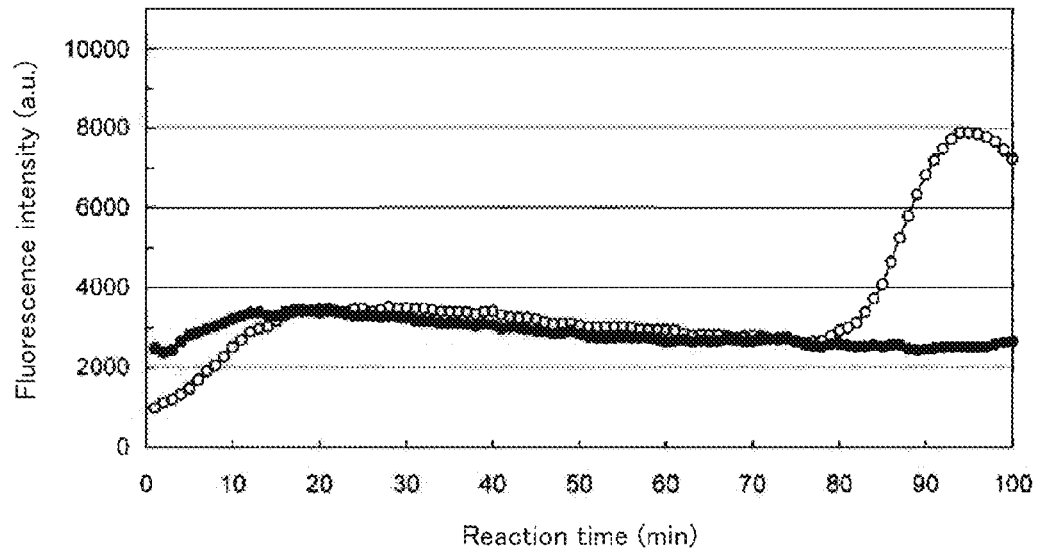
FIG. 20 is a graph showing fluorescence amplification curves obtained when only Boost Primer 1 of Example 3 was used.
Figure 21:
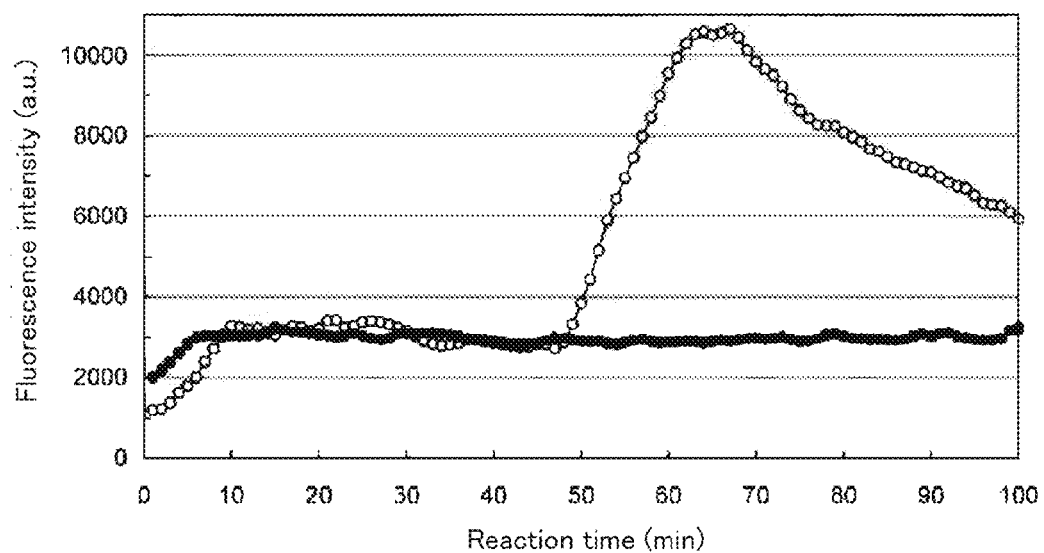
FIG. 21 is a graph showing fluorescence amplification curves obtained when only Boost primer 2 of Example 3 was used.
Figure 22:
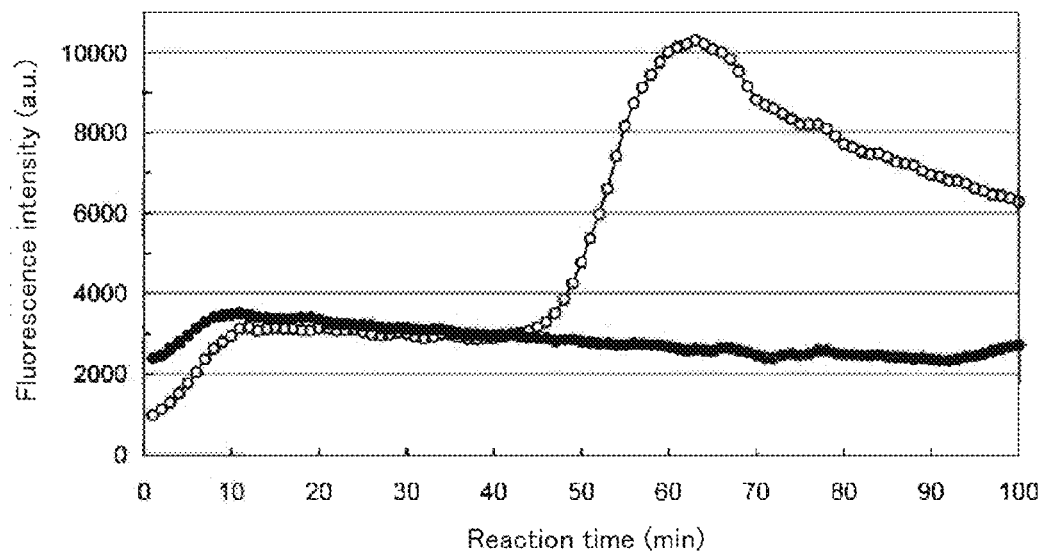
FIG. 22 is a graph showing fluorescence amplification curves obtained when Boost primers 1 and 2 of Example 3 were used.

FIG. 19 shows fluorescence amplification curves obtained when Forward Primer 4 (SEQ ID NO: 8) and Reverse Primer 4 (SEQ ID NO: 9) were used as the first primer and the second primer, respectively. FIGS. 20 to 22 show fluorescence amplification curves obtained when the third primer was used in addition to the first and second primers. FIG. 20 shows the result obtained when only Boost Primer 1 was used in the reaction. FIG. 21 shows the result obtained when only Boost Primer 2 was used in the reaction. FIG. 22 shows the result obtained when both the Boost Primers 1 and 2 were used in the reaction.

Figure 23:
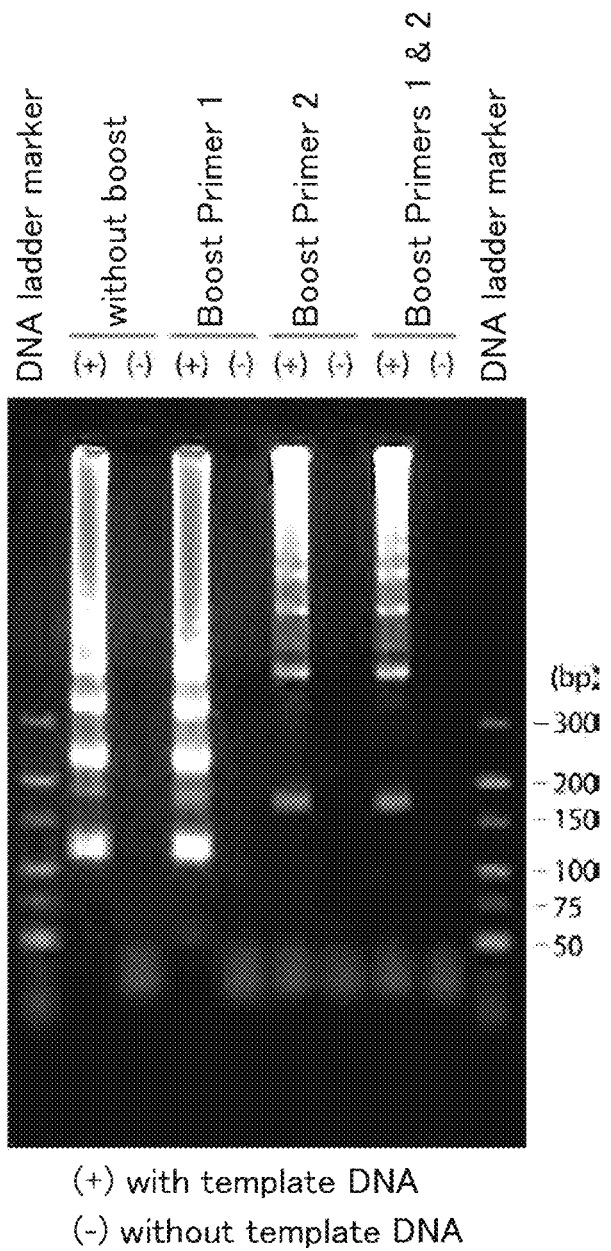
FIG. 23 is a photograph showing the result of agarose gel electrophoresis with respect to the reaction solutions exhibiting an increase in fluorescence signal in FIGS. 19 to 22.

First, according to the result shown in FIG. 19, in the reaction solution containing the template DNA, an increase in fluorescence signal was observed after 80 minutes. Next, according to the result shown in FIG. 20 obtained when Boost Primer 1 was added, the fluorescence amplification curve was not different from the fluorescence amplification curve shown in FIG. 19. However, according to the result shown in FIG. 21 obtained when Boost Primer 2 was added, an increase in fluorescence signal was observed after 50 minutes in the reaction solution containing the template DNA. Furthermore, according to the result shown in FIG. 22 obtained when both Boost Primers 1 and 2 were added, the fluorescence amplification curve exhibited an increased in signal after a lapse of a similar time as in the result shown in FIG. 21. FIG. 23 shows the results of agarose gel electrophoresis with respect to the reaction solutions exhibiting the increase in fluorescence signal in FIGS. 19 to 22. As can be seen from this result, regarding the template DNA reaction-containing solutions exhibiting the increase in fluo- rescence signal, a periodic pattern of bands indicating amplification products was observed in a region extending from a short strand to a long strand, which revealed the occurrence of isothermal nucleic acid amplification in the reaction solutions. Furthermore, it was also revealed that, in the case where Boost Primer 2 was added or both Boost Primers 1 and 2 were added, nucleic acid amplification products of longer strands increased. From the results of this electrophoresis and the results shown in FIGS. 19 to 22, it was demonstrated in the present example that the nucleic acid amplification efficiency of the isothermal nucleic acid amplification caused by the first and second primers is improved considerably by the action of Boost Primer 2 as the third primer.

Example 4

In an isothermal nucleic acid amplification method according to the present example, a reaction solution was prepared by adding Forward Primer 5 having the following sequence (SEQ ID NO: 13) and Reverse Primer 5 (SEQ ID NO: 14) so that the concentration of each primer was 2.5 μM to a solution with a volume of 25 A containing the following components with the following final concentrations: 1.4 mM dNTP, 5% DMSO, 20 mM Tris-HCl (pH 8.0), 10 mM potassium chloride, 10 mM ammonium sulfate, 8 mM magnesium sulfate, 0.1% Tween 20, 1/100000 dilution of SYBR Green I (Takara Shuzo Co., Ltd.), and 6 units of Aac DNA polymerase (Kabushiki Kaisha DNAFORM). In each of the following primers, an underlined part indicates a folding sequence, and a boxed part indicates a sequence common to the forward and reverse primers.

```
Forward Primer 5
                                              (SEQ ID NO: 13)
44-mer
5'-GCGCGCGCTAAATCGCGACTATCGTCTCAGCTATGAACACAGCA-3'

Reverse Primer 5
                                              (SEQ ID NO: 14)
49-mer
5'-GAAGGATTCCTTCTAAATCGCGACTATCGTCTTCTCCTTTTCCCATTCC-3'
```

Furthermore, as a template DNA, 6×10³ copies of a plasmid DNA having a partial sequence (SEQ ID NO: 15) of cDNA of the MP segment of the RNA genome of influenza B was added to the reaction solution. Also, for amplification from a short strand template DNA, a 52-mer oligo DNA corresponding to annealing sequences of Forward Primer 5 and Reverse Primer 5 and the cDNA partial sequence (SEQ ID NO: 15, underlined part) of the MP segment of the RNA genome influenza B flanked by these annealing sequences was used as a template DNA, and 6×10³ copies of the template DNA was added to the reaction solution.

Influenza B MP Segment, Partial cDNA (SEQ ID NO: 15)

```
740 bp
5'-AGCAGAAGCACGCACTTTCTTAAAATGTCGCTGTTTGGAGACACAAT
TGCCTACCTGCTTTCATTGACAGAAGATGGAGAAGGCAAAGCAGAACTAG
```

-continued
CAGAAAAATTACACTGTTGGTTTGGTGGGAAAGAATTTGACCTAGACTCT

GCCTTGGAATGGATAAAAAACAAAAGATGCTTAACTGATATACAAAAAGC

ACTAATTGGTGCCTCTATATGCTTTTTAAAACCCAAAGACCAGGAAAGAA

AAAGAAGATTCATCACAGAGCCCTTATCAGGAATGGGAACAACAGCAAC

AAAAAAGAAAGGCCTGATTCTGGCTGAGAGAAAAATGAGAAGATGTGTG

AGCTTTCATGAAGCATTTGAAATAGCAGAAGGCCATGAAAGCTCAGCGC

TACTATACTGTCTCATGGTCATGTACCTGAATCCTGGAAATTATTCAATG

CAAGTAAAACTAGGAACGCTCTGTGCTTTATGCGAGAAACAAGCATCACA

TTCACACAGGGCTCATAGCAGAGCAGCGAGATCTTCAGTGCCTGGAGTGA

GACGAGAAATGCAGATGG<u>TCTCAGCTATGAACACAGCAAAAACAATGAA

TGGAATGGGAAAAGGAGAAGA</u>CGTCCAAAAGCTGGCAGAAGAGCTGCA

AAGCAACATTGGAGTGCTGAGATCTCTTGGGGCAAGTCAAAAGAATGGG

GAAGGGATTGCAAAGGATGTAATGGAAGTGCTAAAGCAGAGCTCCATGG

G-3'

An isothermal nucleic acid amplification reaction was carried out by conducting incubation at a constant temperature of 60° C. for 90 minutes in a real-time PCR system MX3000p (Agilent). Then, whether or not the nucleic acid amplification occurred was examined by obtaining a fluorescence amplification curve through a FAM filter.

After the completion of the amplification reaction, in order to examine the nucleic acid amplification product, 5 µL of the solution after the reaction was applied to agarose gel electrophoresis using 4.5% (w/v) NuSieveagarose, and a band pattern was observed utilizing ethidium bromide staining. Also, regarding the amplification product obtained using the FluB cDNA plasmid as a template, DNA bands observed in the agarose electrophoresis were excised, and DNA was extracted using a Wizard SV Gel and a PCR Clean-Up System (Promega KK). A-addition to the 3' end of the purified DNA fragment was carried out by incubation at 60° C. for 10 minutes using TAKARA ExTaq DNA polymerase (Takara Shuzo Co., Ltd.), and the thus-obtained 3' A-added DNA fragment was subjected to TA cloning using a TOPO TA Cloning Kit (Life Technologies). The insert sequence in the thus-obtained cloning product was determined using a BigDye Terminator Cycle sequencing kit ver. 1.1 and an ABI 3100-Avant (Life Technologies), and the primary structure of the amplification product was analyzed on the basis of the sequence information.

(Result: Result of the Isothermal Amplification Reaction Using the Primer Set Configured so that Both the Forward and Reverse Primers have Folding Sequences Different from Each Other)

Figure 24:
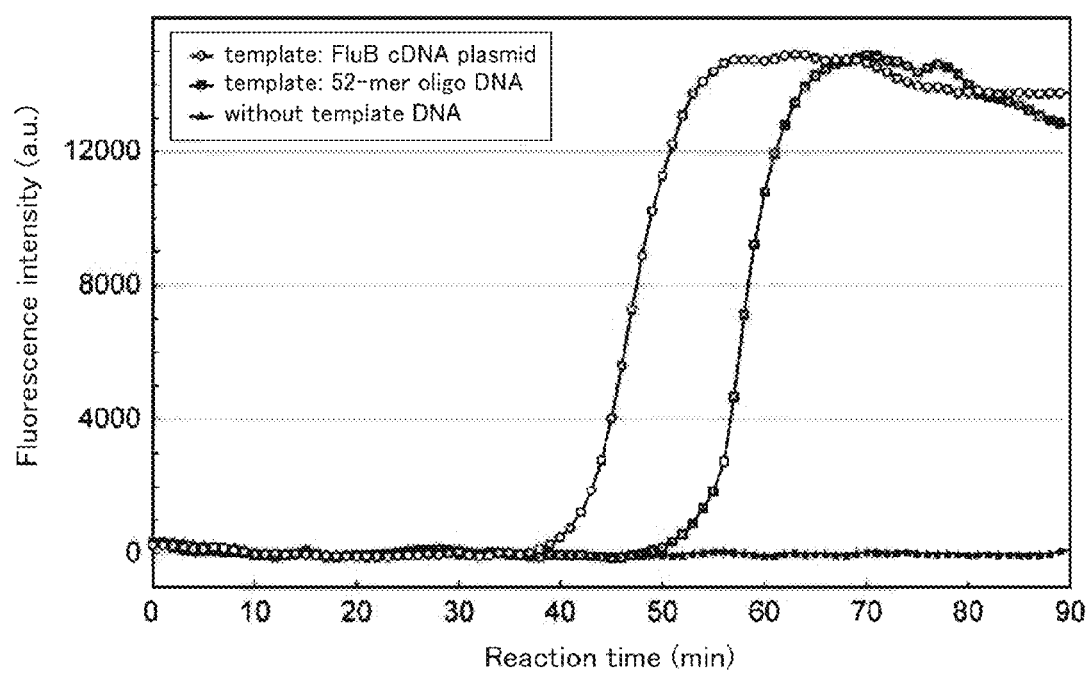
FIG. 24 is a graph showing fluorescence amplification curves obtained when the primer set of Example 4 (Forward Primer 5 and Reverse Primer 5) was used.

FIG. 24 shows fluorescence amplification curves obtained when Forward Primer 5 (SEQ ID NO: 13) and Reverse Primer 5 (SEQ ID NO: 14) were used. As a result, in each of the case where the template DNA was the plasmid including FluB cDNA (open circle) and the case where the template DNA was the 52-mer single-stranded oligo DNA consisting of the annealing sequences of both the primers and the target region in the FluB flanked by these annealing sequences (gray square), a marked increase in fluorescence signal was observed as compared with a control experiment in which the template DNA was not added (filled triangle). FIG. 25 shows the results of agarose gel electrophoresis with respect to the reaction solutions used in the amplification reactions in FIG. 24. As can be seen from FIG. 25, a periodic band pattern was observed in a region extending from a short strand to a long strand in each authentic reaction preparation containing the template DNA, which revealed the occurrence of isothermal nucleic acid amplification. Also, no difference in band pattern was observed between the case where the long double-stranded plasmid was supplied as the template DNA and the case where the short single-stranded oligo DNA was supplied as the template DNA, which revealed that the same amplification reaction occurred in these cases.

Figures 25A, 25B:
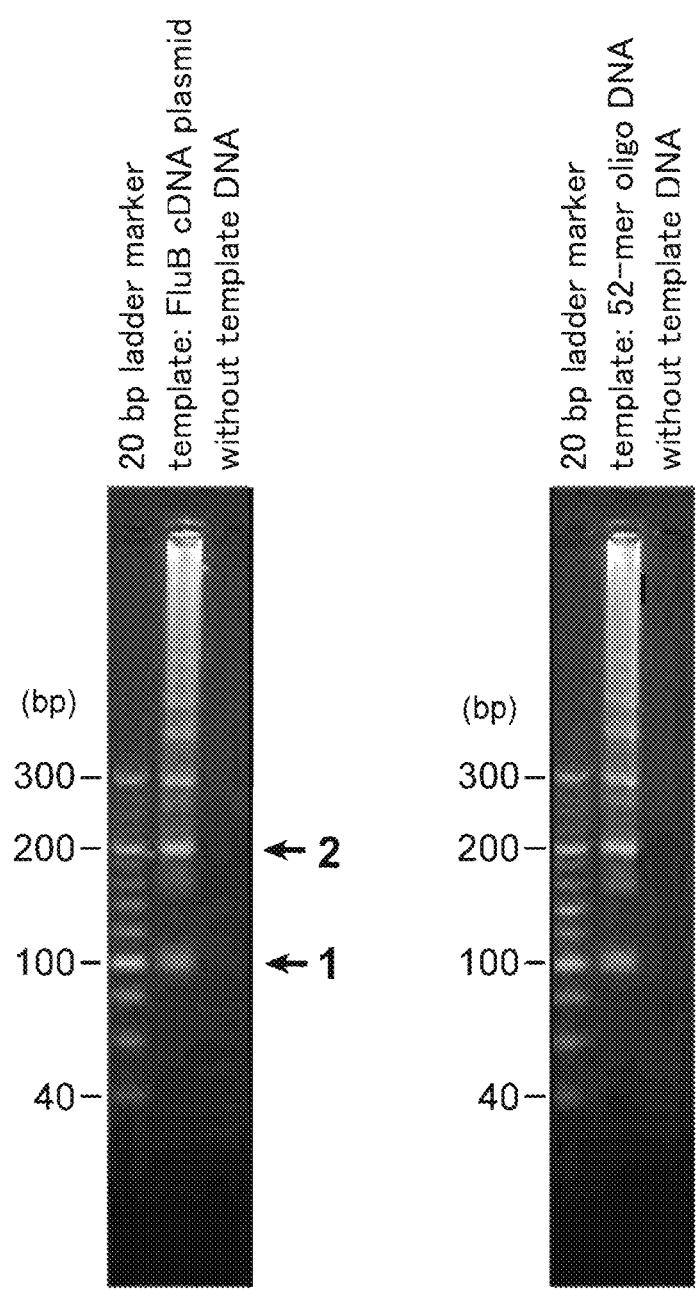
FIG. 25 shows photographs showing the result of agarose gel electrophoresis with respect to the reaction solutions exhibiting an increase in fluorescence signal in FIG. 24.
Figure 26A:
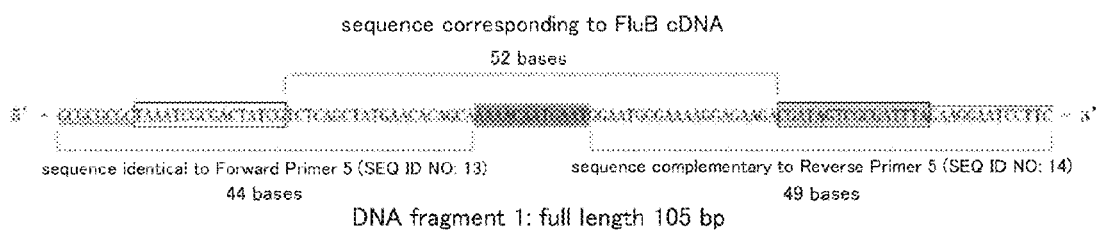
FIG. 26 shows schematic views illustrating an amplification reaction of the primer set of Example 4.
Figure 26B:
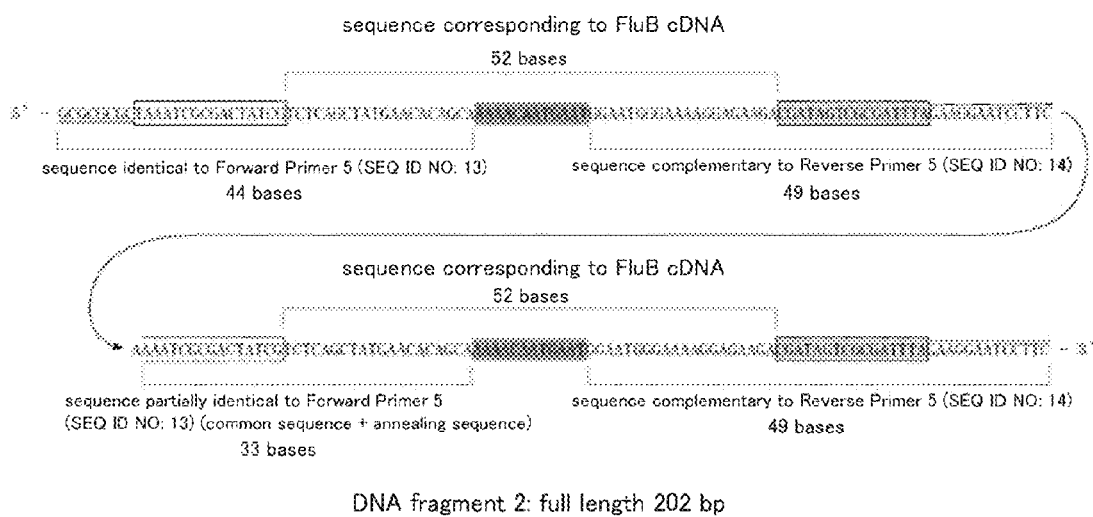

Regarding the bands indicated with the arrows 1 and 2 in FIG. 25A, FIG. 26 shows the results of determining the base sequences of these DNAs. From the DNA indicated with the arrow 1 in FIG. 25A, a base sequence of 105 bp was obtained. From the DNA indicated with the arrow 2 in FIG. 25A, a base sequence of 202 bp was obtained. These lengths substantially agreed with the DNA fragment lengths observed in the agarose electrophoresis. The primary structure of each DNA fragment was analyzed. As a result, it was found that the DNA indicated with the arrow 1 in FIG. 25A obtained from the template DNA an amplicon sequence flanked by the forward and reverse primers (FIG. 26A). It was also found that the DNA indicated with the arrow 2 in FIG. 25A had a sequence in which two amplicon sequences were linked to each other in the forward direction (tandem linkage), and the linking part of these amplicons included the folding sequence of only one of the primers (FIG. 26B).

Example 5

The present example examined the specificity of primers to a target sequence in the isothermal nucleic acid amplification method of the present invention. Forward Primer 6 (SEQ ID NO: 16) and Reverse Primer 6 (SEQ ID NO: 17) shown below were added so that the concentration of each primer was 2.5 µM to a solution with a volume of 25 µL containing the following components with the following final concentrations: 1.4 mM dNTP, 5% DMSO, 20 mM Tris-HCl (pH 8.0), 10 mM potassium chloride, 10 mM ammonium sulfate, 8 mM magnesium sulfate, 0.1% Tween 20, 1/100000 dilution of SYBR Green I (Takara Shuzo Co., Ltd.), and 6 units of Aac DNA polymerase (Kabushiki Kaisha DNAFORM). In each of the following primers, an underlined part indicates a folding sequence, and a boxed part indicates a sequence common to the forward and reverse primers.

Forward Primer 6

(SEQ ID NO: 16)

49-mer

5'-<u>GAGACTCCGGAGTCTC</u>|TCTGGCAGCGCGC|ATGTACCTGAATCCTGGAAA-3'

```
Reverse Primer 6
                                                       (SEQ ID NO: 17)
49-mer
5'-TCCGCGCGCGCGCGGATCTGGCAGCGCGCGCGTTCCTAGTTTTACTTGC-3'
```

Furthermore, as a template DNA, 6×10³ copies of a plasmid DNA having a partial sequence (SEQ ID NO: 15) of cDNA of the MP segment of the RNA genome of influenza B was added to the reaction solution. Also, a reaction solution containing human genomic DNA (Human Genomic DNA, Male, Promega KK, corresponding to 10³ copies) (20 ng per reaction solution) in addition to the template DNA was prepared.

Isothermal nucleic acid amplification reactions using the above-described reaction solutions and examination of the obtained amplification reaction products were carried out in the same manner as in Example 4.

(Result: Specificity to the Target Site in the Template DNA in the Isothermal Nucleic Acid Amplification Using the Primer Set Configured so that Both the Forward and Reverse Primers Includes Folding Sequences Different from Each Other)

Figure 27:
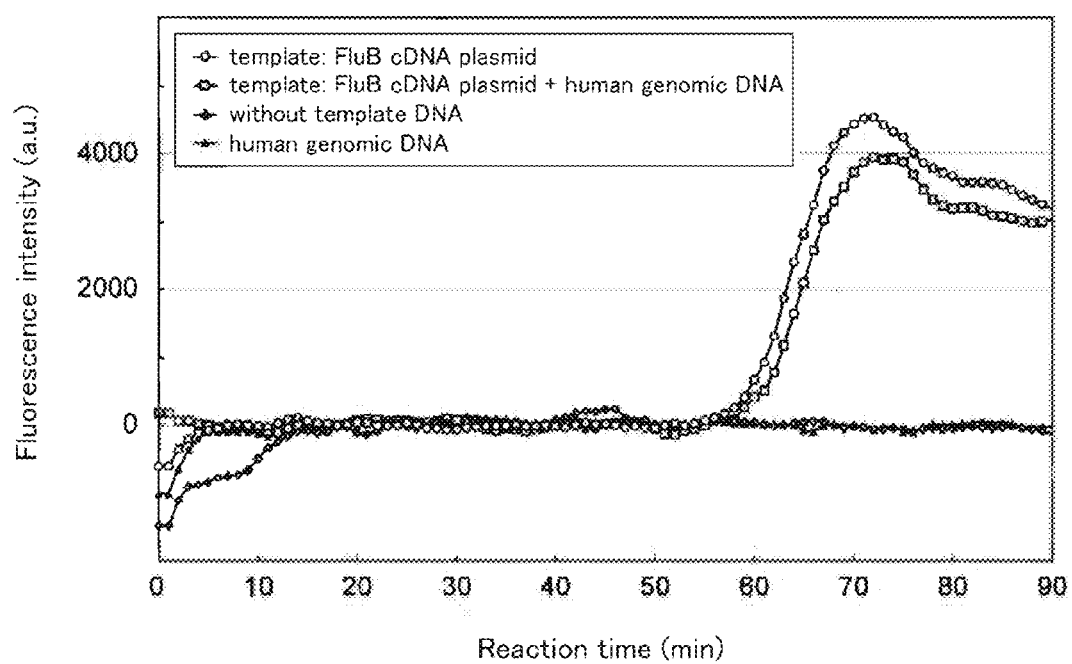
FIG. 27 is a graph showing fluorescence amplification curves obtained when the primer set of Example 5 (Forward Primer 6 and Reverse Primer 6) was used.
Figure 28A:
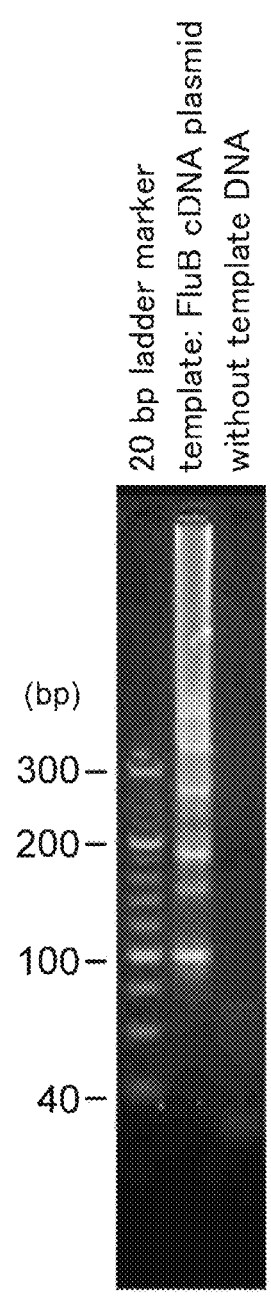
FIG. 28 shows photographs showing the result of agarose gel electrophoresis with respect to the reaction solutions exhibiting an increase in fluorescence signal in FIG. 27.

FIG. 27 shows fluorescence amplification curves obtained when Forward Primer 6 (SEQ ID NO: 16) and Reverse Primer 6 (SEQ ID NO: 17) were used as the primers, in the presence of the FluB cDNA plasmid including their target sequence as a template DNA, and also, in the presence of the human genomic DNA in addition to the template DNA. As a result, in each of the case where the template DNA was added (open circle) and the case where the human genomic DNA was further added (gray square), a marked increase in fluorescence signal was observed as compared with a control experiment in which the template DNA was not added (gray rhombus). Also, in the case where only the human genomic DNA was added as a template (filled triangle), no increase in fluorescence signal was observed. FIG. 28A shows the result of the agarose gel electrophoresis with respect to the reaction solutions used in the amplification reactions in FIG. 27. As can be seen from FIG. 28A, a periodic band pattern was observed in a region extending from a short strand to a long strand in the authentic reaction preparation containing the FluB cDNA plasmid as the template DNA, whereas, in the reaction solution containing no template DNA or only the human genomic DNA, no marked amplification pattern was observed. This revealed that the primer used in the present example achieved isothermal nucleic acid amplification and specifically recognized the FluB cDNA plasmid as the template DNA.

Figure 28B:
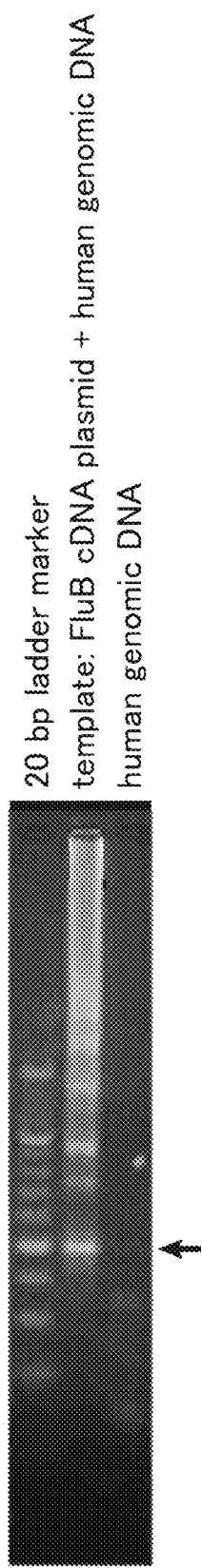
Figure 29:
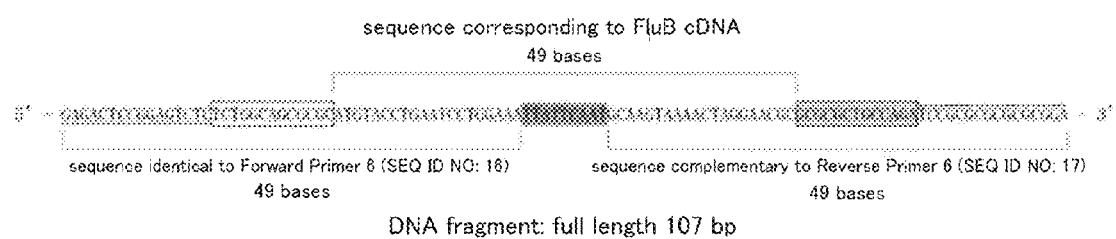
FIG. 29 is a schematic view illustrating an amplification reaction of the primer set of Example 5.

Regarding the band indicated with an arrow in FIG. 28B, FIG. 29 shows the result of determining the base sequence of the DNA. From the DNA indicated with the arrow in FIG. 28B, a base sequence of 105 bp was obtained, and this length substantially agreed with the DNA fragment length observed in the agarose electrophoresis. The primary structure of this DNA fragment was analyzed. As a result, it was found that the DNA indicated with the arrow in FIG. 28B obtained an amplicon sequence flanked by the forward and reverse primers from the template DNA, and in a region between the sequences corresponding to the 3' ends of both the primers, a sequence specific to FluB continuous from the annealing regions was included. Thus, the primary sequence structure analysis of the amplification product also verified the specificity of the primers used in the present example in target sequence recognition.

Example 6

The present example examined whether or not isothermal nucleic acid amplification can be carried out directly from a reverse transcription reaction solution with RNA as a template according to the isothermal nucleic acid amplification method of the present invention. From the plasmid DNA including the partial sequence of the FluB cDNA used in Example 4, linear double-stranded DNA of the FluB cDNA incorporating a T7 promoter sequence was prepared by a PCR method using the following primers for FluB cDNA amplification (SEQ ID NOs: 18 and 19). An in vitro transcription reaction was performed using this PCR product and CUGA T7 RNA polymerase (NIPPON GENETECH CO. LTD.), and RNA obtained from the reaction solution by acid phenol extraction was used as a template RNA in a reverse transcription reaction in the present example.

```
Forward Primer 7 for T7/FluB cDNA amplification
                                                       (SEQ ID NO: 18)
39-mer
5'-TAATACGACTCACTATAGGGAGCAGAAGCACGCACTTTC-3'

Reverse Primer 7 for T7/FluB cDNA amplification
                                                       (SEQ ID NO: 19)
20-mer
5'-CCCATGGAGCTCTGCTTTAG-3'
```

200 ng of the RNA prepared in the above-described manner was allowed to react in 25 µL of a reverse transcription reaction solution (50 mM Tris-HCl [pH 8.3], 75 mM potassium chloride, 3 mM magnesium chloride, 10 mM DTT, 200 units of M-MLV Reverse transcriptase [deletion mutant, RNaseH (-), Promega KK], and a reverse transcription primer [SEQ ID NO: 20]) at 42° C. for 1 hour. Thereafter, the reaction solution was kept at 95° C. for 5 minutes to deactivate the M-MLV Reverse transcriptase.

```
        Primer for reverse transcription
                                                       (SEQ ID NO: 20)
        18-mer
        5'-TGGACGTCTTCTCCTTTT-3'
```

1 µL of a 1/4000 dilution of the reverse transcription reaction solution was added to an isothermal amplification reaction solution (the reagent composition and the primers were the same as in Example 1), and the resultant mixture was allowed to react in a real-time PCR system MX3000p (Agilent) at a constant temperature of 60° C. for 90 minutes. Then, whether or not the nucleic acid amplification occurred was examined by obtaining a fluorescence amplification curve through a FAM filter. Also, in order to examine the nucleic acid amplification product, 5 A of the solution after the reaction was applied to agarose gel electrophoresis using 4.5% (W/V) NuSieve GTG agarose, and a band pattern was observed utilizing ethidium bromide staining.

(Result: Isothermal Nucleic Acid Amplification Directly from the Reverse Transcription Reaction Solution with RNA as a Template)

Figure 30:
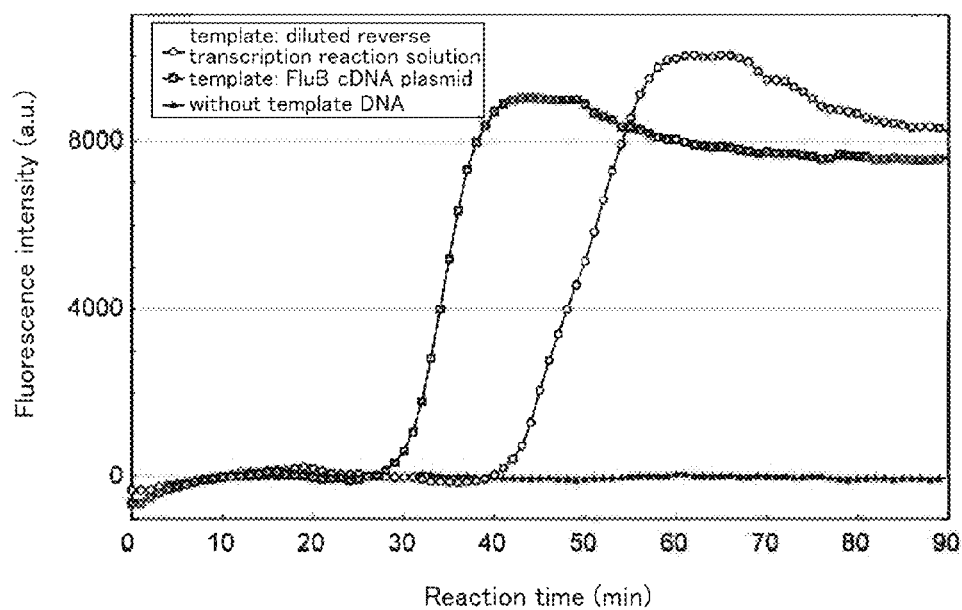
FIG. 30 is a graph showing fluorescence amplification curves obtained when the primer set of Example 6 (Forward Primer 7 and Reverse Primer 7) was used.
Figure 31:
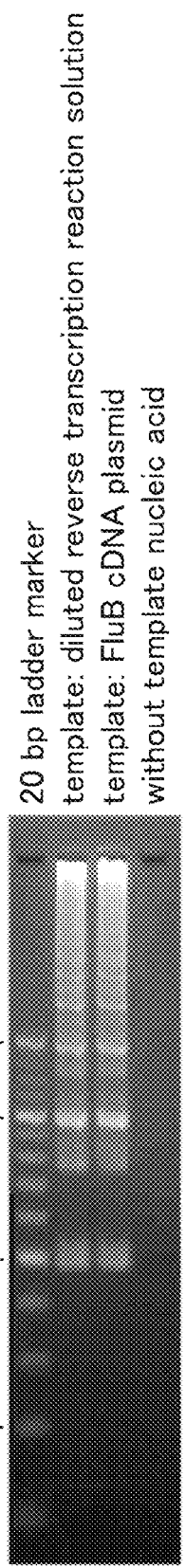
FIG. 31 is a photograph showing the result of agarose gel electrophoresis with respect to the reaction solutions exhibiting an increase in fluorescence signal in FIG. 30.

FIG. 30 shows the result of comparison between the case where the isothermal amplification reaction using Forward Primer 5 (SEQ ID NO: 13) and Reverse Primer 6 (SEQ ID NO: 14) was carried out in the presence of the authentic reaction preparation containing the 1/4000 dilution of the reverse transcription reaction solution prepared in the present example (open circle) and the case where the same isothermal amplification reaction was carried out in the presence of the same FluB cDNA plasmid as in Example 4 as a template DNA (gray square). As a result, in the authentic reaction preparation containing the reverse transcription reaction solution, a marked increase in fluorescence signal was observed as compared with a control experiment in which the template DNA was not added (filled triangle), although the rise time of the fluorescence signal was delayed as compared to the case where the plasmid was used as the template. FIG. 31 shows the results of agarose gel electrophoresis with respect to the reaction solutions used in the amplification reactions in FIG. 30. As a result, a periodic band pattern was observed in a region extending from a short strand to a long strand in the authentic reaction preparation containing the reverse transcription reaction solution, similarly to the case where the template DNA was used. This revealed the occurrence of the same isothermal nucleic acid amplification.

Example 7

The present example examined the behavior obtained when the primers for use in the isothermal nucleic acid amplification method of the present invention were configured so that a folding sequence located at the 5' end was removed from one of the primers. Forward Primer 8 shown below (SEQ ID NO: 21) and Reverse Primer 6 (SEQ ID NO: 17) used in Example 5 were added so that the concentration of each primer was 2.5 µM to a solution with a volume of 25 A containing the following components with the following final concentrations: 1.4 mM dNTP, 5% DMSO, 20 mM Tris-HCl (pH 8.0), 10 mM potassium chloride, 10 mM ammonium sulfate, 8 mM magnesium sulfate, 0.1% Tween 20, 1/100000 dilution of SYBR Green I (Takara Shuzo Co., Ltd.), and 6 units of Aac DNA polymerase (Kabushiki Kaisha DNAFORM). In the following primer, a boxed part indicates a sequence common to the forward and reverse primers. Forward Primer 8 has the same sequence as Forward Primer 6 (SEQ ID NO: 16) from which the folding sequence (16 bases) at the 5' end is removed.

Forward Primer 8
(SEQ ID NO: 21)
33-mer
5'-TCTGGCAGCGCGCATGTACCTGAATCCTGGAAA-3'

Furthermore, as a template DNA, 6×10³ copies of a plasmid DNA having a partial sequence (SEQ ID NO: 15) of cDNA of the MP segment of the RNA genome of influenza B was added to the reaction solution. Also, a reaction solution containing human genomic DNA (Human Genomic DNA, Male, Promega KK, corresponding to 10³ copies) (20 ng per reaction solution) in addition to the template DNA was prepared.

Isothermal nucleic acid amplification reactions using the above-described reaction solutions and examination of the obtained amplification reaction products were carried out in the same manner as in Example 4.

(Result: Isothermal Nucleic Acid Amplification Reaction when the 5' End Folding Sequence in One of the Primers was Removed)

Figure 32:
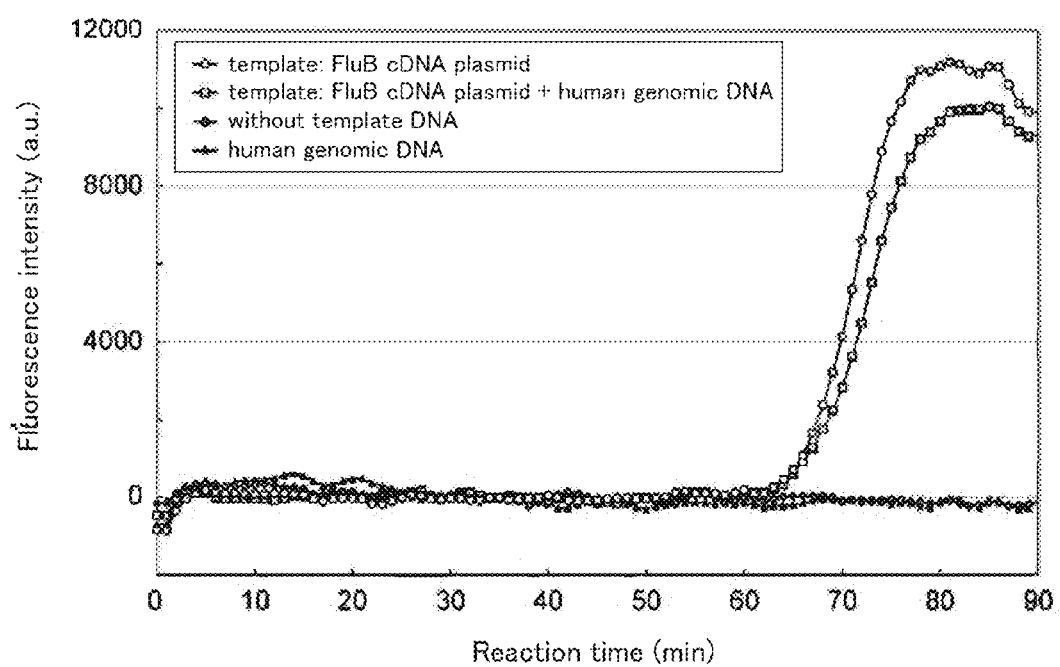
FIG. 32 is a graph showing fluorescence amplification curves obtained when the primer set of Example 7 (Forward Primer 8 and Reverse Primer 6) was used.
Figure 33:
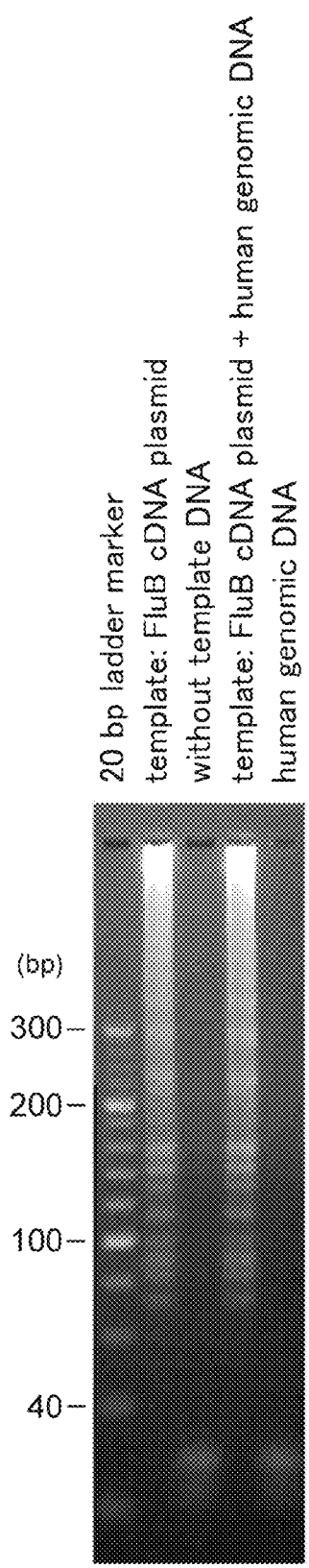
FIG. 33 is a photograph showing the result of agarose gel electrophoresis with respect to the reaction solutions exhibiting an increase in fluorescence signal in FIG. 32.

FIG. 32 shows fluorescence amplification curves obtained when Forward Primer 8 (SEQ ID NO: 21) not including a folding sequence at the 5' end thereof and Reverse Primer 6 (SEQ ID NO: 17) including a folding sequence at the 5' end thereof were used as the primers, in the presence of the FluB cDNA plasmid including their target sequence as a template DNA, and also, in the presence of the human genomic DNA in addition to the template DNA. As a result, in each of the case where the template DNA was added (open circle) and the case where the human genomic DNA was further added (gray square), a marked increase in fluorescence signal was observed as compared with a control experiment in which the template DNA was not added (gray rhombus). Also, in the case where only the human genomic DNA was added as a DNA template (filled triangle), no increase in fluorescence signal was observed. FIG. 33 shows the result of the agarose gel electrophoresis with respect to the reaction solutions used in the amplification reactions in FIG. 32. As a result, a band pattern was observed in a region extending from a short strand to a long strand in the authentic reaction preparation containing the FluB cDNA plasmid as the template DNA, whereas, in the reaction solution containing no template DNA or only the human genomic DNA, no marked amplification pattern was observed. This revealed that, even in the case where one of the primers did not include the folding sequence at the 5' end thereof, isothermal nucleic acid amplification of the target template DNA was achieved. However, from the comparison of the pattern of the bands indicating amplification products with that in Example 5 (FIG. 28), it was found that these band patterns are different. This revealed that different amplification products are obtained when the 5' end folding sequence is removed from one of the primers.

Example 8

In an isothermal nucleic acid amplification method according to the present example, a reaction solution was prepared by adding Forward Primer 5 (SEQ ID NO: 13) used in Example 4 and Reverse Primer 8 (SEQ ID NO: 22) so that the concentration of each primer was 2.5 µM to a solution with a volume of 25 A containing the following components with the following final concentrations: 1.4 mM dNTP, 5% DMSO, 20 mM Tris-HCl (pH 8.0), 10 mM potassium chloride, 10 mM ammonium sulfate, 8 mM magnesium sulfate, 0.1% Tween 20, a 1/100000 dilution of SYBR Green I (Takara Shuzo Co., Ltd.), and 6 units of Aac DNA polymerase (Kabushiki Kaisha DNAFORM). In the following primer, a boxed part indicates a sequence common to the forward and reverse primers. Reverse Primer 8 has the same sequence as Reverse Primer 5 (SEQ ID NO: 14) from which the folding sequence (13 bases) at the 5' end is removed.

Reverse Primer 8
(SEQ ID NO: 22)
36-mer
5'-TAAATCGCGACTATCGTCTTCTCCTTTTCCCATTCC-3'

Furthermore, as a template DNA, 6×10³ copies of a plasmid DNA having a partial sequence (SEQ ID NO: 15) of cDNA of the MP segment of the RNA genome of influenza B was added to the reaction solution.

Isothermal nucleic acid amplification reactions using the above-described reaction solutions, electrophoresis of the amplification reaction product, and sequence analysis of the obtained amplification products were carried out in the same manner as in Example 4.

(Result: Isothermal Nucleic Acid Amplification Reaction when the 5' End Folding Sequence in One of the Primers was Removed and Sequence Analysis of the Obtained Amplification Products)

Figure 34:
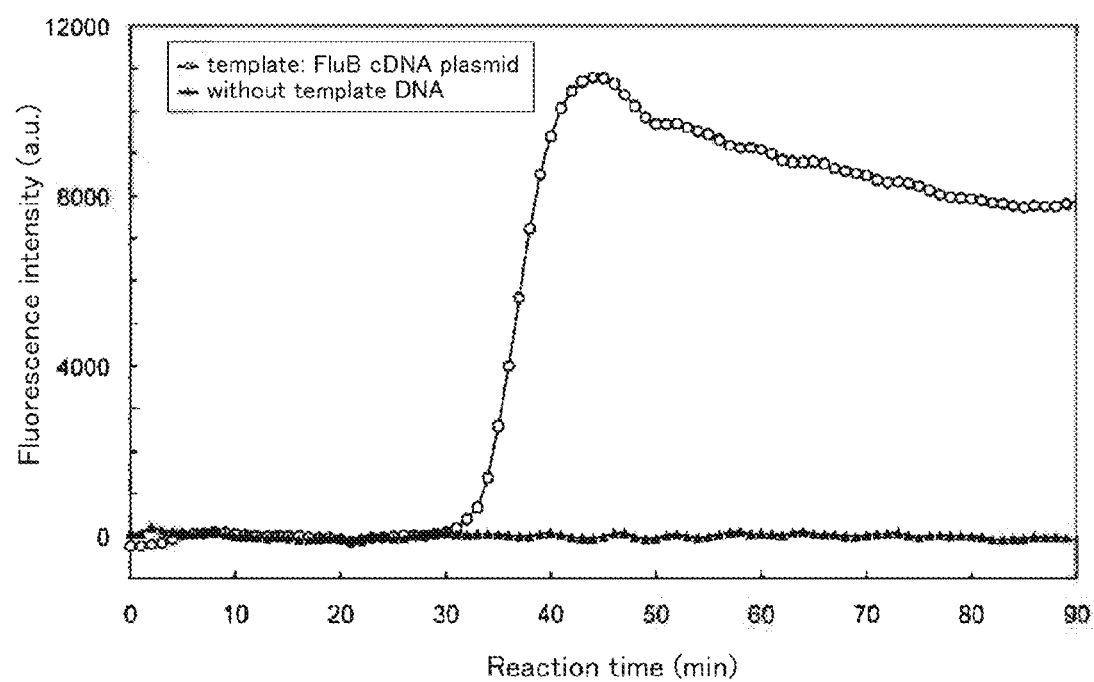
FIG. 34 is a graph showing fluorescence amplification curves obtained when the primer set of Example 8 (Forward Primer 5 and Reverse Primer 8) was used.
Figure 35:
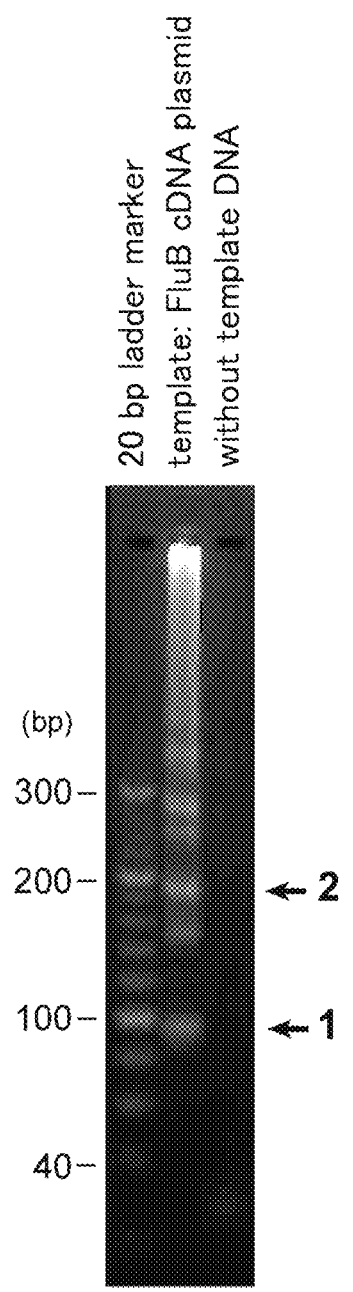
FIG. 35 is a photograph showing the result of agarose gel electrophoresis with respect to the reaction solution exhibiting an increase in fluorescence signal in FIG. 34.

FIG. 34 shows fluorescence amplification curves obtained when Forward Primer 5 (SEQ ID NO: 13) including a folding sequence at the 5' end thereof and Reverse Primer 8 (SEQ ID NO: 22) not including a folding sequence at the 5' end thereof were used as the primers, in the presence of the FluB cDNA plasmid including their target sequence as a template DNA. As a result, in the case where the plasmid including the FluB cDNA was added as the template DNA (open circle), a marked increase in fluorescence signal was observed as compared with a control experiment in which the template DNA was not added (filled triangle). FIG. 35 shows the result of the agarose gel electrophoresis with respect to the reaction solutions used in the amplification reactions in FIG. 34. As a result, a periodic band pattern was observed in a region extending from a short strand to a long strand in the authentic reaction preparation containing the template DNA, which revealed the occurrence of isothermal nucleic acid amplification.

Figure 36A:
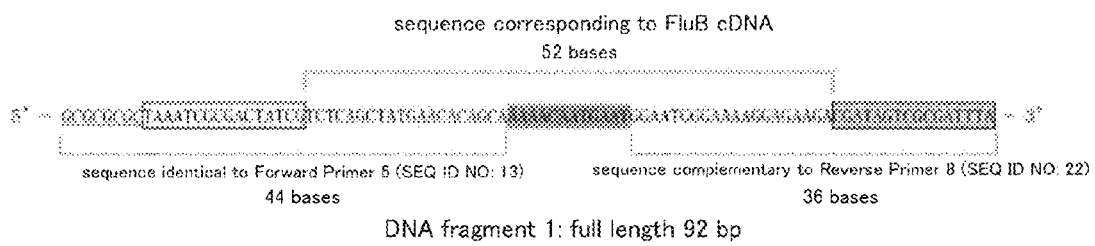
FIG. 36 shows schematic views illustrating an amplification reaction using the primer set of Example 8.
Figure 36B:
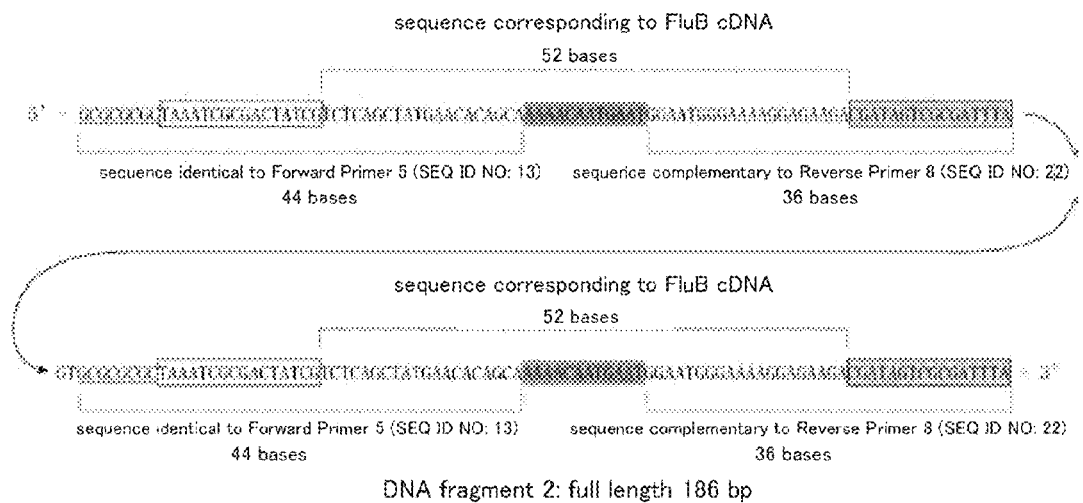

Regarding the bands indicated with the arrows 1 and 2 in FIG. 35, FIG. 36 shows the results of determining the base sequences of these DNAs. From the DNA indicated with the arrow 1 in FIG. 35, a base sequence of 92 bp was obtained. From the DNA indicated with the arrow 2 in FIG. 35, a base sequence of 186 bp was obtained. These lengths substantially agreed with the DNA fragment lengths observed in the agarose electrophoresis. The primary structure of each DNA fragment was analyzed. As a result, it was found that the DNA indicated with the arrow 1 in FIG. 35 has a sequence copied from an amplicon sequence flanked by the forward and reverse primers obtained from the template DNA (FIG. 36A). It was also found that the DNA indicated with the arrow 2 in FIG. 35 had a sequence in which two amplicon sequences are linked to each other in the forward direction (tandem) via two bases GT (guanine and thymine) (FIG. 36B).

While the present invention has been described above with reference to illustrative embodiments, the present invention is by no means limited thereto. Various changes and modifications that may become apparent to those skilled in the art may be made in the configuration and specifics of the present invention without departing from the scope of the present invention. Furthermore, the disclosures of all the documents referenced in this specification are incorporated herein by reference in their entirety.

The invention claimed is:

1. A primer set for use in a method for isothermally amplifying a target nucleic acid sequence, the primer set comprising:
   a first primer; and
   a second primer,
   wherein the first primer comprises, on the 3' side thereof, a sequence (A') that can hybridize to a sequence (A) on the 3' side of the target nucleic acid sequence,
   the second primer comprises, on the 3' side thereof, a sequence (B') that can hybridize to a sequence (B) on the 3' side of either a strand extended from the first primer or a strand complementary to the target nucleic acid sequence, and
   the first primer and the second primer comprise, on the 5' sides thereof, sequences (C) that are substantially identical to each other,
   wherein at least one of the first primer and the second primer further comprises, on the 5' side of the sequence (C), a folding sequence (D-D') comprising, on the same strand, two sequences that hybridize to each other.

2. The primer set according to claim 1, wherein
   the first primer further comprises, on the 5' side of the sequence (C), a folding sequence (D-D') comprising, on the same strand, two sequences that hybridize to each other,
   the second primer further comprises, on the 5' side of the sequence (C), a folding sequence (E-E') comprising, on the same strand, two sequences that hybridize to each other, and
   the sequence (D-D') and the sequence (E-E') are different from each other.

3. The primer set according to claim 1, further comprising a third primer,
   wherein the third primer hybridizes to the target nucleic acid sequence, a sequence complementary to the target nucleic acid sequence, or a strand extended from the first primer or the second primer, and
   the hybridization of the third primer does not compete with the first primer and the second primer.

4. A method, comprising isothermally amplifying a target nucleic acid sequence using a primer set, wherein
   the primer set is the primer set according to claim 1.

5. A method for detecting a mutation in a nucleic acid sequence in a nucleic acid sample by an isothermal amplification method using a primer set, wherein
   the primer set is the primer set according to claim 1,
   the primer set is designed so that the primer set targets a nucleic acid sequence having or not having the mutation and that a nucleotide residue corresponding to the mutation is included in the sequence (A) complementary to the sequence (A') in the first primer or in the sequence (B) complementary to the sequence (B') in the second primer,
   the method comprising carrying out an isothermal amplification reaction using the primer set in the presence of the nucleic acid sample.

6. A nucleic acid synthesis method for isothermally synthesizing a double-stranded nucleic acid composed of a single-stranded nucleic acid in which the order of at least two different sequences is repeated to a total of two or more times and a nucleic acid complementary to the single-stranded nucleic acid, the nucleic acid synthesis method comprising the following steps (A1) to (A6):
   (A1) providing a single-stranded template nucleic acid having a stem-loop structure in which a 3' side stem sequence comprising the 3' end and a 5' side stem sequence comprising the 5' end are linked to each other via a loop sequence, with a folding sequence comprising, on the same strand, two sequences that hybridize to each other being linked to the 3' end of the 3' side stem sequence;
   (A2) hybridizing a primer to the loop of the single-stranded template nucleic acid and extending the primer toward the 5' end of the 5' side stem sequence;

(A3) successively continuing the extension of the primer that has reached the 5' end of the 5' side stem sequence from the 5' end of the 5' side stem sequence to the 3' end of the folding sequence;

(A4) successively continuing the extension of the primer that has reached the 3' end of the folding sequence in the step (A3) toward the 5' end of the 5' side stem sequence again, and, by the continuing primer extension, rendering the primer-extended strand hybridizing to the single-stranded template nucleic acid formed in the step (A2) single-stranded through a strand displacement reaction;

(A5) terminating the extension of the primer in the step (A4) at the 5' end of the 5' side stem sequence; and (A6) extending the 3' end of the folding sequence in the single-stranded template nucleic acid using the primer-extended strand that has been rendered single-stranded in the step (A4) as a template.

7. The nucleic acid synthesis method according to claim 6, wherein the step (A3) and the step (A4) are repeated to a total of two or more times.

8. The nucleic acid synthesis method according to claim 6, wherein the single-stranded template nucleic acid provided in the step (A1) is a single-stranded template nucleic acid formed by an isothermal amplification reaction using a primer set comprising:
a first primer; and
a second primer,
wherein the first primer comprises, on the 3' side thereof, a sequence (A') that can hybridize to a sequence (A) on the 3' side of the target nucleic acid sequence,
the second primer comprises, on the 3' side thereof, a sequence (B') that can hybridize to a sequence (B) on the 3' side of either a strand extended from the first primer or a strand complementary to the target nucleic acid sequence, and
the first primer and the second primer comprise, on the 5' sides thereof, sequences (C) that are substantially identical to each other, and
at least one of the first primer and the second primer further comprises, on the 5' side of the sequence (C), a folding sequence (D-D') comprising, on the same strand, two sequences that hybridize to each other,
wherein only the first primer comprises the folding sequence (D-D'), and
the primer hybridized to the loop in the step (A2) is the first primer comprising the folding sequence (D-D').

9. The nucleic acid synthesis method according to claim 6, wherein the single-stranded template nucleic acid provided in the step (A1) further comprises a folding sequence comprising, on the same strand, two sequences that hybridize to each other and being linked to the 5' end of the 5' side stem-loop sequence, and
the nucleic acid synthesis method comprises, instead of the step (A3), the following step (A3-2):

(A3-2) successively continuing the extension of the primer that has reached the 5' end of the 5' side stem sequence from the 5' end of the 5' side stem sequence directly to the 3' end of the folding sequence, without mediation of the folding sequence linked to the 5' end of the 5' side stem sequence.

10. The nucleic acid synthesis method according to claim 9, wherein the step (A3-2) and the step (A4) are repeated to a total of two or more times.

11. The nucleic acid synthesis method according to claim 9, wherein the single-stranded template nucleic acid provided in the step (A1) is a single-stranded template nucleic acid formed by an isothermal amplification method using a primer set
comprising:
a first primer; and
a second primer,
wherein the first primer comprises, on the 3' side thereof, a sequence (A') that can hybridize to a sequence (A) on the 3' side of the target nucleic acid sequence,
the second primer comprises, on the 3' side thereof, a sequence (B') that can hybridize to a sequence (B) on the 3' side of either a strand extended from the first primer or a strand complementary to the target nucleic acid sequence, and
the first primer and the second primer comprise, on the 5' sides thereof, sequences (C) that are substantially identical to each other,
wherein at least one of the first primer and the second primer further comprises, on the 5' side of the sequence (C), a folding sequence (D-D') comprising, on the same strand, two sequences that hybridize to each other,
the first primer further comprises, on the 5' side of the sequence (C), a folding sequence (D-D') comprising, on the same strand, two sequences that hybridize to each other,
the second primer further comprises, on the 5' side of the sequence (C), a folding sequence (E-E') comprising, on the same strand, two sequences that hybridize to each other,
the sequence (D-D') and the sequence (E-E') are different from each other, and
the primer hybridized to the loop in the step (A2) is the first primer or the second primer of the primer set.

12. A nucleic acid amplification method comprising the step of:
isothermally synthesizing a double-stranded nucleic acid composed of a single-stranded nucleic acid in which the order of at least two different sequences is repeated to a total of two or more times and a nucleic acid complementary to the single-stranded nucleic acid,
wherein the step of synthesizing the nucleic acid is carried out by the nucleic acid synthesis method according to claim 6.

13. A nucleic acid synthesis method for isothermally synthesizing a double-stranded nucleic acid composed of a single-stranded nucleic acid in which the order of at least two different sequences is repeated to a total of two or more times and a nucleic acid complementary to the single-stranded nucleic acid, the nucleic acid synthesis method comprising at least one of:
a first reaction step; and
a second reaction step,
the first reaction step comprising the following steps (B1) to (B3):

(B1) providing two double strands in a state where their sequences are in opposite orientations, the double strands each being composed of a single-stranded nucleic acid that comprises, in a region comprising the 3' end, a folding sequence comprising, on the same strand, two sequences that hybridize to each other and a single-stranded nucleic acid complementary to the single-stranded nucleic acid;

(B2) extending, through a strand displacement reaction, the 3' end of the folding sequence in the single-stranded nucleic acid in one of the two double strands provided in the step (B1) using the complementary single-stranded nucleic acid in the other double strand as a template, thereby forming a partial double strand in which part of the extended strand of the single-stranded nucleic acid in said one of the double strands hybridizes to the complementary single-stranded nucleic acid in the other double strand; and (B3) extending, in the partial double strand in the step (B2), the 3' end of the complementary single-stranded nucleic acid using the single-stranded nucleic acid as a template, thereby forming a complete double strand, the second reaction step comprising the following steps (C1) to (C3):

(C1) providing one double strand composed of a single-stranded nucleic acid that comprises, in a region comprising the 3' end, a folding sequence comprising, on the same strand, two sequences that hybridize to each other and a single-stranded nucleic acid complementary to the single-stranded nucleic acid;

(C2) extending, through a strand displacement reaction, the 3' end of the folding sequence in the single-stranded nucleic acid in the double strand provided in the step (C1) using the complementary single-stranded nucleic acid as a template from the 3' end to the 5' end of the complementary single-stranded nucleic acid, thereby forming a partial double strand in which part of the extended strand of the single-stranded nucleic acid hybridizes to the complementary single-stranded nucleic acid; and (C3) extending, in the partial double strand in the step (C2), the 3' end of the complementary single-stranded nucleic acid using the single-stranded nucleic acid as a template, thereby forming a complete double strand.

14. The nucleic acid synthesis method according to claim 13, wherein each double strand in the steps (B1) and (C1) is a double strand formed by an isothermal amplification reaction using a primer set comprising:

a first primer; and a second primer, wherein the first primer comprises, on the 3' side thereof, a sequence (A') that can hybridize to a sequence (A) on the 3' side of the target nucleic acid sequence, the second primer comprises, on the 3' side thereof, a sequence (B') that can hybridize to a sequence (B) on the 3' side of either a strand extended from the first primer or a strand complementary to the target nucleic acid sequence, and the first primer and the second primer comprise, on the 5' sides thereof, sequences (C) that are substantially identical to each other, wherein at least one of the first primer and the second primer further comprises, on the 5' side of the sequence (C), a folding sequence (D-D') comprising, on the same strand, two sequences that hybridize to each other, the first primer further comprises, on the 5' side of the sequence (C), a folding sequence (D-D') comprising, on the same strand, two sequences that hybridize to each other, the second primer further comprises, on the 5' side of the sequence (C), a folding sequence (E-E') comprising, on the same strand, two sequences that hybridize to each other, and the sequence (D-D') and the sequence (E-E') are different from each other.

15. A nucleic acid amplification method comprising the step of:

isothermally synthesizing a double-stranded nucleic acid composed of a single-stranded nucleic acid in which the order of at least two different sequences is repeated to a total of two or more times and a nucleic acid complementary to the single-stranded nucleic acid, wherein the step of synthesizing the nucleic acid is carried out by the nucleic acid synthesis method according to claim 13.

16. The nucleic acid synthesis method according to claim 13, wherein each double strand in the steps (B1) and (C1) is a double strand formed by an isothermal amplification reaction using a primer set comprising:

a first primer; and a second primer, wherein the first primer comprises, on the 3' side thereof, a sequence (A') that can hybridize to a sequence (A) on the 3' side of the target nucleic acid sequence, the second primer comprises, on the 3' side thereof, a sequence (B') that can hybridize to a sequence (B) on the 3' side of either a strand extended from the first primer or a strand complementary to the target nucleic acid sequence, and the first primer and the second primer comprise, on the 5' sides thereof, sequences (C) that are substantially identical to each other, and at least one of the first primer and the second primer further comprises, on the 5' side of the sequence (C), a folding sequence (D-D') comprising, on the same strand, two sequences that hybridize to each other.

* * * * *

SEQUENCE LISTING

```
<160> NUMBER OF SEQ ID NOS: 22

<210> SEQ ID NO 1
<211> LENGTH: 44
<212> TYPE: DNA
<213> ORGANISM: Artificial
<220> FEATURE:
<223> OTHER INFORMATION: forward primer

<400> SEQUENCE: 1
aggacgctga gatgcgtcct agcgatgcgt agacaactgg aaag              44

<210> SEQ ID NO 2
<211> LENGTH: 45
<212> TYPE: DNA
<213> ORGANISM: Artificial
<220> FEATURE:
<223> OTHER INFORMATION: forward primer

<400> SEQUENCE: 2
aatatatata tatattcgga ggaggtggag gagacaactg gaaag             45

<210> SEQ ID NO 3
<211> LENGTH: 24
<212> TYPE: DNA
<213> ORGANISM: Artificial
<220> FEATURE:
<223> OTHER INFORMATION: reverse primer

<400> SEQUENCE: 3
agcgatgcgt atgggcctat tgga                                    24

<210> SEQ ID NO 4
<211> LENGTH: 53
<212> TYPE: DNA
```

```
<213> ORGANISM: Artificial
<220> FEATURE:
<223> OTHER INFORMATION: reverse primer

<400> SEQUENCE: 4
accttctgtt caccctcaga aggtcggagg aggtggagga tgggcctatt gga        53

<210> SEQ ID NO 5
<211> LENGTH: 401
<212> TYPE: DNA
<213> ORGANISM: Artificial
<220> FEATURE:
<223> OTHER INFORMATION: plasmid DNA

<400> SEQUENCE: 5
ccaggagtca gaatgcgttt gtatcaatgg aacttgtaca gtagtaatga ctgatgggag    60
tgcttcagga aaagctgata ctaaaatact attcattgag gaggggaaaa tcgttcatac   120
tagcacattg tcaggaagtg ctcagcatgt cgaggagtgc tcctgctatc ctcgatatcc   180
tggtgtcaga tgtgtctgca gagacaactg gaaaggctcc aataggccca tcgtagatat   240
aaacataaag gatcatagca ttgtttccag ttatgtgtgt tcaggacttg ttggagacac   300
acccagaaaa aacgacagct ccagcagtag ccattgtttg gatcctaaca atgaagaagg   360
tggtcatgga gtgaaaggct gggcctttga tgatggaaat g                      401

<210> SEQ ID NO 6
<211> LENGTH: 43
<212> TYPE: DNA
<213> ORGANISM: Artificial
<220> FEATURE:
<223> OTHER INFORMATION: forward primer

<400> SEQUENCE: 6
gcattcaccc ccccgattag atattctata gacaactgga aag                    43

<210> SEQ ID NO 7
<211> LENGTH: 55
<212> TYPE: DNA
<213> ORGANISM: Artificial
<220> FEATURE:
<223> OTHER INFORMATION: reverse primer

<400> SEQUENCE: 7
aggacgctga gatgcgtcct ttttttgatt agatattcta tatgggccta ttgga        55

<210> SEQ ID NO 8
<211> LENGTH: 54
<212> TYPE: DNA
<213> ORGANISM: Artificial
<220> FEATURE:
<223> OTHER INFORMATION: forward primer

<400> SEQUENCE: 8
aggacgctga gatgcgtcct tttagcgatg cgttgaatat aaacttgtgg tagt         54

<210> SEQ ID NO 9
<211> LENGTH: 44
<212> TYPE: DNA
<213> ORGANISM: Artificial
<220> FEATURE:
<223> OTHER INFORMATION: reverse primer

<400> SEQUENCE: 9
gcgactcgcc ccagcgatgc gtctgaatta gctgtatcgt caag                   44
```

<210> SEQ ID NO 10
<211> LENGTH: 10
<212> TYPE: DNA
<213> ORGANISM: Artificial
<220> FEATURE:
<223> OTHER INFORMATION: boost primer

<400> SEQUENCE: 10
caagagtgcc                                                          10

<210> SEQ ID NO 11
<211> LENGTH: 11
<212> TYPE: DNA
<213> ORGANISM: Artificial
<220> FEATURE:
<223> OTHER INFORMATION: boost primer

<400> SEQUENCE: 11
ccaccagctc c                                                        11

<210> SEQ ID NO 12
<211> LENGTH: 401
<212> TYPE: DNA
<213> ORGANISM: Homo sapiens

<400> SEQUENCE: 12
tttcatgatt gaattttgta aggtattttg aaataatttt tcatataaag gtgagtttgt    60
attaaaaggt actggtggag tatttgatag tgtattaacc ttatgtgtga catgttctaa   120
tatagtcaca ttttcattat ttttattata aggcctgctg aaaatgactg aatataaact   180
tgtggtagtt ggagctggtg gcgtaggcaa gagtgccttg acgatacagc taattcagaa   240
tcattttgtg gacgaatatg atccaacaat agaggtaaat cttgttttaa tatgcatatt   300
actggtgcag gaccattctt tgatacagat aaaggtttct ctgaccattt tcatgagtac   360
ttattacaag ataattatgc tgaaagttaa gttatctgaa a                       401

<210> SEQ ID NO 13
<211> LENGTH: 44
<212> TYPE: DNA
<213> ORGANISM: Artificial
<220> FEATURE:
<223> OTHER INFORMATION: forward primer

<400> SEQUENCE: 13
gcgcgcgcta atcgcgact atcgtctcag ctatgaacac agca                     44

<210> SEQ ID NO 14
<211> LENGTH: 49
<212> TYPE: DNA
<213> ORGANISM: Artificial
<220> FEATURE:
<223> OTHER INFORMATION: reverse primer

<400> SEQUENCE: 14
gaaggattcc ttctaaatcg cgactatcgt cttctccttt tcccattcc                49

<210> SEQ ID NO 15
<211> LENGTH: 740
<212> TYPE: DNA
<213> ORGANISM: Influenza B virus

<400> SEQUENCE: 15

```
agcagaagca cgcactttct taaaatgtcg ctgtttggag acacaattgc ctacctgctt      60
tcattgacag aagatggaga aggcaaagca gaactagcag aaaaattaca ctgttggttt     120
ggtgggaaag aatttgacct agactctgcc ttggaatgga taaaaacaa aagatgctta     180 actgatatac aaaaagcact aattggtgcc tctatatgct tttaaaacc caaagaccag     240 gaaagaaaaa gaagattcat cacagagccc ttatcaggaa tgggaacaac agcaacaaaa     300
aagaaaggcc tgattctggc tgagagaaaa atgagaagat gtgtgagctt tcatgaagca     360
tttgaaatag cagaaggcca tgaaagctca gcgctactat actgtctcat ggtcatgtac     420
ctgaatcctg gaaattattc aatgcaagta aaactaggaa cgctctgtgc tttatgcgag     480
aaacaagcat cacattcaca cagggctcat agcagagcag cgagatcttc agtgcctgga     540
gtgagacgag aaatgcagat ggtctcagct atgaacacag caaaaacaat gaatggaatg     600
ggaaaaggag aagacgtcca aaagctggca gaagagctgc aaagcaacat tggagtgctg     660
agatctcttg gggcaagtca aaagaatggg gaagggattg caaaggatgt aatggaagtg     720
ctaaagcaga gctccatggg                                                 740
```

<210> SEQ ID NO 16
<211> LENGTH: 49
<212> TYPE: DNA
<213> ORGANISM: Artificial
<220> FEATURE:
<223> OTHER INFORMATION: forward primer
<400> SEQUENCE: 16

```
gagactccgg agtctctctg gcagcgcgca tgtacctgaa tcctggaaa                  49
```

<210> SEQ ID NO 17
<211> LENGTH: 49
<212> TYPE: DNA
<213> ORGANISM: Artificial
<220> FEATURE:
<223> OTHER INFORMATION: reverse primer
<400> SEQUENCE: 17

```
tccgcgcgcg cgcggatctg gcagcgcgcg cgttcctagt tttacttgc                  49
```

<210> SEQ ID NO 18
<211> LENGTH: 39
<212> TYPE: DNA
<213> ORGANISM: Artificial
<220> FEATURE:
<223> OTHER INFORMATION: forward primer
<400> SEQUENCE: 18

```
taatacgact cactataggg agcagaagca cgcactttc                             39
```

<210> SEQ ID NO 19
<211> LENGTH: 20
<212> TYPE: DNA
<213> ORGANISM: Artificial
<220> FEATURE:
<223> OTHER INFORMATION: reverse primer
<400> SEQUENCE: 19

```
cccatggagc tctgctttag                                                  20
```

<210> SEQ ID NO 20
<211> LENGTH: 18
<212> TYPE: DNA
<213> ORGANISM: Artificial

```
<220> FEATURE:
<223> OTHER INFORMATION: RT primer

<400> SEQUENCE: 20
tggacgtctt ctcctttt                                              18

<210> SEQ ID NO 21
<211> LENGTH: 33
<212> TYPE: DNA
<213> ORGANISM: Artificial
<220> FEATURE:
<223> OTHER INFORMATION: forward primer

<400> SEQUENCE: 21
tctggcagcg cgcatgtacc tgaatcctgg aaa                             33

<210> SEQ ID NO 22
<211> LENGTH: 36
<212> TYPE: DNA
<213> ORGANISM: Artificial
<220> FEATURE:
<223> OTHER INFORMATION: reverse primer

<400> SEQUENCE: 22
taaatcgcga ctatcgtctt ctccttttcc cattcc                          36
```